US007635466B1

(12) United States Patent
Fiers

(10) Patent No.: US 7,635,466 B1
(45) Date of Patent: *Dec. 22, 2009

(54) DNA SEQUENCES, RECOMBINANT DNA MOLECULES AND PROCESSES FOR PRODUCING HUMAN FIBROBLAST INTERFERON-LIKE POLYPEPTIDES

(75) Inventor: Walter Charles Fiers, Destelbergen (BE)

(73) Assignee: Biogen Idec MA Inc., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 08/452,658

(22) Filed: May 25, 1995

Related U.S. Application Data

(60) Division of application No. 07/387,503, filed on Jul. 28, 1989, now abandoned, which is a continuation of application No. 06/250,609, filed on Apr. 3, 1981, now abandoned.

(30) Foreign Application Priority Data

Apr. 3, 1980 (GB) .................................. 8011306
Jun. 6, 1980 (GB) .................................. 8018701

(51) Int. Cl.
*A61K 38/21* (2006.01)
(52) U.S. Cl. ...................................... 424/85.4; 514/12
(58) Field of Classification Search .............. 435/172.3, 435/69.51; 536/23.52; 530/351; 514/12; 424/85.4
See application file for complete search history.

(56) References Cited

U.S. PATENT DOCUMENTS

| | | | |
|---|---|---|---|
| 3,699,222 A | 10/1972 | Isaacs et al. | 424/85.4 |
| 4,184,917 A | 1/1980 | Dorner et al. | 435/68.1 |
| 4,190,495 A | 2/1980 | Curtiss, III | 435/172.3 |
| 4,237,224 A | 12/1980 | Cohen et al. | 435/69.1 |
| 4,241,174 A | 12/1980 | Familletti et al. | 435/5 |
| 4,262,090 A | 4/1981 | Colby et al. | 435/91.33 |
| 4,264,731 A | 4/1981 | Shine | 435/91.41 |
| 4,266,024 A | 5/1981 | Swetly et al. | 435/70.5 |
| 4,283,489 A | 8/1981 | Goodman et al. | 435/6 |
| 4,289,850 A | 9/1981 | Robinson | 435/70.5 |
| 4,293,652 A | 10/1981 | Cohen | 435/172.3 |
| 4,302,533 A | 11/1981 | Revel et al. | 435/4 |
| 4,307,193 A | 12/1981 | Iizuka | 435/70.5 |
| 4,314,935 A | 2/1982 | Uemura et al. | 530/351 |
| 4,315,852 A | 2/1982 | Leibowitz et al. | 530/351 |
| 4,322,497 A | 3/1982 | Hershberger | 435/172.3 |
| 4,874,702 A | 10/1989 | Fiers et al. | 435/252.33 |
| 5,326,859 A * | 7/1994 | Sugano et al. | 536/23.52 |
| 5,401,642 A | 3/1995 | Fiers et al. | 435/69.1 |
| 5,401,658 A | 3/1995 | Fiers et al. | 435/252.33 |
| 5,460,811 A | 10/1995 | Goeddel et al. | 424/85.6 |
| 5,514,567 A | 5/1996 | Sugano et al. | 435/69.51 |

FOREIGN PATENT DOCUMENTS

| | | |
|---|---|---|
| BE | 882-545 | 9/1980 |
| BE | 887-397 | 6/1981 |
| DK | 1645 | 4/1981 |
| EP | 0 000 520 | 2/1979 |
| EP | 0 001 929 | 5/1979 |
| EP | 0 001 930 | 5/1979 |
| EP | 0 001 931 | 5/1979 |
| EP | 0 003 062 | 7/1979 |
| EP | 0 006 694 | 1/1980 |
| EP | 0 011 435 | 5/1980 |
| EP | 14050 | 8/1980 |
| EP | 0 018 218 | 10/1980 |
| EP | 26970 | 4/1981 |
| EP | 0 028 033 | 5/1981 |
| EP | 0 030 094 | 6/1981 |
| EP | 0 032 134 | 7/1981 |
| EP | 0 034 307 | 8/1981 |
| EP | 0 036 776 | 9/1981 |
| EP | 0 038 182 | 10/1981 |
| EP | 0 005 476 | 12/1981 |
| EP | 0 041 189 | 12/1981 |
| EP | 0 041 344 | 12/1981 |
| EP | 0 041 767 | 12/1981 |
| EP | 0 042 246 | 12/1981 |
| EP | 0 043 980 | 1/1982 |
| EP | 0 048 970 | 4/1982 |
| GB | 1521032 * | 8/1978 |

(Continued)

OTHER PUBLICATIONS

Borden, Annals of Internal Medicine 91: 472 (1979).*
C. Brack et al, "An analysis of the human interferon-α gene family" (preprint). Date unavailable.*
J. Tavernier et al, Evidence for a unique human fibroblast interferon (IFNβ1) chromosomal gene, devoid of intervening sequences, Laboratory of Molecular Biology (preprint). Date unavailable.*
J. Treuner et al, "Successful treatment of nasopharyngeal carcinoma with interferon" (preprint). Date unavailable.*

(Continued)

*Primary Examiner*—James Martinell
(74) *Attorney, Agent, or Firm*—Ropes & Gray LLP; James F. Haley, Jr.; Connie Wong

(57) ABSTRACT

DNA sequences, recombinant DNA molecules and hosts transformed with them which produce polypeptides displaying a biological or immunological activity of human fibroblast interferon, the genes coding for these polypeptides and methods of making and using these DNA sequences, molecules, hosts, genes and polypeptides. The DNA sequences are characterized by in that they code for a polypeptide displaying a biological or immunological activity of human fibroblast interferon. In appropriate hosts these DNA sequences and recombinant DNA molecules permit the production and identification of genes and polypeptides displaying a biological or immunological activity of human fibroblast interferon and their use in antiviral and antitumor or anitcancer agents.

3 Claims, 13 Drawing Sheets

FOREIGN PATENT DOCUMENTS

| GB | 2031434 | A |   | 4/1980 |
| --- | --- | --- | --- | --- |
| GB | 2031434 | A | * | 4/1980 |
| GB | 2037296 | A |   | 7/1980 |
| GB | 2037296 | A | * | 7/1980 |
| GB | 2055384 | A |   | 7/1980 |
| GB | 2039916 | A |   | 8/1980 |
| GB | 2052516 | A |   | 1/1981 |
| GB | 2079291 | A |   | 4/1981 |
| GB | 2061285 | A |   | 5/1981 |
| GB | 2063882 | A |   | 6/1981 |
| GB | 2068970 | A |   | 8/1981 |
| GB | 2069504 | A |   | 8/1981 |
| GB | 2071108 | A |   | 9/1981 |

OTHER PUBLICATIONS

A.G. Stewart et al, "The effects of priming with human fibroblast interferon on the induction of the mRNA for interferon and other proteins", Searle Research Laboratories (preprint). Date unavailable.*

Malik, "Biotechnology And Where It Is Going" (preprint) (Malik III).*

"The Production Of Interferon By 'Genetic Engineering'", *Research Disclosure*, No. 18309 (Jul. 1979).

*Abstracts. Conference On Regulatory Functions Of Interferons, N.Y. Acad. Sci.*, (Oct. 23-26, 1979).

G. Allen and K.H. Fantes, "A Family Of Structural Genes For Human Lymphoblastoid (Leukocyte-Type) Interferon", *Nature*, 287, pp. 408-411 (Oct. 2, 1980).

A.M. Arvin et al., "Interferon Prophylaxis For Simian Varicella Infection In Erythrocebus Patas Monkeys", *Abstracts*, 11th Annual UCLA Symposia, Supp. No. 6, No. 246 (1982).

H. Bernard et al., "Construction Of Plasmid Cloning Vehicles That Promote Gene Expression From The Bacteriophage Lambda $P_L$ Promoter", *Gene*, 5, 59-76 (1979).

W. Berthold et al., "Chemical Modifications Of Tyrosyl Residue(s) And Action Of Human-Fibroblast Interferon", *Eur. J. Biochem.*, 87, 367-370 (1978).

P. Beverley and D. Knight, "Killing Comes Naturally", *Nature*, 278, pp. 119-120 (1979).

A. Billiau et al., "Production, Purification And Properties Of Human Fibroblast Interferon", *Abstracts. Conference On Regulatory Functions Of Interferons, N.Y. Acad. Sci.*, nr. 29 (1979).

F. Bolivar et al., "Construction and Characterization Of New Cloning Vehicles. II. A Multipurpose Cloning System", *Gene*, 2, pp. 95-113 (1977).

H. Boyer and D. Rouland-Dussoix, "A Complementation Analysis of The Restriction And Modification Of DNA In *Escherichia coli*", *J Mol. Biol.*, 41, pp. 459-472 (1969).

C. Brack et al., "An Analysis Of The Human Interferon-β Gene Family" (preprint).

P.J. Bridgen et al., "Human Lymphoblastoid Interferon", *J. Biol. Chem.*, 252, No. 19, pp. 6585-6587.

C.J. Burrell et al., "Expression In *Escherichia coli* of Hepatitis B Virus DNA Sequences Cloned In Plasmid pBR322", *Nature*, 279, pp. 43-48 (1979).

R.L. Cavalieri et al., "Synthesis Of Human Interferon By *Xenopus laevis* Oocytes: Two Structural Genes For Interferons In Human Cells", *Proc. Nat'l. Acad. Sci. USA*, 74, pp. 3287-3291 (1977).

A.C.Y. Chang et al., "Phenotypic Expression In *E. coli* Of A DNA Sequence Coding For Mouse Dihydrofolate Reductase", *Nature*, 275, pp. 617-624 (1978).

A.A. Creasey et al., "The Role Of $G_O$-$G_1$ Arrest In The Inhibition Of Tumor Cell Growth By Interferon", *Abstracts. Conference On Regulatory Functions of Interferons. N.Y. Acad. Sci.*, nr. 17 (Oct. 23-26, 1979).

W. Degrave et al., "Nucleotide Sequence Of The Chromosomal Gene For Human Fibroblast ($β_1$) Interferon And Of The Flanking Regions", *Gene*, 14, pp. 137-143 (1981).

R. Derynck et al., "Isolation And Structure Of A Human Fibroblast Interferon Gene", *Nature*, 285, pp. 542-547 (1980) ("Derynck I").

R. Derynck et al., "Expression Of The Human Fibroblast Interfereon Gene In *Escherichia coli*", (1980) (preprint) ("Derynck II").

P.J. Farrell et al., "Interferon Action: Two Distinct Pathways For Inhibition Of Protein Synthesis By Double Stranded RNA", *Proc. Nat'l. Acad. Sci. USA*, 75, pp. 5893-5897 (1978).

J. Fujisawa et al., "Nonglycosylated Mouse L Cell Interferon Produced By The Action Of Tunicamycin", *J. Biol. Chem.*, 253, No. 24, pp. 8677-8679 (1978).

W. Gilbert and L. Villa-Komaroff, "Useful Proteins From Recombinant Bacteria", *Scientific American*, 242, pp. 74-94 (1980).

D.V. Goeddel et al., "Human Leukocyte Interferon Produced By *E. coli* Is Biologically Active", *Nature*, 287, pp. 411-416 (1980) ("Goeddel I").

D.V. Goeddel et al., "The Structure Of Eight Distinct Cloned uman Leukocyte Interferon cDNAs", *Nature*, 290, pp. 20-26 (1981) ("Goeddel II").

D.V. Goeddel et al., "Synthesis Of Human Fibroblast Interferon by *E.coli*", *Nucleic Acids Research*, 8, pp. 4057-4075 (1980) ("Goeddel III").

H. Gray et al., "Extracellular Nucleases Of Pseudomonas BAL 31. I. Characterization Of Single-Strand-Specific Deoxyribonuclease And Double-Strand Deoxyribonuclease Activities", *Nucleic Acids Res.*, 2, No. 9, pp. 1459-1492 (1975).

M. Grunstein and D.S. Hogness, "Colony Hybridization: A Method For The Isolation of Cloned DNAs That Contain A Specific Gene", *Proc. Natl. Acad. Sci. USA*, 72, No. 10, pp. 3961-3965 (1975).

E.A. Havell et al., "Altered Molecular Species Of Human Interferon Produced In The Presence Of Inhibitors Of Glycosylation", *J. Biol. Chem.*, 252, No. 12, pp. 4425-4427 (1977).

R.R. Herberman et al., "Augmentation By Interferon Of Human Natural And Antibody-Dependent Cell-Mediated Cytotoxicity", *Nature*, 277, pp. 221-223 (1979).

H.K. Hochkeppel et al., "Monoclonal Antibodies Against Human Fibroblast Interferon", *Nature*, 291, pp. 500-501 (1981).

M. Houghton et al., "The Amino-Terminal Sequences Of Human Fibroblast Interferon As Deduced From Reverse Transcripts Obtained Using Synthetic Oligonucleotide Primers", *Nucleic Acids Research*, 8, pp. 1913-1931 (1980).

M. Houghton, "Human Interferon Gene Sequences", *Nature*, 285, p. 536, (1980) ("Houghton I").

M. Houghton, "The Cloning And Expression Of A Human Fibroblast Interferon Gene In Bacteria", presented at Battele Conference, pp. 51-67 (Apr. 6-10, 1981) ("Houghton II").

A. Hovanessian and I.M. Kerr, "The (2'-5') Oligoadenylate (ppp A2'-5'A2'-5'A) Synthetase And Protein Kinase(s) From Interferon-Treated Cells", *Eur. J. Biochem.*, 93, pp. 515-526 (1979).

A. Hovanessian et al., "Synthesis Of Low Molecular Weight Inhibitor Of Protein Synthesis With Enzyme From Interferon-Treated Cells", *Nature*, 268, pp. 537-540 (1977).

A. Isaacs and J. Lindenmann, "Virus Interferon. I. The Interferon", *Proc Royal Soc.*, Series B, pp. 258-267 (1977) ("Isaacs I").

A. Isaacs and J. Lindenmann, "Virus Interferon. II. Some Properties Of Interferon", *Proc. Royal Soc.*, Series B, pp. 268-273 (1977) ("Issacs II").

I.M. Kerr and R.E. Brown, "ppp A2'ps'A2'p5'A: An Inhibitor Of Protein Synthesis Synthesized With An Enzyme Fraction From Interferon-Treated Cells", *Proc. Nat'l. Acad. Sci USA*, 75, pp. 256-260 (1978).

E. Knight, Jr., "Interferon: Purification And Initial Characterization From Human Diploid Cells", *Proc. Nat'l. Acad. Sci. USA*, 73, No. 2, pp. 520-523 (1976) ("Knight I").

E. Knight, Jr. et al., "Human Fibroblast Interferon: Amino Acid Analysis And Amino-Terminal Amino Acid Sequence", *Science*, 207, pp. 525-526 (1980) ("Knight II").

B. Lebleu et al., "Interferon, Double-Stranded RNA And Protein Phosphorylation", *Proc. Nat'l. Acad. Sci. USA*, 73, pp. 3107-3111 (1976).

L.S. Lin et al., "Purification Of Human Leukocyte Interferon To Apparent Homogeneity: Criteria For Purity", *Abstracts of The Annual Meeting*, No. S 202, p. 246 (1978).

V.S. Malik, "Recombinant DNA Technology", Advances In Applied Microbiology, 27, pp. 1-84 (1980) ("Malik I").

V.S. Malik, "Biotechnology Today" (preprint) (1980) ("Malik II").

V.S. Malik, "Biotechnology And Where It Is Going" (preprint) ("Malik III").

N. Mantei et al., "The Nucleotide Sequence Of A Cloned Human Leukocyte Interferon cDNA", *Gene*, 10, pp. 1-10 (1980).

M.G. Masucci et al., "Effect Of Interferon-α1 From *E.coli* On Some Cell Functions", *Science*, 209, pp. 1431-1435 (1980).

A.M. Maxam and W. Gilbert, "A New Method For Sequencing DNA", *Proc. Nat'l. Acad. Sci. USA*, 74, No. 2, pp. 560-564 (1977).

N.E. Murray et al., "Lambdoid Phages That Simplify The Recovery Of In Vitro Recombinants", *Mol. Gen. Genet.*, 150, pp. 53-61 (1977) ("Murray I").

N.E. Murray et al., "Molecular Cloning Of A The DNA Ligase Gene From Bacteriophage T4", *J. Mol. Biol.*, 132, pp. 493-505 (1979) ("Murray II").

S. Nagata et al., "Synthesis In *E. coli* Of A Polypeptide With Human Leukocyte Interferon Activity", *Nature*, 284, pp. 316-320 (1980) ("Nagata I").

S. Nagata et al., "The Structure Of One Of The Eight Or More Distinct Chromosomal Genes For Human Interferon-α", *Nature*, 287, pp. 401-408 (1980) ("Nagata II").

M. Pasek et al., "Hepatitis B Virus Genes And Their Expression In *E. coli*", *Nature*, 282, pp. 575-579 (1979).

M. Ptashne et al., "Autoregulation And Function Of A Repressor In Bacteriophage Lambda", *Science*, 194, pp. 156-161 (1976).

T.M. Roberts et al., "Synthesis Of Simian Virus 40t Antigen In *Escherichia coli*", *Proc. Nat'l. Acad. Sci. USA*, 76, pp. 5596-5600 (1979).

A. Rosenfeld, "Interferon: The Next Wonder Therapy?", *Life*, pp. 130-133 (1979).

M. Rubinstein et al., "Human Leukocyte Interferon: Production, Purification To Homogeneity, And Initial Characterization", *Proc. Nat'l. Acad. Sci. USA*, 76, pp. 640-644 (1979) ("Rubinstein I").

M. Rubinstein, "Human Leukocyte Interferon Purified To Homogeneity", *Science*, 202, pp. 1289-1290 (1978) ("Rubinstein II").

H. Schellekens et al., "In Vivo Immune Stimulation By Interferon During Viral Infection", *Antiviral Research*, 1, pp. 179-183 (1981).

A. Schmidt et al., "An Interferon-Induced Phosphodiesterase Degrading (2'-5') Oligoisoadenylate And The C-C-A Terminus Of tRNA", *Proc. Nat'l. Acad. Sci. USA*, 76, pp. 4788-4792 (1979).

P.B. Sehgal and A. D. Sagar, "Heterogeneity Of Poly(I)Poly(C)-Induced Human Fibroblast Interferon mRNA Species", *Nature*, 288, pp. 95-97 (1980).

D.L. Slate and F. H. Ruddle, "Fibroblast Interferon In Man Is Coded by Two Loci On Separate Chromosomes", *Cell*, 16, pp. 171-180 (1979).

A.G. Stewart et al., "The Effects Of Priming With Human Fibroblast Interferon On The Induction Of The mRNA For Interferon And Other Proteins", Searle Research Laboratories (preprint).

W.E. Stewart et al., "Comparisons Of Several Biological and Physiochemical Properties Of Human Leukocyte Interferons Produced By Human Leukocytes And By *E.coli*", *Gene*, 11, p. 181 (1980) ("Stewart I")—, Abstract only.

W.E. Stewart II et al., "Effect Of Glycosylation Inhibitors On The Production And Properties Of Human Leukocyte Interferon", *Virology*, 97, pp. 473-476 (1979) ("Stewart II").

M. Wiranowska-Stewart et al., "Contributions Of Carbohydrate Moieties To The Physical And Biological Properties Of Human Leukocyte, Lymphoblastoid and Fibroblast Interferons", *Abstracts Of The Annual Meeting 1978*, No. S 206; p. 247 (1978).

H. Strander and K. Cantrell, "Production Of Interferon By Human Leukocytes In Vitro", *Ann. Med. Exp. Fenn.*, 44, pp. 265-273 (1966).

M. Streuli et al., "At Least Three Human Type α Interferons: Structure of α 2", *Science*, 209, pp. 1343-1347 (1980).

J. Sutcliffe, "Complete Nucleotide Sequence Of The *Escherichia coli* Plasmid pBR322", *Cold Spring Harbor Symposium*, 49, pp. 77-90, (1979) ("Sutcliffe I").

J.G. Sutcliffe, "Nucleotide Sequence Of The Ampicillin Resistance Gene of *Escherichia coli* Plasmid pBR322", *Proc. Natl. Acad. Sci. USA*, 75, pp. 3737-3741 (1978) ("Sutcliffe II").

T. Taniguchi et al., "Construction And Identification Of A Bacterial Plasmid Containing The Human Fibroblast Interferon Gene Sequence", *Proc. Japan Acad.*, 55, Ser. B, pp. 464-469 (1979) ("Taniguchi I").

T. Taniguchi et al., "Human Leukocyte And Fibroblast Interferons Are Structurally Related", *Nature*, 285, pp. 547-549 (1980) ("Taniguchi II").

T. Taniguchi et al., "Molecular Cloning Of Human Interferon cDNA", *Proc. Nat'l. Acad. Sci. USA*, 77, pp. 4003-4006 (1980) ("Taniguchi III").

T. Taniguchi et al., "The Nucleotide Sequence of Human Fibroblast Interferon cDNA", *Gene*, 10, pp. 11-15 (1980) ("Taniguchi IV").

J. Tavernier et al., "Evidence For A Unique Human Fibroblast Interferon (IFN-$β_1$) Chromosomal Gene, Devoid Of Intervening Sequences", Laboratory of Molecular Biology (preprint).

J. Treuner et al., "Successful Treatment Of Nasopharyngeal Carcinoma With Interferon" (preprint).

L. Villa-Komaroff et al., "A Bacterial Clone Synthesizing Proinsulin", *Proc. Nat'l. Acad. Sci. USA*, 75, pp. 3727-3731 (1978).

R. Wagner, "Biological Studies Of Interferon", *Virology*, 13, pp. 323-337 (1961).

H. Weissbach et al., "In Vitro Synthesis Of Biologically Active Human Leukocyte Interferon Directed By Recombinant Plasmid DNA", *Archives of Biochemistry And Biophysics*, 210, pp. 417-419 (1981).

J. Weissenbach et al., "Identification Of The Translation Products Of Human Fibroblast Interferon mRNA In Reticulocyte Lysates", *Eur. J. Biochem.*, 98, pp. 1-8 (1979).

K.C. Zoon et al., "Purification And Partial Characterization Of Human Lymphoblastoid Interferon", *Proc. Nat'l. Acad. Sci. USA*, 76, pp. 5601-5605 (1979).

S. Bose et al., "Apparent Dispensability of the Carbohydrate Moiety Of Human Interferon for Antiviral Activity," *J. Biol. Chem.*, 251, pp. 1659-1662 (1976).

D.V. Goeddel et al., "Direct Expression in *Escherichia coli* of a DNA Sequence Coding for Human Growth Hormone," *Nature*, 281, pp. 544-558 (1979).

N. Stebbing et al., "Biological Comparison of Natural and Recombinant DNA-Derived Polypeptides," *Recombinant DNA Technical Bulletin*, 3, pp. 12-21 (1980).

Decision of the Board of Patent Appeals and Interferences, *Sugano v. Goeddel*, Interference 105,334, Paper No. 109 (Sep. 29, 2008).

Decision Of the Board of Patent Appeals and Interferences, *Sugano v. Goeddel*, Interference 105,337, Paper No. 112 (Sep. 29, 2008).

Brief of Appellants Goeddel et al., in *Goeddel v. Sugano*, Appeal Nos. 2009-1156 and 2009-1157 (Fed. Cir. Apr. 15, 2009).

Sugano Opposition to Fiers Response to Order to Show Cause, *Fiers v. Sugano*, Interference 105,661, Paper 39 (May 6, 2009) as well as the accompanying Sugano Exhibits 1001-1020.

Sugano Proposed Motions List, *Fiers v. Sugano*, Interference 105,661, Paper 62 (Jun. 30, 2009).

Decision On Order To Show Cause. *Fiers v. Sugano*, Interference 105,661, Paper 65 (Aug. 4, 2009).

\* cited by examiner

FIG. 4

```
                                                                          -20                                        -10
                                             MET-THR-ASN-LYS-CYS-LEU-LEU-GLN-ILE-ALA-LEU-LEU-
GCAA CCTTTCGAAG CCTTTGCTC  GGCACAACAG GTAGTAGGCG ACACTGTTCG TGTTGTTGAC ATG,ACC,AAC,AAG,TGT,CTC,CTC,CAA,ATT,GCT,CTC,CTG,100

-1 +1                                                     10                                                       20
LEU-CYS-PHE-SER-THR-THR-ALA-LEU-SER-MET-SER-TYR-ASN-LEU-GLY-PHE-LEU-LEU-GLN-ARG-SER-ASN-PHE-GLN-CYS-GLN-LYS-LEU-LEU-
TTG,TGC,TTC,TCC,ACT,ACA,GCT,CTT,TCC,ATG,AGC,TAC,AAC,TTG,CTT,GGA,TTC,CTA,CAA,AGA,AGC,AAT,TTT,CAG,TGT,CAG,AAG,CTC,CTG,190

30                                                      40                                                      50
TRP-GLN-LEU-ASN-GLY-ARG-LEU-GLU-TYR-CYS-LEU-LYS-ASP-ARG-MET-ASN-PHE-ASP-ILE-PRO-GLU-GLU-ILE-LYS-GLN-LEU-GLN-GLN-PHE-GLN-
TGG,CAA,TTG,AAT,GGG,AGG,CTT,GAA,TAC,TGC,CTC,AAG,GAC,AGG,ATG,AAC,TTT,GAC,ATC,CCT,GAG,GAG,ATT,AAG,CAG,CTG,CAG,CAG,TTC,CAG,280

60                                                     70                                                      80
LYS-GLU-ASP-ALA-ALA-LEU-THR-ILE-TYR-GLU-MET-LEU-GLN-ASN-ILE-PHE-ALA-ILE-PHE-ARG-GLN-ASP-SER-SER-THR-GLY-TRP-ASN-GLU-
AAG,GAG,GAC,GCC,GCA,TTG,ACC,ATC,TAT,GAG,ATG,CTC,CAG,AAC,ATC,TTT,GCT,ATT,TTC,AGA,CAA,GAT,TCA,TCT,AGC,ACT,GGC,TGG,AAT,GAG,370

90                                                      100                                                     110
THR-ILE-VAL-GLU-ASN-LEU-LEU-ALA-ASN-VAL-TYR-HIS-GLN-ILE-LEU-ASN-HIS-LEU-LYS-THR-VAL-LEU-GLU-GLU-LYS-LEU-GLU-LYS-GLU-ASP-PHE-
ACT,ATT,GTT,GAG,AAC,CTC,CTG,GCT,AAT,GTC,TAT,CAT,CAG,ATA,AAC,CAT,CTG,AAG,ACA,GTC,CTG,GAA,GAA,AAA,CTG,GAG,AAA,GAA,GAT,TTC,460

120                                                    130                                                     140
THR-ARG-GLY-LYS-LEU-MET-SER-SER-LEU-HIS-LEU-LYS-ARG-TYR-TYR-GLY-ARG-ILE-LEU-HIS-TYR-LEU-LYS-ALA-LYS-GLU-TYR-SER-HIS-CYS-
ACC,AGG,GGA,AAA,CTC,ATG,AGC,AGT,CTG,CAC,CTG,AAA,AGA,TAT,TAT,GGG,AGG,ATT,CTG,CAT,TAC,CTG,AAG,GCC,AAG,GAG,TAC,AGT,CAC,TGT,550

150                                                     160
ALA-TRP-THR-ILE-VAL-ARG-VAL-GLU-ILE-LEU-ARG-ASN-PHE-TYR-PHE-ILE-ASN-ARG-LEU-THR-GLY-TYR-LEU-ARG-ASN
GCC,TGG,ACC,ATA,GTC,AGA,GTG,GAA,ATC,CTA,AGG,AAC,TTT,TAC,TTC,ATT,AAC,AGA,CTT,ACA,GGT,TAC,CTC,CGA,AAC,TGA AGATCTCCTA GCCTG643

TGCCT CTGGGACTGG ACAATTGCTT CAAGCATTCT TCAACCAGCA GATGCTGTTT AAGTGACTGA TGGCTAATGT ACTGCATATG AAAGGACACT AGAAGATTTT GAAAT753

TTTTA TTAAATTATG AGTTATTTT ATTTATTTAA ATTTATTTT GGAAAATAAATAAATTATTTTGG TGCAAAAGTC AAAAAAAAA$_n$ ...
```

AMINO ACID COMPOSITION OF HUMAN FIBROBLAST INTERFERON

| AMINO ACID | COMPOSITION | | |
|---|---|---|---|
| | FROM DIRECT ANALYSIS BY TAN ET AL. | FROM DIRECT ANALYSIS BY KNIGHT ET AL. | DEDUCED FROM NUCLEOTIDE SEQUENCE |
| ASP | } 20.6 | 18.9 | 5 } 17 |
| ASN | | | 12 |
| THR | 8.0 | 6.8 | 7 |
| SER | 11.7 | 10.5 | 9 |
| GLU | } 27.5 | 27.0 | 13 } 24 |
| GLN | | | 11 |
| PRO | 4.4 | 2.7 | 1 |
| GLY | 5.4 | 7.8 | 6 |
| ALA | 9.3 | 10.0 | 6 |
| CYS | N.D. | 1.7 | 3 |
| VAL | 7.9 | 6.0 | 5 |
| MET | trace | 2.9 | 4 |
| ILE | 10.0 | 9.0 | 11 |
| LEU | 26.9 | 20.4 | 24 |
| TYR | 3.2 | 7.5 | 10 |
| PHE | 7.7 | 9.4 | 9 |
| HIS | 4.6 | 4.9 | 5 |
| LYS | 12.3 | 11.6 | 11 |
| ARG | 8.6 | 10.9 | 11 |
| TRP | 0.0 | 1.0 | 3 |
| TOTAL | 168 | 169 | 166 |

*FIG. 6*

DNA SEQUENCES, RECOMBINANT DNA MOLECULES AND PROCESSES FOR PRODUCING HUMAN FIBROBLAST INTERFERON-LIKE POLYPEPTIDES

This is a division of application Ser. No. 07/387,503, filed Jul. 28, 1989, which is a continuation of Ser. No. 06/250,609, filed Apr. 3, 1981, entitled DNA SEQUENCES, RECOMBINANT DNA MOLECULES AND PROCESSES FOR PRODUCING HUMAN FIBROBLAST INTERFERON-LIKE POLYPEPTIDES which are both abandoned.

TECHNICAL FIELD OF INVENTION

Although the RNA from VGS cells appeared to contain only one IFN-β-related mRNA fraction, RNA from other cell lines appears to contain at least another, and perhaps more, IFN-β-related mRNA fractions. This latter mRNA does not hybridize to the former mRNA but does code for a protein that displays IFN-β activity and is inactivated by antisera to authentic IFN-β. The cloning and expression of such mRNA and other mRNA's which are related to it by hybridization are also part of this invention because the processes hereinafter described are applicable thereto.

This invention relates to DNA sequences, recombinant DNA molecules and process for producing human fibroblast interferon-like polypeptides. More particularly, the invention relates to DNA sequences expressed in apropriate host organism. The recombinant DNA molecules disclosed herein are characterized by DNA sequences that code for polypeptides whose amino acid sequence and composition are substantially consistent with human fibroblast interferon and which have an immunological or biological activity of human fibroblast interferon. As will be appreciated from the disclosure to follow, the DNA sequences, recombinant DNA molecules and processes of this invention may be used in the production of polypeptides useful in antiviral and antitumor or anticancer agents and methods and in immunomodulation.

BACKGROUND ART

In this application the interferon nomenclature announced in *Nature*, 286, p. 2421 (Jul. 10, 1980) will be used. This nomenclature replaces that used in our earlier applications from which this application claims priority. E.g., IF is now designated IFN and fibroblast interferon is now designated IFN-β.

Two classes of interferons ("IFN") are known to exist. Interferons of Class I are small, acid stable (glyco)-proteins that render cells resistant to viral infection (A. Isaacs and J. Lindenmann, "Virus Interference I. The Interferon", *Proc. Royal Soc. Ser. B.*, 147, pp. 258-67 (1957) and W. E. Stewart, II, *The Interferon System*, Springer-Verlag (1979) (hereinafter "*The Interferon System*")). Class II IFNs are acid labile. At present, they are poorly characterized. Although to some extent cell specific (*The Interferon System*, pp. 135-45), IFNs are not virus specific. Instead, IFNs protect cells against a wide spectrum of viruses.

Human interferon ("HuIFN") has been classified into three groups α, β and γ. HuIFN-β or fibroblast interferon is produced upon appropriate induction in diploid fibroblast cells. It is also produced in minor amounts, together with a major amount of HuIFN-α, in lymphoblastoid cells. IFN-β made from these cells has been extensively purified and characterized (E. Knight, Jr., "Interferon: Purification And Initial Characterization From Human Diploid Cells", *Proc. Natl. Acad. Sci. USA*, 73, pp. 520-23 (1976)). It is a glyco-protein of about 20,000 molecular weight (M. Wiranowska-Stewart, et al., "Contributions Of Carbohydrate Moieties To The Physical And Biological Properties Of Human Leukocyte, Lymphoblastoid And Fibroblast Interferons", *Abst. Ann. Meeting Amer. Soc. Microbiol.*, p. 246 (1978)). It is also heterogeneous in regard to size presumably because of the carbohydrate moities.

The amino acid composition of authentic human fibroblast interferon has also been reported (E. Knight, Jr., et al., "Human Fibroblast Interferon: Amino Acid Analysis And Amino-Terminal Amino Acid Sequence", *Science*, 207, pp. 525-26 (1980)). And, elucidation of the amino acid sequence of authentic human fibroblast interferon is in progress. To date, the amino acid sequence of the $NH_2$ terminus of the authentic mature protein has been reported for the first 13 amino acid residues: Met-Ser-Tyr-Asn-Leu-Leu-Gly-Phe-Leu-Gln-Arg-Ser-Ser... (E. Knight, Jr., et al., supra).

Two distinct genes, one located on chromosome 2, the other on chromosome 5, have been reported to code for IFN-β (D. L. Slate and F. H. Ruddle, "Fibroblast Interferon In Man Is Coded By Two Loci On Separate Chromosomes", *Cell*, 16, pp. 171-80 (1979)). Other studies, however, indicate that the gene for IFN-β is located on chromosome 9 (A. Medger, et al., "Involvement Of A Gene On Chromosome 9 In Human Fibroblast Interferon Production", *Nature*, 280, pp. 493-95 (1979)).

Although authentic HuIFN-β is glycosylated, removal of the carbohydrate moiety (P. J. Bridgen, et al., "Human Lymphoblastoid Interferon", *J. Biol. Chem.*, 252, pp. 6585-87 (1977)) or synthesis of IFN-β in the presence of inhibitors which purport to preclude glycosylation (W. E. Stewart, II, et al., "Effect of Glycosylation Inhibitors On The Production And Properties Of Human Leukocyte Interferon", *Virology*, 97, pp. 473-76 (1979); J. Fujisawa, et al., "Nonglycosylated Mouse L Cell Interferon Produced By The Action Of Tunicamycin", *J. Biol. Chem.*, 253, pp. 8677-79 (1978); E. A. Havell, et al., "Altered Molecular Species Of Human Interferon Produced In The Presence Of Inhibitors of Glycosylation", *J. Biol. Chem.*, 252, pp. 4425-27 (1977); *The Interferon System*, p. 181) yields a smaller form of IFN-β which still retains most or all of its IFN activity.

HuIFN-β, like many human proteins, may also be polymorphic. Therefore, cells of particular individuals may produce IFN-β species within the more general IFN-β class which are physiologically similar but structurally slightly different from the prototype of the class of which it is a part. Therefore, while the protein structure of the IFN-β may be generally well-defined, particular individuals may produce IFN-βs that are slight variations thereof.

IFN-β is usually not detectable in normal or healthy cells (*The Interferon System*, pp. 55-57). Instead, the protein is produced as a result of the cell's exposure to an IFN inducer. IFN inducers are usually viruses but may also be non-viral in character, such as natural or synthetic double-stranded RNA, intracellular microbes, microbial products and various chemical agents. Numerous attempts have been made to take advantage of these non-viral inducers to render human cells resistant to viral infection (S. Baron and F. Dianzani (eds.), *Texas Reports On Biology And Medicine*, 35 ("Texas Reports"), pp. 528-40 (1977)). These attempts have not been very successful. Instead, use of exogenous HuIFN-β itself is now preferred.

Interferon therapy against viruses and tumors or cancers has been conducted at varying dosage regimes and under several modes of administration (The Interferon System, pp. 305-321). For example, interferon has been effectively administered orally, by innoculation—intravenous, intramuscular, intranasal, intradermal and subcutaneous—, and in the form of eye drops, ointments and sprays. It is usually administered one to three times daily in dosages of $10^4$ to $10^7$ units. The extent of the therapy depends on the patient and the condition being treated. For example, virus infections are usually treated by daily or twice daily doses over several days to two weeks and tumors and cancers are usually treated by daily or multiple daily doses over several months or years. The most effective therapy for a given patient must of course be determined by the attending physician, who will consider such well known factors as the course of the disease, previous therapy, and the patient's response to interferon in selecting a mode of administration and a dosage regime.

As an antiviral agent, HuIFN has been used to treat the following: respiratory infections (*Texas Reports*, pp. 486-96); herpes simplex keratitis (*Texas Reports*, pp. 497-500; R. Sundmacher, "Exogenous Interferon in Eye Diseases", *International Virology IV*, The Hague, Abstract nr. W2/11, p. 99 (1978)); acute hemorrhagic conjunctivitis (*Texas Reports*, pp. 501-10); adenovirus keratoconjunctivitis (A. Romano, et al., ISM Memo I-A8131 (October, 1979)); varicella zoster (*Texas Reports*, pp. 511-15); cytomegalovirus infection (*Texas Reports*, pp. 523-27); and hepatitis B (*Texas Reports*, pp. 516-22). See also *The Interferon System*, pp. 307-19. However, large-scale use of IFN as an antiviral agent requires larger amounts of IFN than heretofore have been available.

IFN has other effects in addition to its antiviral action. For example, it antagonizes the effect of colony stimulating factor, inhibits the growth of hemopoietic colony-forming cells and interferes with the normal differentiation of granulocyte and macrophage precursors (*Texas Reports*, pp. 343-49). It also inhibits erythroid differentiation in DMSO-treated Friend leukemia cells (*Texas Reports*, pp. 420-28). It is significant that some cell lines may be considerably more sensitive to HuIFN-β than to HuIFN-α in these regards (S. Einhorn and H. Strander, "Is Interferon Tissue-Specific?—Effect Of Human Leukocyte And Fibroblast Interferons On The Growth Of Lymphoblastoid And Osteosarcoma Cell Lines", *J. Gen. Virol.*, 35, pp. 573-77 (1977); T. Kuwata, et al., "Comparison Of The Suppression Of Cell And Virus Growth In Transformed Human Cells By Leukocyte And Fibroblast Interferon", *J. Gen. Virol.*, 43, pp. 435-39 (1979)).

IFN may also play a role in regulation of the immune response. For example, depending upon the dose and time of application in relation to antigen, IFN can be both immunopotentiating and immunosuppressive in vivo and in vitro (*Texas Reports*, pp. 357-69). In addition, specifically sensitized lymphocytes have been observed to produce IFN after contact with antigen. Such antigen-induced IFN could therefore be a regulator of the immune response, affecting both circulating antigen levels and expression of cellular immunity (*Texas Reports*, pp. 370-74). IFN is also known to enhance the activity of killer lymphocytes and antibody-dependent cell-mediated cytotoxicity (R. R. Herberman, et al., "Augmentation By Interferon Of Human Natural And Antibody-Dependent Cell-Mediated Cytotoxicity", *Nature*, 277, pp. 221-23 (1979); P. Beverley and D. Knight, "Killing Comes Naturally", *Nature*, 278, pp. 119-20 (1979); *Texas Reports*, pp. 375-80; J. R. Huddlestone, et al., "Induction And Kinetics Of Natural Killer Cells in Humans Following Interferon Therapy", *Nature*, 282, pp. 417-19 (1979); S. Einhorn, et al., "Interferon And Spontaneous Cytotoxicity In Man. II. Studies In Patients Receiving Exogenous Leukocyte Interferon", *Acta Med. Scand.*, 204, pp. 477-83 (1978)). Both may be directly or indirectly involved in the immunological attack on tumor cells.

Therefore, in addition to its use as an antiviral agent, HuIFN has potential application in antitumor and anticancer therapy (The Interferon System, pp. 319-21 and 394-99). It is now known that IFNs affect the growth of many classes of tumors in many animals (The Interferon System, pp. 292-304). They, like other anti-tumor agents, seem most effective when directed against small tumors. The antitumor effects of animal IFN are dependent on dosage and time but have been demonstrated at concentrations below toxic levels. Accordingly, numerous investigations and clinical trials have been and continue to be conducted into the antitumor and anticancer properties of HuIFNs. These include treatment of several malignant diseases such as osteosarcoma, acute myeloid leukemia, multiple myeloma and Hodgkin's disease (*Texas Reports*, pp. 429-35). In addition, HuIFN-β has recently been shown to cause local tumor regression when injected into subcutaneous tumoral nodules in melanoma and breast carcinoma-affected patients (T. Nemoto, et al., "Human Interferons And Intralesional Therapy Of Melanoma And Breast Carcinoma", *Amer. Assoc. For Cancer Research*, Abs nr. 993, p. 246 (1979)). Although the results of these clinical tests are encouraging, the antitumor and anticancer applications of IFN-β have been severely hampered by lack of an adequate supply of purified IFN-β.

Significantly some cell lines which resist the anticellular effects of IFN-α remain sensitive to IFN-β. This differential effect suggests that IFN-β may be usefully employed against certain classes of resistant tumor cells which appear under selective pressure in patients treated with high doses of IFN-α (T. Kuwata, et al., supra; A. A. Creasy, et al., "The Role of $G_0$-$G_1$ Arrest In The Inhibition Of Tumor Cell Growth By Interferon", Abstracts, Conference On Regulatory Functions Of Interferons, N.Y. Acad. Sci., nr. 17 (Oct. 23-26, 1979)).

At the biochemical level IFNs induce the formation of at least 3 proteins, a protein kinase (B. Lebleu, et al., "Interferon, Double-Stranded RNA And Protein Phosphorylation", *Proc. Natl. Acad. Sci. USA*, 73, pp. 3107-11 (1976); A. G. Hovanessian and I. M. Kerr, "The (2'-5') Oligoadenylate (ppp A2'-5A2'-5'A) Synthetase And Protein Kinase(s) From Interferon-Treated Cells", *Eur. J. Biochem.*, 93, pp. 515-26 (1979)), a (2'-5')oligo(A) polymerase (A. C. Hovanessian, et al., "Synthesis Of Low-Molecular Weight Inhibitor Of Protein Synthesis With Enzyme From Interferon-Treated Cells", *Nature*, 268, pp. 537-39 (1977); A. G. Hovanessian and I. M. Kerr, *Eur. J. Biochem*, supra) and a phosphodiesterase (A. Schmidt, et al., "An Interferon-Induced Phosphodiesterase Degrading (2'-5')oligoisoadenylate And The C-C-A Terminus Of tRNA", *Proc. Natl. Acad. Sci. USA*, 76, pp. 4788-92 (1979)).

Both IFN-β and IFN-α appear to trigger similar enzymatic pathways (C. Baglioni, "Interferon-Induced Enzymatic Activities And Their Role In The Antiviral State", *Cell*, 17, pp. 255-64 (1979)) and both may share a common active core because they both recognize a chromosome 21-coded cell receptor (M. Wiranowska-Stewart, "The Role Of Human Chromosome 21 In Sensitivity To Interferons", *J. Gen. Virol.*, 37, pp. 629-34 (1977)). The appearance of one or more of these enzymes in cells treated with IFN should allow a further characterization of proteins with IFN-like activity.

Today, HuIFN-β is produced by human cell lines grown in tissue culture. It is a low yield, expensive process. One large producer makes only 40-50×$10^8$ units of crude IFN-β per year (V. G. Edy, et al., "Human Interferon: Large Scale Production In Embryo Fibroblast Cultures", in *Human Interferon* (W. R. Stinebring and P. J. Chapple, eds.), Plenum Publishing Corp., pp. 55-60 (1978)). On purification by adsorption to controlled pore glass beads, IFN-β of specific activity of about $10^6$ units/mg may be recovered in 50% yield from the crude cell extracts (A. Billiau, et al., "Human Fibroblast Interferon For Clinical Trials: Production, Partial Purification And Characterization", *Antimicrobial Agents And Chemotherapy*, pp. 49-55 (1979)). Further purification to a specific activity of about $10^9$ units/mg is accomplished by zinc chelate affinity chromatography in about 100% yield (A. Billiau, et al., "Production, Purification And Properties Of Human Fibroblast Interferon", *Abstracts, Conference On Regulatory Functions Of Interferons*, N.Y. Acad. Sci., nr 29 (Oct. 23-26, 1979)). Because the specific activity of HuIFN-β is so high, the amount of IFN-β required for commercial applications is low. For example, 100 g of pure IFN-β would provide between 3 and 30 million doses.

Recent advances in molecular biology have made it possible to introduce the DNA coding for specific non-bacterial eukaryotic proteins into bacterial cells. In general, with DNA other than that prepared via chemical synthesis, the construction of such recombinant DNA molecules comprises the steps of producing a single-stranded DNA copy (cDNA) of a purified messenger RNA (mRNA) template for the desired protein; converting the cDNA to double-stranded DNA; linking the DNA to an appropriate site in an appropriate cloning vehicle to form a recombinant DNA molecule and transforming an appropriate host with that recombinant DNA molecule. Such transformation may permit the host to produce the desired protein. Several non-bacterial genes and proteins have been obtained in *E. coli* using recombinant DNA technology. These include, for example, IFN-α (S. Nagata, et al., "Synthesis In *E. coli* Of A Polypeptide With Human Leukocyte Interferon Activity", *Nature,* 284, pp. 316-20 (1980)). In addition, recombinant DNA technology has been employed to produce a plasmid said to contain a gene sequence coding for IFN-β (T. Taniguchi, et al., "Construction And Identification of A Bacterial Plasmid Containing The Human Fibroblast Interferon Gene Sequence", *Proc. Japan Acad. Ser. B,* 55, pp. 464-69 (1979)).

However, in neither of the foregoing has the actual gene sequence of IFN-β been described and in neither has that sequence been compared to the initial amino acid sequence or amino acid composition of authentic IFN-β. The former work is directed only to IFN-α, a distinct chemical, biological and immunological Class I interferon from IFN-β (cf. supra). The latter report is based solely on hybridization data. These data alone do not enable one to determine if the selected clone contains the complete or actual gene sequence coding for IFN-β or if the cloned gene sequence will be able to express IFN-β in bacteria. Hybridization only establishes that a particular DNA insert is to some extent homologous with and complementary to a mRNA component of the poly(A) RNA that induces interferon activity when injected into oocytes. Moreover, the extent of any homology is dependent on the hybridization conditions chosen for the screening process. Therefore, hybridization to a mRNA component of poly(A) RNA alone does not demonstrate that the selected DNA sequence is a sequence which codes for HuIFN-β or a polypeptide which displays the immunological or biological activity of HuIFN-β or that such sequence will be useful in producing such polypeptides in appropriate hosts.

At a seminar in Zurich on Feb. 25, 1980, Taniguchi stated that he had determined the nucleotide sequence for one of his hybridizing clones. He also stated that the first 13 amino acids coded for by that sequence were identical to that determined by Knight, et al., supra, for authentic HuIFN-β. Taniguchi did not disclose the full nucleotide sequence for his clone or compare its amino acid composition with that determined for authentic HuIFN-β. Taniguchi has since reported the full nucleotide sequence for his hybridizing clone (T. Taniguchi et al., *Gene,* 10, pp. 11-15 (1980)). The sequence differs by one nucleotide from that described and claimed in British patent application 8011306, filed Apr. 3, 1980, an application to which the present application claims priority. The amino acid sequence reported by Taniguchi is identical to the amino acid sequence described and claimed in the foregoing application 8011306. Taniguichi had also not reported the expression in an appropriate host of polypeptides which display an immunological or biological activity of HuIFN-β at the time of the filing of British patent application 80.18701, filed Jun. 6, 1980, an application to which this application claims priority. It is this expression in a host of polypeptide(s) displaying an immunological or biological activity of HuIFN-β and the methods, polypeptides, genes and recombinant DNA molecules thereof, which characterize this invention.

Nor is this invention addressed as is the apparent suggestion of Research Disclosure No. 18309, pp. 361-62 (1979) to prepare pure or substantially pure IFN-α mRNA before attempting to clone the IFN gene or to produce fibroblast interferon-like polypeptides in bacterial hosts.

Finally, it should be recognized that the selection of a DNA sequence or the construction of a recombinant DNA molecule which hybridizes to a mRNA from polyA RNA, that mRNA producing HuIFN activity in oocytes, is not sufficient to demonstrate that the DNA sequence or the hybrid insert of the recombinant DNA molecule corresponds to HuIFN. Instead, in the absence of a comparison of the amino acid sequence coded for by a particular DNA sequence and the amino acid sequence of the authentic protein, only the production of a polypeptide that displays an immunological or biological activity of HuIFN can actually demonstrate that the selected DNA sequence or constructed recombinant DNA molecule corresponds to HuIFN. More importantly, it is only after such HuIFN activity is shown that the DNA sequence, recombinant DNA molecule or sequences related to them may be usefully employed to select other sequences corresponding to HuIFN in accordance with this invention or to produce recombinant DNA molecules that may express products having an immunological or biological activity of HuIFN-β.

It will therefore be appreciated from the foregoing that the problem of producing HuIFN-β with the use of recombinant DNA technology is much different than any of the above described processes. Here, a particular DNA sequence of unknown structure—that coding for the expression of HuIFN-β in an appropriate host—must be found in and separated from a highly complex mixture of DNA sequences in order for it to be used in the production of HuIFN-β. Furthermore, this location and separation problem is exacerbated by the predicted exceedingly low concentration of the desired DNA sequence in the complex mixture and the lack of an effective means for rapidly analyzing the many DNA sequences of the mixture to select and separate the desired sequence.

DISCLOSURE OF THE INVENTION

The present invention solves the problems referred to by locating and separating DNA sequences that code for the expression of HuIFN-β in an appropriate host thereby providing DNA sequences, recombinant DNA molecule and methods by means of which a host is transferred to produce a polypeptide displaying an immunological or biological activity of human fibroblast interferon.

By virtue of this invention, it is possible to obtain polypeptides displaying an immunological or biological activity of HuIFN-β for use in antiviral, antitumor or anticancer agents and methods. This invention allows the production of these polypeptides in amounts and by methods hitherto not available.

As will be appreciated from the disclosure to follow, the DNA sequences and recombinant DNA molecules of the invention are capable of directing the production, in an appropriate host, of polypeptides displaying an immunological or biological activity of HuIFN-β. Replication of these DNA sequences and recombinant DNA molecules in an appropriate host also permits the production in large quantities of genes coding for these polypeptides. The molecular structure and properties of these polypeptides and genes may be readily determined. The polypeptides and genes are useful, either as produced in the host or after appropriate derivatization or modification, in compositions and methods for detecting and improving the production of these products themselves and for use in antiviral and antitumor or anticancer agents and methods and in immunomodulation.

This process is therefore distinguishable from the prior processes, above mentioned, in that this process, contrary to the noted prior processes, involves the preparation and selection of DNA sequences and recombinant DNA molecules which contain appropriate DNA sequences which code for at least one polypeptide displaying an immunological or biological activity of HuIFN-β.

It will be appreciated from the foregoing that a basic aspect of this invention is the provision of a DNA sequence which is characterized in that it codes for a polypeptide displaying an immunological or biological activity of HuIFN-β and is selected from the group consisting of the DNA inserts of G-pHFIF-1, G-pHFIF-3, G-pHFIF-6, G-pHFIF-7, G-pPla-HFIF-67-12, G-pPla-HFIF-67-12Δ19, G-pPla-HFIF-67-8, G-pPla-HFIF-67-12Δ279T, G-pPla-HFIF-67-12Δ218M1, G-pPla-HFIF-67-12ΔM1, G-pPla-HFIF-67-12Δ19BX-2, DNA sequences which hybridize to any of the foregoing DNA inserts, DNA sequences, from whatever source obtained, including natural, synthetic or semi-synthetic sources, related by mutation, including single or multiple, base substitutions, deletions, insertions and inversions to any of the foregoing DNA sequences or inserts, and DNA sequences comprising sequences of codons which on expression code for a polypeptide displaying similar immunological or biological activity to a polypeptide coded for on expression of the codons of any of the foregoing DNA sequences. The sequences of this invention are further characterized in that they permit the production of HuIFN-β and HuIFN-β-like polypeptides in hosts.

BRIEF DESCRIPTION OF THE DRAWINGS

FIG. 4 displays the composite nucleotide sequence of the coding strand of HuIFN-β DNA. The sequence is numbered from the beginning of the insert well into the untranslated area of the insert. Nucleotides 65-127 represent a signal sequence and nucleotides 128-625 represent the "mature" fibroblast interferon. The amino acid sequences of the signal polypeptide are depicted above their respective nucleotide sequences; the amino acids of the signal polypeptide being numbered from −21 to −1 and the amino acids of mature interferon being numbered from 1 to 166. Review of the restriction and fragment analysis data of the HuIFN-β DNA present in the cultures deposited in connection with Great Britain in patent application 80.11306, filed Apr. 3, 1980, has resulted in two nucleotides being changed in FIG. 4 as compared to FIG. 4 of that British patent application. These changes are in the untranslated sequence preceding the proposed signal sequence of HuIFN-β DNA. These changes do not effect the sequence of HuIFN-β DNA or the amino acid sequence of its translation product and do not alter the sequence's use as an hydridization probe to screen clones for HuIFN-β related DNA inserts.

FIG. 6 is a comparison of the amino acid composition of human fibroblast interferon as determined in accordance with this invention and that determined from authentic fibroblast interferon.

BEST MODE OF CARRYING OUT THE INVENTION

Figure 1:
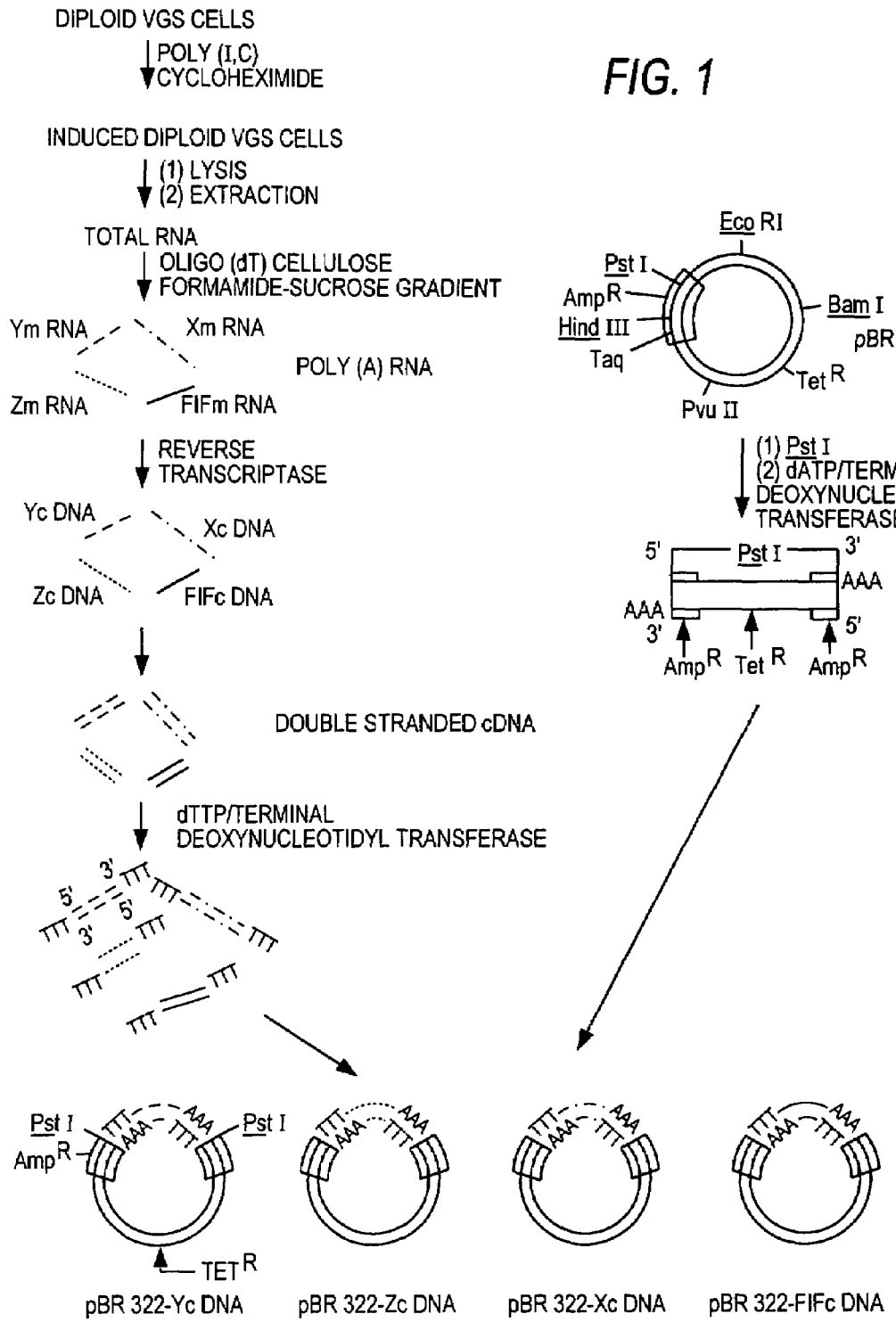
FIG. 1 is a schematic outline of one embodiment of a process of this invention for preparing a mixture of recombinant DNA molecules, some of which are characterized by inserted DNA sequences that code for the polypeptides of this invention.

In order that the invention herein described may be more fully understood, the following detailed description is set forth.

In the description the following terms are employed:

Nucleotide—A monomeric unit of DNA or RNA consisting of a sugar moiety (pentose), a phosphate, and a nitrogenous heterocyclic base. The base is linked to the sugar moiety via the glycosidic carbon (1' carbon of the pentose) and that combination of base and sugar is called a nucleoside. The base characterizes the nucleotide. The four DNA bases are adenine ("A"), guanine ("G"), cytosine ("C"), and thymine ("T"). The four bases are A, G, C and uracil ("U").

DNA Sequence—A linear array of nucleotides connected one to the other by phosphodiester bonds between the 3' and 5' carbons of adjacent pentoses.

Codon—A DNA sequence of three nucleotides (a triplet) which encodes through mRNA an amino acid, a translation start signal or a translation termination signal. For example, the nucleotide triplets TTA, TTG, CTT, CTC, CTA and CTG encode for the amino acid leucine ("Leu"), TAG, TAA and TGA are translation stop signals and ATG is a translation start signal.

Reading Frame—The grouping of codons during translation of mRNA into amino acid sequences. During translation the proper reading frame must be maintained. For example, the DNA sequence GCTGGTTGTAAG may be expressed in three reading frames or phases, each of which affords a different amino acid sequence:

GCT GGT TGT AAG—Ala-Gly-Cys-Lys

G CTG GTT GTA AG—Leu-Val-Val

GC TGG TTG TAA G—Trp-Leu-(STOP)

Polypeptide—A linear array of amino acids connected one to the other by peptide bonds between the α-amino and carboxy groups of adjacent amino acids.

Genome—The entire DNA of a cell or a virus. It includes inter alia the structural genes coding for the polypeptides of the substance, as well as operator, promoter and ribosome binding and interaction sequences, including sequences such as the Shine-Dalgarno sequences.

Structural Gene—A DNA sequence which encodes through its template or messenger RNA ("mRNA") a sequence of amino acids characteristic of a specific polypeptide.

Transcription—The process of producing mRNA from a structural gene.

Translation—The process of producing a polypeptide from mRNA.

Expression—The process undergone by a structural gene to produce a polypeptide. It is a combination of transcription and translation.

Plasmid—A nonchromosomal double-stranded DNA sequence comprising an intact "replicon" such that the plasmid is replicated in a host cell. When the plasmid is placed within a unicellular organism, the characteristics of that organism may be changed or transformed as a result of the DNA of the plasmid. For example, a plasmid carrying the gene for tetracycline resistance ($Tet^R$) transforms a cell previously sensitive to tetracycline into one which is resistant to it. A cell transformed by a plasmid is called a "transformant".

Phage or Sacteriophage—Bacterial virus many of which consist of DNA sequences encapsidated in a protein envelope or coat ("capsid").

Cloning Vehicle—A plasmid, phage DNA or other DNA sequence which is able to replicate in a host cell, characterized by one or a small number of endonuclease recognition sites at which such DNA sequences may be cut in a determinable fashion without attendant loss of an essential biological function of the DNA, e.g., replication, production of coat proteins or loss of promoter or binding sites, and which contain a marker suitable for use in the identification of transformed cells, e.g., tetracycline resistance or ampicillin resistance. A cloning vehicle is often called a vector.

Cloning—The process of obtaining a population of organisms or DNA sequences derived from one such organism or sequence by asexual reproduction.

Recombinant DNA Molecule or Hybrid DNA—A molecule consisting of segments of DNA from different genomes which have been joined end-to-end outside of living cells and have the capacity to infect some host cell and be maintained therein.

Expression Control Sequence—A sequence of nucleotides that controls and regulates expression of structural genes when operatively linked to those genes. They include the lac system, major operator and promoter regions of phage λ, the control region of fd coat protein and other sequences known to control the expression of genes of prokaryotic or eukaryotic cells and their viruses.

Referring now to FIG. 1, we have shown therein a schematic outline of one embodiment of a process for preparing a mixture of recombinant DNA molecules, some of which include inserted DNA sequences that characterize this invention.

PREPARATION OF POLY(A)RNA CONTAINING HUMAN FIBROBLAST INTERFERON mRNA (IFN-β mRNA)

The RNA used in this invention was extracted from human VGS cells, a diploid fibroblast cell line which can be propagated in monolayer cultures at 37° C. IFN-β is produced in these cells on induction with poly(I,C) in the presence of cycloheximide.

For a typical RNA isolation, each of 20 roller bottles of diploid VGS cells in confluent monolayer was "primed" overnight with 100 units/ml IFN-β and the cultures induced for 1 h with 100 μg/ml poly(I,C) and 50 μg/ml cycloheximide, incubated with cycloheximide (50 μg/ml) for 4 h, harvested by scraping into phosphate-buffered saline and spun down. The cells were lysed for 15 min at 0° C. to remove the intact nuclei containing the DNA and to isolate the cytoplasmic RNA by suspending them in hypotonic buffer (10 mM Tris-HCl (pH 7.4), 10 mM NaCl and 1.5 mM $MgCl_2$) and adding NP40 to 1%. Nuclei were removed by pelleting in a Sorvall SS-34 rotor for 5 min at 3000 rpm. Sodium dodecyl sulphate ("SDS") and EDTA were added to the supernatant to 1% and 10 mM, respectively, and the mixture extracted 5 times with 2× vol of 1:1 redistilled phenol and chloroform-isoamyl alcohol (25:1), the aqueous phases containing the RNA being separated by centrifugation in a Sorvall SS-34 rotor at 8000 rpm for 10 min after each extraction. The RNA was precipitated from the aqueous phase by addition of 1/10 vol of 2 M sodium acetate (pH 5.1) and 2.5 vol ethanol. Usually, 60 to 90 μg of total cytoplasmic RNA were obtained per roller bottle.

Other procedures to extract the cytoplasmic RNA have also been used. For example, the cells were totally lysed after homogenization in 0.2 M Tris-HCl (pH 9.0), 50 mM NaCl, 20 mM EDTA and 0.5% SDS and extracted with phenol-chloroform as above (F. H. Reynolds, et al., "Interferon Activity Produced By Translation Of Human Interferon Messenger RNA In Cell-Free Ribosomal Systems And In Xenopus Oocytes", *Proc. Natl. Acad. Sci. USA,* 72, pp. 4881-87 (1975)) or the washed cells were suspended in 400 μl 0.1 M NaCl, 0.01 M Tris-HCl (pH 7.5), and 0.001 M EDTA ("NTE buffer") and 2.5 ml 4 M guanidinium-isothiocyanate and 1 M β-mercaptoethanol in 20 mM sodium acetate (pH 5.0) were added and the cells homogenized. The lysate was layered on a 1.3-ml 5.7 M CsCl cushion in a Beckman SW-60 Ti nitrocellulose tube, spun for 17 h at 39000 rpm to pellet the RNA and separate it from DNA, proteins and lipids and the RNA extracted once with phenol-chloroform (J. Morser, et al., "Characterization Of Interferon Messenger RNA From Human Lymphoblastoid Cells", *J. Gen. Virol.,* 44, pp. 231-34 (1979)).

The total RNA was assayed for the presence of IFN-β mRNA by injection into the cytoplasm of *Xenopus laevis* oocytes and determination of the IFN-β activity induced therein (Reynold, et al., supra). The assay was conducted by dissolving the RNA in water and injecting about 50 ml into each oocyte. The oocytes were incubated overnight at room temperture in Barth medium (J. Gurdon, *J. Embryol. Exper. Morphol.,* 20, pp. 401-14 (1968)), homogenized in part of the medium, the debris removed by centrifugation, and the IFN-β activity of the supernatant determined. Detection of IFN-β activity was by reduction of virus-induced cytopathic effect (W. E. Stewart and S. E. Sulkin, "Interferon Production In Hampsters Experimentally Infected With Rabies Virus", Proc. Soc. Exp. Biol. Med., 123, pp. 650-53 (1966)). The challenge virus was vesicular stomatitis virus (Indiana strain) and the cells were human diploid fibroblasts trisomic for chromosome 21 to afford higher IFN-β sensitivity. IFN-β activity is expressed relative to the IFN reference standard 69/19.

Poly(A) RNA containing IFN-β mRNA was isolated from the cytoplasmic RNA by adsorption to oligo(dT)-cellulose (type 7; P-L Biochemicals) in 0.4 M NaCl, 10 mM Tris-HCl (pH 7.8), 10 mM EDTA and 0.2% SDS for 10 min at room temperature. RNA aggregation was minimized by heating the RNA for 2 min at 70° C. prior to adsorption. After washing the cellulose with the above-mentioned buffer, the poly(A) RNA fraction was eluted with 10 mM Tris-HCl (pH 7.8), 1 mM EDTA and 0.2% SDS. It usually comprised 4-5% of the total RNA, as measured by optical density at 260 nm.

A further purification to enrich the poly(A)RNA in IFN-β mRNA was effected by formamide-sucrose gradients (T. Pawson, et al., "The Size of Rous Sarcoma Virus mRNAs Active In Cell-Free Translation", Nature, 268, pp. 416-20 (1977)). These gradients gave much higher resolution than non-denaturing sucrose gradients. Usually about 80 μg poly (A) RNA was dissolved in 50% formamide, 100 mM LiCl, 5 mM EDTA, 0.2% SDS and 10 mM Tris-HCl (pH 7.4), heated at 37° C. for 2 min to prevent aggregation and loaded on a 5-20% sucrose gradient in a Beckman SW-60 Ti polyallomer tube. After centrifugation at 20° C. for 4½ h at 60000 rpm in the Beckman SW-60 Ti rotor with total $^{14}$C-labeled eukaryotic RNA serving as size markers, the gradient was fractionated and the optical density of the fractions determined. All RNA fractions were precipitated twice with 0.5 M NaCl and 2.5 vol ethanol and assayed for interferon mRNA activity as described above. These purification processes result in about a 40-fold enrichment in the IFN-β mRNA content of the poly(a) RNA.

Alternatively, the oligo(dT)-adsorbed mRNA (60 μg) was fractionated by electrophoresis in a 4% polyacrylamide gel in 7 M urea, 0.1% SDS, 50 mM Tris-borate (pH 8.3), and 1 mM EDTA, the mRNA being dissolved in this buffer and heated 1 min at 55° C. before application to the gel. After electrophoresis, sections of 2 mm width were cut from the gel and the RNA eluted from each homogenized gel section, further freed from impurities by adsorption to oligo(dT)-cellulose and assayed for IFN-β mRNA as before.

At this point it should be recognized that even the poly(A) RNA product obtained from the formamide-sucrose gradients and the polyacrylamide gel fractionation contains a very large number of different mRNA's. Except for the mRNA specific for IFN-β, the other mRNAs are undesirable contaminants (FIG. 1). Unfortunately, these contaminant RNAs behave similarly to HuIFN-β mRNA throughout the remainder of the cloning process of this invention. Therefore, their presence in the poly(A) RNA will result in the ultimate preparation of a large number of unwanted bacterial clones which contain genes that may code for polypeptides other than IFN-β. This contamination presents complex screening problems in the isolation of the desired IFN-β hybrid clones. In the case of IFN-β, the screening problem is further exacerbated by the lack of a sufficiently purified sample of HuIFN-β mRNA or DNA or portion thereof to act as a screening probe for the identification of the desired clones. Therefore, the screening process for the IFN-β clones is very time-consuming and difficult. Further, because only a very small percentage of IFN-β clones themselves are expected to express IFN-β in a biologically or immunologically active form, the isolation of an active clone is a "needle in a haystack" screening process.

Advantageously, we may use recombinant DNA technology to provide a purified sample of HuIFN-β mRNA or cDNA or a portion thereof. This purified mRNA or cDNA can then be used to screen rapidly very large numbers of bacterial clones and thereby markedly increase the probability of isolating a clone which expresses IFN-β in an active form.

SYNTHESIS OF DOUBLE-STRANDED cDNA CONTAINING IFN-β cDNA

Poly(A) RNA enriched in IFN-β mRNA was used as a template to prepare complementary DNA ("cDNA"), essentially as described by R. Devos, et al., "Construction And Characterization Of A Plasmid Containing A Nearly Full-Size DNA Copy Of Bacteriophage MS2 RNA", J. Mol. Biol., 128, pp. 595-619 (1979) for the construction of a plasmid containing a DNA copy of bacteriophage MS2 RNA.

Single-stranded cDNA was prepared from the poly(A) RNA by RNA-dependent DNA polymerase (25 units) from avian myeloblastosis virus ("AMV") reverse transcriptase (a gift from Dr. J. Beard, Life Sciences, Gulfport, Fla.), initiated by a $(dT)_{10}$ primer (6 μg, Miles) hybridized to the poly(A) tail of the RNA, in 50 μl 50 mM Tris-HCl (pH 8.3), 10 mM $MgCl_2$, 30 mM β-mercaptoethanol, 4 mM $Na_4P_2O_7$, 2.5 μg/μl inactivated bovine serum albumin, dTTP, dATP, dCTP and dGTP, each at 0.5 mM and $\alpha$-$^{32}$P-dATP (20 μCi, Amersham). After 30 min at 41° C., the reaction was terminated by the addition of EDTA to 10 mM, the reaction mixture extracted with equal vol of phenol:chloroform:isoamyl alcohol (25:24:1) and the aqueous phase layered on a Sephadex G50 column and eluted in TE buffer (10 mM Tris-HCl (pH 7.5) 1 mM EDTA). The void fractions displaying radioactivity were precipitated by the addition of 10 μg E. coli transfer RNA, potassium acetate (pH 5.1) to 0.2 M and 2.5 vol ethanol.

The cDNA population synthesized above is in fact a complex mixture of cDNAs originating from the different mRNAs which were present in the enriched poly(A) mRNA (FIG. 1). In addition, because of premature termination by AMV reverse transcriptase, many of the cDNAs are incomplete copies of the various mRNAs in the poly(A) RNA (not shown in FIG. 1).

Before rendering the cDNA double-stranded, it is removed from its association to the complementary template RNA by precipitation with ethanol and incubation in TE buffer (10 mM Tris-HCl (pH 7.5), 1 mM EDTA) with ribonuclease $T_1$ (10 units, Sankyo Co., Ltd) and pancreatic ribonuclease A (10 μg, Sigma) to 10 μl for 30 min at 37° C. (the ribonucleases being free of single-strand-specific endo- and exo-deoxyribonucleases). The removal of the template strand by ribonuclease instead of with alkali avoids possible cDNA mutation by alkali-catalyzed deamination.

The cDNA strand may be rendered double-stranded by DNA polymerase I (A. Efstratiadis, et al., "Enzymatic In Vitro Synthesis Of Globin Genes", Cell, 7, pp. 279-88 (1976)). The 10 μl ribonuclease/cDNA mixture from above was diluted to 20 μl with $MgCl_2$ to 10 mM, DTT to 10 mM, potassium phosphate (pH 6.9) to 100 mM, dATP, dCTP, dTTP, and dGTP each to 0.3 mM, $\alpha$-$^{32}$P-dATP (20 μCi, Amersham) and DNA polymerase I (40 units, Biolabs). After 6 h at 15° C., EDTA to 10 mM and SDS to 0.1% were added and the double-stranded cDNA isolated by extraction (phenol:chloroform:isoamyl alcohol), chromatography (Sephadex G50) and precipitation of void fractions as before.

To open the single-stranded hairpin loop which remains on the double stranded cDNA structure, the precipitated cDNA was dissolved in 100 μl 0.2 M NaCl, 50 mM sodium acetate (pH 4.5), 10 mM zinc acetate and 2 μg heat-denatured calf thymus DNA and reacted with S1 nuclease (5 units, Sigma) for 30 min at 37° C. Addition of EDTA to 10 mM, extraction with phenol:chloroform:isoamyl alcohol and precipitation of the aqueous phase by the addition of 10 μg *E. coli* transfer RNA as carrier, 0.2 M sodium acetate (pH 5.1) and 2.5 vol ethanol yielded a blunt-ended double stranded cDNA mixture. This mixture is heterogeneous both as a consequence of the heterogeneity of the poly(A) RNA used as a template to prepare it (FIG. 1) and of the premature termination of the cDNA transcripts by the AMV reverse transcriptase (not shown in FIG. 1).

To lessen the effect of the latter heterogeneity, the double stranded cDNA was sized by electrophoresis on a 4% polyacrylamide gel in 50 mM Tris-borate buffer (pH 8.3) and 1 mM EDTA, 5'-$^{32}$P-labelled restriction fragments (φX174 (RF)-DNA) serving as size markers. DNA bands of appropriate size (e.g., size classes 800-900 bp, 700-800 bp, 650-700 bp and 550-650 bp) were selected. Because the double-stranded cDNA prepared from the polyacrylamide gel electrophoresed poly(A) RNA displayed a prominent band about 850 bp, this band was considered to represent the full-length DNA. The bands were eluted by crushing the gel in 0.5 M ammonium acetate and 0.1% SDS and stirring overnight. After the debris had been removed by centrifugation, the DNA was adsorbed to hydroxylapatite powder, loaded on a Sephadex G50 column in 5 mM sodium phosphate (pH 7.5), washed extensively with buffer, eluted with 0.45 M sodium phosphate (pH 7.5) and immediately desalted by the sieving effect of the Sephadex G50 matrix. The fractions containing the eluted DNA, as monitored by the $^{32}$P-radioactivity, were precipitated by the addition of 10 μg *E. coli* transfer RNA, sodium acetate to 0.2 M and 2.5 vol ethanol.

The efficiency of the cDNA preparation, described above, is exemplified by a typical experiment where about 2 μg poly(A) RNA after formamide-sucrose gradient yielded about 16 ng double-stranded cDNA having a size range of 800 to 900 bp.

Again, it must be recognized that this double-stranded cDNA is a mixture of a large number of cDNAs, only a very few of which are IFN-β cDNA (FIG. 1).

CLONING OF DOUBLE-STRANDED DNA

A wide variety of host/cloning vehicle combinations may be employed in cloning the double-stranded cDNA prepared in accordance with this invention. For example, useful cloning vehicles may consist of segments of chromosomal, non-chromosomal and synthetic DNA sequences, such as various known derivatives of SV40 and known bacterial plasmids, e.g., plasmids from *E. coli* including col E1, pCR1, pBR322, pMB9 and their derivatives, wider host range plasmids, e.g., RP4,phage DNAs, e.g., the numerous derivatives of phage λ, e.g., NM 989, and other DNA phages, e.g., M13 and *Filamenteous* single stranded DNA phages and vectors derived from combinations of plasmids and phage DNAs such as plasmids which have been modified to employ phage DNA or other expression control sequences or yeast plasmids such as the 2 μ plasmid or derivatives thereof. Useful hosts may include bacterial hosts such as *E. coli* HB 101, *E. coli* X1776, *E. coli* X2282, *E. coli* MRCI and strains of *Pseudomonas, Bacillus subtilis, Bacillus stearothermophilus* and other bacilli, yeasts and other fungi, animal or plant hosts such as animal (including human) or plant cells in culture or other hosts. Of course, not all host/vector combinations may be equally efficient. The particular selection of host/cloning vehicle combination may be made by those of skill in the art after due consideration of the principles set forth without departing from the scope of this invention.

Furthermore, within each specific cloning vehicle, various sites may be selected for insertion of the double-stranded DNA. These sites are usually designated by the restriction endonuclease which cuts them. For example, in pBR322 the PstI site is located in the gene for β-lactamase, between the nucleotide triplets that code for amino acids 181 and 182 of that protein. This site was initially employed by S. Nagata et al., supra, in their synthesis of polypeptides displaying an immunological or biological activity of IFN-α. One of the two HindII endonuclease recognition sites is between the triplets coding for amino acids 101 and 102 and one of the several Taq sites at the triplet coding for amino acid 45 of β-lactamase in pBR322. In similar fashion, the EcoRI site and the PvuII site in this plasmid lie outside of any coding region, the EcoRI site being located between the genes coding for resistance to tetracycline and ampicillin, respectively. This site was employed by T. Taniguchi et al., supra, in their recombinant synthetic scheme. These sites are well recognized by those of skill in the art. It is, of course, to be understood that a cloning vehicle useful in this invention need not have a restriction endonuclease site for insertion of the chosen DNA fragment. Instead, the vehicle could be joined to the fragment by alternative means.

The vector or cloning vehicle and in particular the site chosen therein for attachment of a selected DNA fragment to form a recombinant DNA molecule is determined by a variety of factors, e.g., number of sites susceptible to a particular restriction enzyme, size of the protein to be expressed, susceptibility of the desired protein to proteolytic degradation by host cell enzymes, contamination or binding of the protein to be expressed by host cell proteins difficult to remove during purification, expression characteristics, such as the location of start and stop codons relative to the vector sequences, and other factors recognized by those of skill in the art. The choice of a vector and an insertion site for a particular gene is determined by a balance of these factors, not all selections being equally effective for a given case.

Although several methods are known in the art for inserting foreign DNA into a cloning vehicle or vector to form a recombinant DNA molecule, the method preferred for initial cloning in accordance with this invention is digesting the plasmid (in particular pBR322) with that restriction enzyme specific to the site chosen for the insertion (in particular PstI) and adding dA tails to the 3' termini by terminal transferase. In similar fashion, the double-stranded cDNA is elongated by the addition of dT tails to the 3' termini to allow joining to the tailed plasmid. The tailed plasmid and cDNA are then annealed to insert the cDNA in the appropriate site of the plasmid and to circularize the hybrid DNA, the complementary character of the tails permitting their cohesion (FIG. 1). The resulting recombinant DNA molecule now carries an inserted gene at the chosen PstI restriction site (FIG. 1). This method of dA-dT tailing for insertion is described by D. A. Jackson, et al., "Biochemical Methods For Inserting New Genetic Information Into DNA Of Simian Virus 40: Circular SV40 DNA Molecules Containing Lambda Phage Genes And The Galactose Operon Of *Escherichia coli*", Proc. Natl. Acad. Sci. USA, 69, pp. 2904-909 (1972) and R. Devos, et al., supra. It results in about 3 times as many recombinant DNA plasmids as dG-dC tailing.

Of course, other known methods of inserting DNA sequences into cloning vehicles to form recombinant DNA molecules are equally useful in this invention. These include, for example, dG-dC tailing, direct ligation, synthetic linkers, exonuclease and polymerase-linked repair reactions followed by ligation, or extension of the DNA strand with DNA polymerase and an appropriate single-stranded template followed by ligation.

It should, of course, be understood that the nucleotide sequences or cDNA fragments inserted at the selected site of the cloning vehicle may include nucleotides which are not part of the actual structural gene for the desired polypeptide or may include only a fragment of the complete structural gene for the desired protein. It is only required that whatever DNA sequence is inserted, a transformed host will produce a polypeptide having a biological or immunological activity of HuIFN-β or that the DNA sequence itself is of use as a hybridization probe to select clones which contain DNA sequences useful in the production of polypeptides having an immunological or biological activity of HuIFN-β.

The cloning vehicle or vector containing the foreign gene is employed to transform a host so as to permit that host to express polypeptides displaying an immunological or biological activity of HuIFN-β for which the hybrid gene codes. The selection of an appropriate host is also controlled by a number of factors recognized by the art. These include, for example, compatibility with the chosen vector, toxicity of proteins encoded by the hybrid plasmid, ease of recovery of the desired protein, expression characteristics, bio-safety and costs. A balance of these factors must be struck with the understanding that not all hosts may be equally effective for expression of a particular recombinant DNA molecule.

In the present synthesis, the preferred initial cloning vehicle is the bacterial plasmid pBR322 and the preferred initial restriction endonuclease site therein is the PstI site (FIG. 1). The plasmid is a small (molecular weight approx. 2.6 megadaltons) plasmid carrying resistance genes to the antibiotics ampicillin (Amp) and tetracycline (Tet). The plasmid has been fully characterized (F. Bolivar, et al., "Construction And Characterization Of New Cloning Vehicles II. A Multi-Purpose Cloning System", *Gene*, pp. 95-113 (1977); J. C. Sutcliffe, "pBR322 Restriction Map Derived From The DNA Sequence: Accurate DNA Size Markers Up To 4361 Nucleotide Pairs Long", *Nucleic Acids Research,* 5, pp. 2721-28 (1978); J. G. Sutcliffe, "Complete Nucleotide Sequence Of The *Escherichia coli* Plasmid pBR322", Cold Spring Harbor Symposium, 43, I, pp. 77-90 (1978)). Insertion of the DNA product in this site provides a large number of bacterial clones each of which contains one of the DNA genes or fragments thereof present in the cDNA product previously prepared. Again, only a very few of these clones will contain the gene for IFN-β or fragments thereof (FIG. 1) and none of them may permit the expression of polypeptides displaying an immunological or biological activity of IFN-β. The preferred initial host in accordance with this invention is *E. coli* HB 101.

1. Preparation of PstI-Cleaved, dA-elongated pBR322

Plasmid pBR322 was digested completely at 37° C. with PstI endonuclease (New England Biolabs) in 10 mM Tris-HCl (pH 7.6), 7 mM MgCl$_2$, 7 mM 2-mercaptoethanol. The mixture was extracted with 1 vol phenol and 10 vol ether and precipitated with 2.5 vol ethanol:0.2 M sodium acetate solution.

Addition of homopolymeric dA tails (FIG. 1) by terminal deoxynucleotidyl transferase (TdT) (purified according to L. Chang and F. J. Bollum, "Deoxynucleotide-Polymerizing Enzymes Of Calf Thymus Gland", *J. Biol. Chem.,* 246, pp. 909-16 (1971)) was done in a 50-μl reaction volume containing 0.14 M potassium cacodylate, 30 mM Tris-HCl (pH 6.8), 1 mM CoSO$_4$, 0.2 μg/μl heat-inactivated bovine serum albumin, 0.8 mM DTT, 0.2 mM dATP and some α-$^{32}$P-dATP. Incubation was at 37° C. for 5 min before EDTA was added to 10 mM and SDS to 0.1% and the mixture extracted with phenol and chromatographed on Sephadex G50 in TE buffer. The void fractions, containing the linearized and elongated pBR322, were further purified by adsorption in 10 mM Tris-HCl (pH 7.8), 1 mM EDTA and 0.4 M NaCl to oligo(dT) cellulose. After extensive washing, the desired fractions were eluted with 10 mM Tris-HCl (pH 7.8) and 1 mM EDTA.

2. Preparation of dT-elongated DNA

Double-stranded DNA was elongated with dTMP residues in similar fashion to that described above for dA tailing of pBR322, except that dTTP and some $^3$H-dTTP replaced the dATP and α-$^{32}$P-ATP. Purification on oligo(dT) cellulose was, of course, omitted. As before, the dT-elongated DNA is a mixture of different species, only a very few of which are HuIFN-β-related (FIG. 1).

3. Preparation of Ca$^{++}$-Treated *E. coli* HB101

Ca$^{++}$-treated *E. coli* HB101 was prepared by the method of E. M. Lederberg and S. N. Cohen, "Transformation Of *Salmonella Typhimurium* By Plasmid Deoxyribonucleic Acid", *J. Bacteriol.,* 119, pp. 1072-74 (1974) by inoculating the *E. coli* HB101 (a gift from H. Boyer) into 5 ml LB medium (10 parts bactotryptone, 5 parts yeast extract and 5 parts NaCl per liter) and cultures grown overnight at 37° C. The fresh cultures were diluted 1/100 in 20 ml LB medium and grown to a density of about 2×10$^8$ bacteria per ml, quickly chilled in ice and pelleted at 6000 rpm for 5 min in a Sorvall SS34 rotor at 4° C. The cells, kept at 0-4° C., were washed with 20 ml 100 mM CaCl$_2$. After 20 min in ice, the cells were repelleted and resuspended in 2 ml 100 mM CaCl$_2$ and maintained at 0° C. for 15 min. Aliquots (200 μl), supplemented with glycerol to 11%, could be stored for several months at −80° C. without loss of activity (D. A. Morrison, "Transformation In *Escherichia coli*: Cryogenic Preservation Of Competent Cells", *J. Bacteriol.,* 132, pp. 349-51 (1977)).

4. Annealing of da-elongated pBR322 and dT-elongated DNA

The vector's and DNA insert's complementary dA-and dT-tails permit annealing to form the initially desired hybrid plasmid or recombinant DNA molecule. For this purpose, the dA-tailed PstI-cleaved pBR322 vector and the mixture of sized dT-tailed cDNAs were dissolved in TSE buffer (10 mM Tris-HCl (pH 7.6), 1 mM EDTA, 100 mM NaCl) to 1.5 μg/ml plasmid and to a molar ratio of plasmid to DNA insert of 1.5 to 2.0. After heating to 65° C. for 10 min, the mixture was cooled slowly to room temperature over 4 h.

The product is, of course, a large mixture of different recombinant DNA molecules and some cloning vehicles without inserted DNA sequences. However, each recombinant DNA molecule contains a cDNA segment at the PstI site. Each such cDNA segment may comprise a gene or a fragment thereof. Only a very few of the cDNA fragments code for HuIFN-β or a portion thereof (FIG. 1). The vast majority code for one of the other proteins or portions thereof whose mRNAs were part of the poly(A) RNA used in the process of this invention (FIG. 1). It should also be understood that none of the clones of the above-prepared library may permit the expression of polypeptides displaying an immunological or biological activity of IFN-β.

5. Transfection Of *E. coli* HB101 With The Annealed Hybrid Plasmids

P3 containment facilities were used as necessary for the transfection process and all subsequent steps in which the resulting transformed bacteria were handled. Aliquots (90 μl or less) of the above mixture were cooled to 0° C. and 1 M CaCl$_2$ added to 0.1 M. Aliquots (100 μl or less) of this solution were added to 200 μl Ca$^{++}$-treated *E. coli* HB101 in ice and after standing at 0° C. for 30 min, the cells were heat-shocked for 5 min at 37° C. and cooled again at 0° C. for 15 min. After addition of 2 ml LB-medium, the cells were incubated at 37° C. in a shaking water bath for 30 to 45 min and the bacterial suspension plated out onto 1.2% agar plates, containing LB medium supplemented with 10 µg/ml tetracycline.

Since plasmid pBR322 includes the gene for tetracycline resistance, *E. coli* hosts which have been transformed with a plasmid having that gene intact will grow in cultures containing that antibiotic to the exclusion of those bacteria not so transformed. Therefore, growth in tetracycline-containing culture permits selection of hosts transformed with a recombinant DNA molecule or recyclized vector.

After 24 h at 37° C., individual colonies were picked and suspended in 100 µl LB medium (supplemented as above) in the wells of microtiter plates (Dynatech). After incubation at 37° C. overnight, 11 µl dimethyl-sulfoxide were mixed into each well and the trays sealed with adhesive tape. The plates were stored at 31 20° C. and a library of 17,000 individual clones of transformed *E. coli* HB101 was prepared. This library was derived from 270 fmoles (128 ng) dT-tailed cDNA inserts, which in turn were synthesized from 4.4 µg gradient purified poly(A) RNA. About 98% of the clones of this library were sensitive to carbenicillin (a more stable ampicillin derivative). Therefore, about 98% of the library contained a plasmid having an insert in the PstI-site of the β-lactamase gene of pBR322 and only about 2% contained a recircularized vector without insert.

Figure 2:
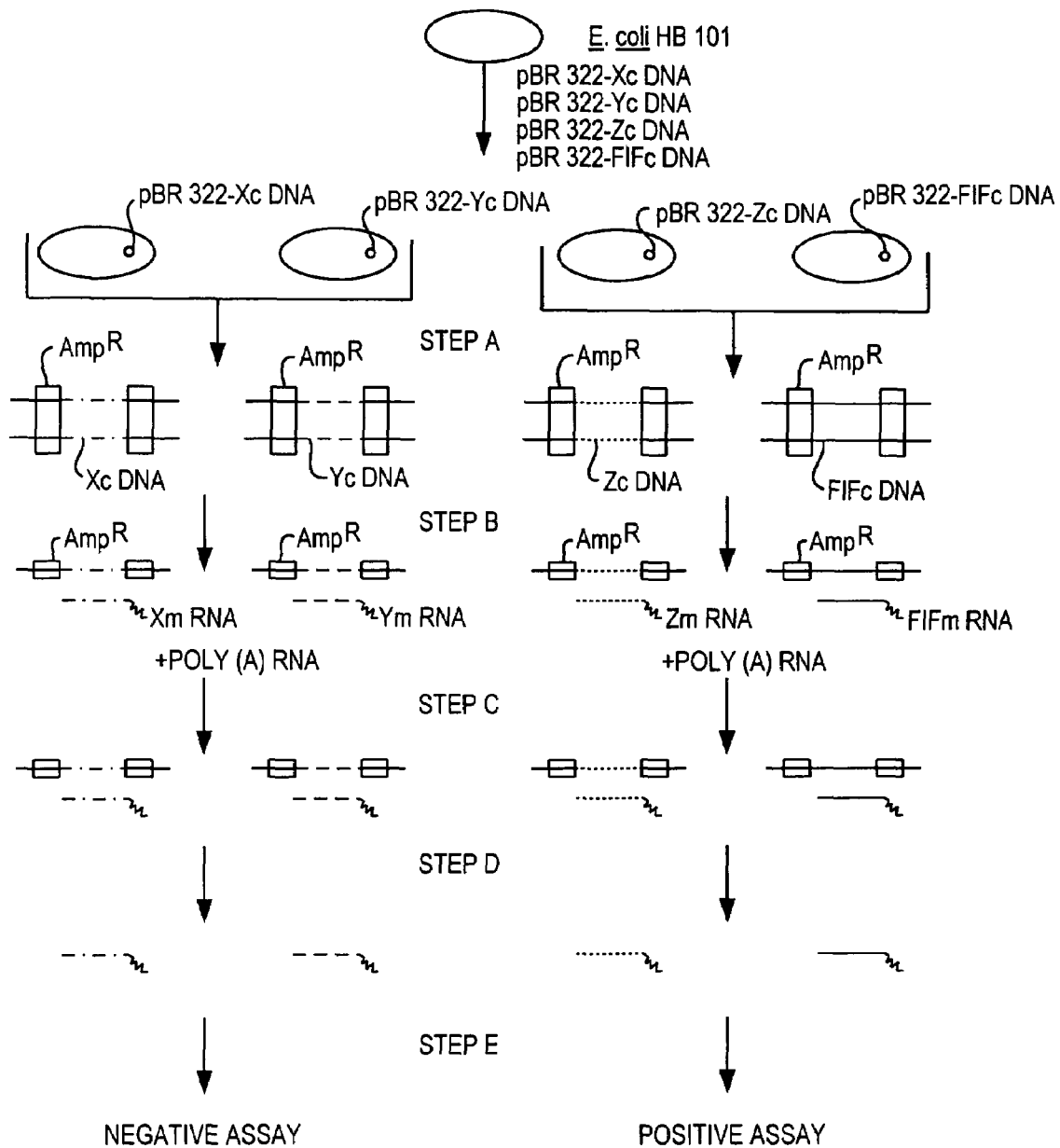
FIG. 2 is a schematic outline of the initial clone screening process of this invention.
Figure 3:
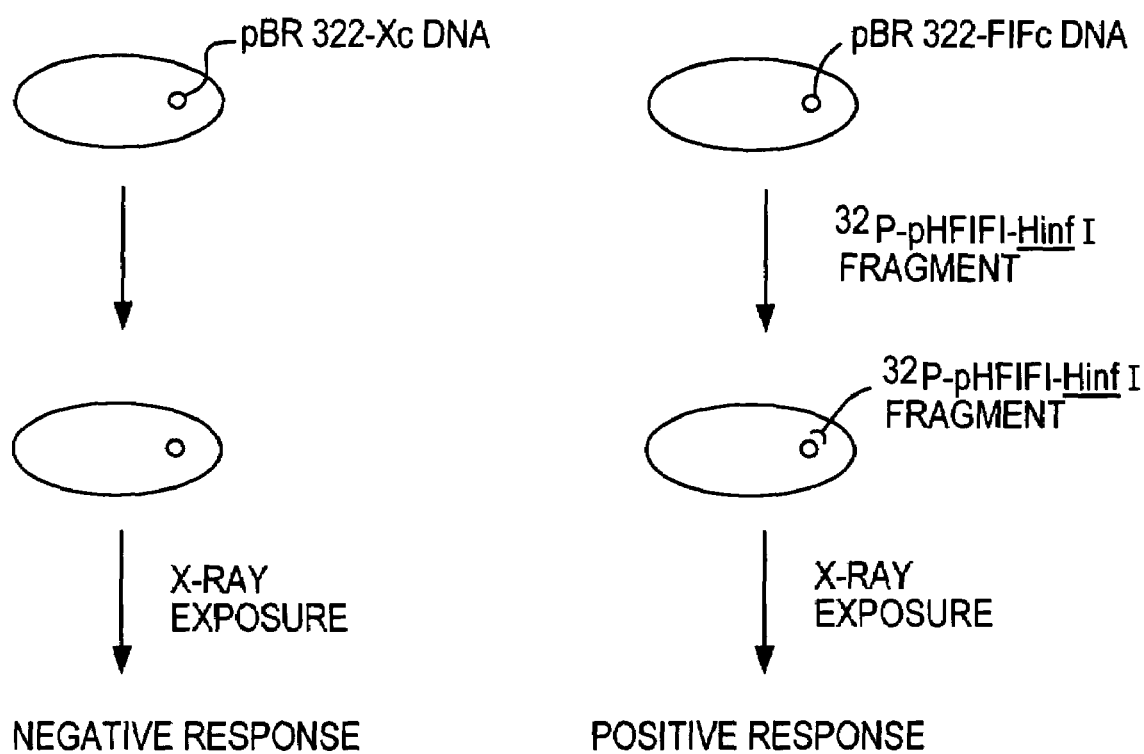
FIG. 3 is a schematic outline of one embodiment of a clone screening process using DNA sequences prepared in accordance with the invention.

These 17,000 clones contain a variety of recombinant DNA molecules representing complete or partial copies of the mixture of mRNAs in the poly(A) RNA preparation from HuIFN-β-producing cells (FIG. 2). The majority of these will contain only a single recombinant DNA molecule. Only a very few of these recombinant DNA molecules are related to HuIFN-β. Accordingly, the clones must be screened to separate the HuIFN-β-related clones from the others.

SCREENING FOR A CLONE CONTAINING HuIFN-β cDNA

There are several approaches to screen for bacterial clones containing HuIFN-βcDNA. These include, for example, RNA selection hybridization (Alwine, et al., infra), differential hybridization (T. P. St. John and R. W. Davis, "Isolation Of Galactose-Inducible DNA Sequences From *Saccharomyces Cerevisiae* By Differential Plaque Filter Hybridization", *Cell*, 16, pp. 443-452 (1979)); hybridization with a synthetic probe (B. Noyes, et al., "Detection And Partial Sequence Analysis Of Gastrin mRNA By Using An Oligodeoxynucleotide Probe", *Proc. Natl. Acad. Sci. USA*, 76, pp. 1770-74 (1979)) or screening for clones that produce the desired protein by immunological (L. Villa-Komaroff, et al., "A Bacterial Clone Synthesizing Proinsulin", *Proc. Natl. Acad. Sci. USA*, 75, pp. 3727-31 (1978)) or biological (A. C. Y. Chang, et al., "Phenotypic Expression In *E. coli* Of A DNA Sequence Coding For Mouse Dihydrofolate Reductase", *Nature*, 275, pp. 617-24 (1978)) assays. We have chosen RNA selection hybridization as being the most convenient and promising method for primary screening.

A. RNA Selection Hybridization Assay
1. Overview Of The Initial Assay
Referring now to FIG. 2, the recombinant DNA molecules were isolated from individual cultures of about 46 clones sensitive to carbenicillin and resistant to tetracycline from the above library of clones (two mixtures of 2 clones shown in FIG. 2) (Step A). The recombinant DNA molecules were cleaved and hybridized to total RNA containing HuIFN-β mRNA prepared as before (Step B). All recombinant DNA molecule-total RNA hybrids were separated from the non-hybridized total RNA (Step C). The hybridized total RNA was recovered from the hybrids and purified (Step D). The recovered RNA was assayed for HuIFN-β mRNA activity as above (Step E). If, and only if, the mixture of recombinant DNA molecules contains a recombinant DNA molecule having an inserted nucleotide sequence capable of hybridizing to the HuIFN-β mRNA in the total RNA, under stringent hybridization conditions, will the mRNA released from that hybrid cause the formation of HuIFN-β in oocytes, because mRNA released from any other recombinant DNA molecule-total RNA hybrid will not be IFN-β-related. If a group of 46 clones gave a positive response, the clones were regrouped into 6 subgroups (4 subgroups of 8 and 2 subgroups of 7) and each subgroup assayed as before. This process was continued until a single clone responding to this assay was identified.

There is no assurance that the recombinant DNA molecules and bacterial cultures transformed therewith, which are thus identified, contain the complete IFN-β cDNA sequence or even that the DNA sequence actually codes for IFN-β or will permit the clone to express polypeptides displaying an immunological or biological activity of IFN-β. However, the recombinant DNA molecules will certainly contain extensive nucleotide sequences complementary to the IFN-β mRNA coding sequence. Therefore, the recombinant DNA molecule may at least be used as a source of a probe to screen rapidly other recombinant DNA molecules and clones transformed with them to identify further sets of clones which may contain an authentic or complete IFN-β nucleotide coding sequence. These clones may then be analyzed for possible expression of polypeptides displaying a biological or immunological activity of IFN-β. And, the nucleotide sequence of the inserted DNA fragment of these hybrid plasmids and its amino acid translation product may be determined and correlated, if possible, to the amino acid composition and initial sequence reported for authentic IFN-β (supra).

2. Execution Of The Initial Assay
Step A—Preparation Of The Recombinant DNA Molecule Mixture Replicas of a microtiter plate containing 96 clones from the above library of clones were made on LB-agar plates, one containing 10 µg/ml tetracycline and the other supplemented with 100 µg/ml carbenicillin. In this manner, two sets of about 45-46 clones, resistant to tetracycline and sensitive to carbenicillin, were picked and grown separately overnight at 37° C. in 100 ml LB medium, containing 10 µg/ml tetracycline. These cultures were pooled, spun down in a Sorvall GS-3 rotor at 8000 rpm for 10 min, washed twice with TES buffer (50 mM Tris-HCl (pH 8), 5 mM EDTA, 5 mM NaCl) and resuspended in 40 ml TES per 1 of initial culture volume. The cells were lysed with lysozyme-Triton X-100 (M. Kahn, et al., "Plasmid Cloning Vehicles Derived From Plasmids Col El, F, R6K And RK2" in *Methods In Enzymology*, 68: Recombinant DNA (R. Wu, ed.) (1980) (in press)). Forty ml of the TES suspended cells were combined with 20 ml 10% sucrose in 50 mM Tris-HCl (pH 8) and lysozyme to 1.3 mg/ml and allowed to stand at room temperature for 20 min. To this suspension were added 1 ml 0.5 M EDTA-NaOH (pH 8), 8 ml 0.2% Triton X-100, 25 mM EDTA, 50 mM Tris-HCl (pH 8) and the lysis completed at room temperature for 30 min. Cellular debris and most of the chromosomal DNA were removed by pelleting in a Beckman SW27 rotor at 24000 rpm for 45 min. The supernatant was cooled in ice, combined with ⅓ vol 40% polyethylene glycol 6000-2 M NaCl and allowed to stand overnight at 0° C. The resulting precipitate was collected in a Sorvall HB4 rotor at 5000 rpm for 10 min at 4° C. and dissolved in TES buffer. The solution, with 0.2 vol 10 mg/ml ethidium bromide (Serva) and CsCl to 1 g/ml, was centrifuged in a Beckmann R60 Ti-rotor at 40000 rpm for at least 48 h, one polyallomer tube usually being sufficient for the lysate from 1-2 l of original culture volume. Two DNA bands could be visualized in the tube under UV-illumination. The band of highest density corresponds to plasmid form I DNA, the second band corresponds to form II and form III plasmid DNAs and some chromosomal DNA. The first band was collected from the tube, ethidium bromide removed by six isoamyl alcohol extractions, and the aqueous phase diluted with 3 vol water-supplemented with up to 0.2 M sodium acetate (pH 5.1) before DNA precipitation with 2.5 vol ethanol. The DNA was redissolved, extracted with phenol and again precipitated with ethanol. The quality of the DNA was monitored by electrophoresis on a 1% agarose gel in 40 mM Tris-HOAc (pH 7.8), 20 mM sodium acetate, 2 mM EDTA, followed by ethidium bromide staining. If the DNA was contaminated with too much RNA, it was further purified by neutral sucrose-gradient centrifugation: 300 µg DNA in 10 mM Tris-HCl (pH 7.6) and 1 mM EDTA were loaded on a 36-ml 5-20% sucrose gradient in 10 mM Tris-HCl (pH 7.6), 1 mM EDTA, 1 M NaCl, centrifuged in polyallomer tubes for 16 h at 24000 rpm in a Beckmann SW27 rotor at 18° C. and the DNA containing fractions ($OD_{260}$) pooled and precipitated with sodium acetate-ethanol.

Step B—Hybridization Of The DNA With Total RNA

About 150 µg DNA, thus prepared, were combined with some uniformly labelled $^{32}$P-marker DNA and 2 µg pSTNV-1 DNA (a recombinant plasmid containing a full size cDNA copy of satellite tobacco necrosis virus ("STNV")-RNA; J. Van Emmelo, et al., "Construction And Characterization Of A Plasmid Containing A Nearly Full-Size DNA Copy Of Satellite Tobacco Necrosis Virus RNA", *J. Mol. Biol.*, (in press) as internal control, sheared by sonication in an MSE sonicator and precipitated with sodium acetate-ethanol.

A diazobenzyloxymethyl (DBM)-cellulose solid matrix (Cf., J. C. Alwine, et al., "Method For Detection Of Specific RNAs In Agarose Gels By Transfer To Diazobenzyl Oxymethyl Paper And Hybridizing With DNA Probes", *Proc. Natl. Acad. Sci. USA*, 74, pp. 5350-54 (1977)) was prepared according to the method of J. C. Alwine, et al., "Detection Of Specific RNAs Or Specific Fragments Of DNA Fractionation In Gels And Transfer To Diazobenzyloxymethyl Paper", Methods-Enzymology, 68:Recombinant DNA (R. Wu, ed.) (1980). For a paper matrix, a sheet of Whatman 540 paper was evenly soaked in a solution containing 2-3 mg 1-(m-nitrobenzyloxy)methyl pyridinium chloride (NBPC/BDH and 0.7 ml sodium acetate trihydrate in 28.5 µl water per $cm^2$, incubated at 60° C. until dry and for further 10 min, and baked at 130-135° C. for 30-40 min. After washing several times with water (about 20 min), 3 times with acetone (about 20 min), and drying it was stored. The paper was incubated at 60° C. for 30 min in 0.4 ml 20% sodium dithionite-water per $cm^2$ with occasional shaking. The paper was again washed four times with water, once with 30% acetic acid for 5 min and four times with water, transferred to 0.3 ml per $cm^2$ ice-cold 1.2 M HCl to which 10 mg/ml fresh $NaNO_2$ had been added immediately before use for 30 min at 0° C., and washed twice quickly with ice-cold water and once with 80% dimethyl sulfoxide (spectrophotometric grade, Merck)-20% 25 mM sodium phosphate (pH 6.0). For a powder matrix essentially the same procedure was followed using microgranular cellulose powder (Whatman CC31), the quantities being expressed against the corresponding weight of the cellulose matrix.

Initially, we used a powder matrix because the capacity for binding was higher, so relatively smaller volumes for hybridization, washes and elution could be used. Subsequently, we used a paper matrix for individual clone screening. Use of paper permits efficient elution with water which proved superior for the later assay of IFN-βmRNA.

The DNA prepared above was dissolved in 25 mM sodium phosphate (pH 6.0) heated for 1 min, chilled and four vol DMSO added. Coupling to the matrix (50 mg (powder) or a paper disc (10 mm dia.)) usually proceeded over a weekend at 4° C. with continuous mixing. The volume of the DNA was kept rather small to allow close contact with the matrix and thereby enhance efficient coupling of the DNA to the matrix. After coupling, the matrix was washed four times with water and four times with 0.4 N NaOH at 37° C. for 10 min each, again four times with water at room temperature and finally twice with hybridization buffer (50% formamide (deionized, Baker), 40 mM piperazine-N,N'-bis(2-ethane sulfonic acid) (pH 6.4) ("PIPES, Sigma), 1 mM EDTA, 0.6 M NaCl and 0.1% SDS) at 4° C. Coupling efficiencies were measured by $^{32}$P-radioactivity.

Twenty µg total RNA, prepared as before, and 50 ng STNV-RNA were dissolved in 250 µl (50 µl for paper matrix) hybridization buffer and added to the DNA coupled matrix. The matrix was heated to 70° C. for 2 min and held at 37° C. overnight with gentle mixing.

Step C—Separation Of Hybridized Total RNA-DNA From Non-Hybridized Total RNA

After centrifugation of the powder matrix, the unhybridized RNAs were removed and the matrix washed seven times with a total 2 ml 50% formamide, 10 mM PIPES (pH 6.4), 1 mM EDTA, 0.3 M NaCl and 0.1% SDS, the lower salt content of these washes destabilizing non-specific RNA-DNA binding. Each wash was followed by centrifugation and resuspension of the matrix in the buffer. For subsequent assay, the first wash was pooled with the unhybridized RNA ("Fraction 1") and washes 2-4 ("Fraction 2") and washes 5-7 ("Fraction 3") were pooled. In hybridizations to a paper matrix, a similar procedure was utilized except that the total wash volume was limited 1 ml.

Step D—Purification Of Hybridized Total RNA

The hybridized total RNA-DNA was eluted from a powder matrix with 3 elutions of a total 900 µl 99% formamide, 0.2% SDS at 70° C. for 2 min and chilled in ice. The total hybridization procedure and elution with formamide were essentially as described by A. G. Smith (personal communication). The hybridized total RNA-DNA was eluted from a paper matrix by first washing with 100 µl of ice cold water and following that with two water elutions (total 300 µl) at 80° C. for 2 min. For subsequent assay these elutions and the 100 µpl wash were pooled ("Fraction 4").

To one-half of each of the 4 fractions, 0.1 µg calf liver tRNA or ribosomal RNA were added (Fractions 1A, 2A, 3A and 4A) and to the other half 8 µg eukaryotic poly(A) RNA or ribosomal RNA were added (Fractions 1B, 2B, 3B, 4B). The fractions were purified by precipitation by the addition of 0.5 M NaCl and 2.5 vol ethanol to removal traces of formamide and other impurities.

Step E—Determination Of IFN-β mRNA Activity

Fractions 1A, 2A, 3A and 4A were translated in 25 µl nuclease-treated rabbit reticulocyte lysate (prepared according to the procedure of R. B. Pelham and R. J. Jackson, "An Efficient mRNA-Dependent Translation System For Reticulocyte Lysates", *Eur. J. Biochem.*, 7, pp. 247-56 (1976)) by the procedure of B. LeBleu, et al., "Translation Of Mouse Interferon mRNA In *Xenopus Laevis* Oocytes And In Rabbit Reticulocyte Lysates", *Biochem. Biophys. Res. Commun.*, 82, pp. 665-673 (1978) except that 250 mM spermidine-HCl, 1 mM fructose-1,6-diphosphate were added in the presence of $^{35}$S-methionine (0.5 mCi/ml, Amersham). After incubation, 25 µl reticulocyte lysate, from above, were combined with 1 µl 10% deoxycholate-10% Triton X100 and 2 µl antiserum-PBS (1:9) and heated at 37° C. for 1 h. Twenty µl *Staphylococcus aureus* Cowan I (freshly washed, S. W. Kessler, et al., "Rapid Isolation Of Antigens From Cells With A Staphylococcal Protein A-Antibody Adsorbent: Parameters Of The Interaction Of Antibody-Antigen Complexes With Protein A", *J. Immunology*, 115, pp. 1617-1624 (1975)) in 10% 100 mM NaCl, 10 mM Tris-HCl (pH 7.4), 1 mM EDTA, 0.05% NP40 were added and the mixture maintained at 20° C. for 30 min and centrifuged in an Eppendorf 5412 centrifuge for 2 min. The pellet was washed and centrifuged twice with PBS and the final pellet dissolved in sample buffer and electrophoresed on a 13% polyacrylamide gel as described by U. K. Laemmli, et al., "Cleavage Of Structural Proteins During The Assembly Of The Head Of Bacteriophage T4", *Nature*, 227, pp. 680-85 (1970), and autoradiographed. Comparison of the STNV-RNA translation products in Fractions 1A and 4A provide an indication of the efficiency of hybridization and RNA degradation in the process.

Fractions 1B, 2B, 3B and 4B were dissolved in 2 μl water and assayed in oocytes for IFN-β mRNA content as described above.

3. Subsequent Assay—Hybridization To Nitrocellulose Sheets

Some subsequent assays of individual clones were done on nitrocellulose sheets (M. Cochet, et al., "Cloning Of An Almost Full-Length Chicken Conalbumin Double-Stranded cDNA", *Nucleic Acids Research,* 6, pp. 2435-2452 (1979)). The DNA was dissolved in 2 M NaCl and 0.2 M NaOH, heated at 100° C. for 1 min, chilled, and spotted on detergent free Millipore filters (pore size 0.45 um; 7 mm dia.). The filters were baked for 2 h at 80° C., washed in 0.3 M NaCl, 2 mM EDTA, 0.1% SDS, 10 mM Tris-HCl (pH 7.5) and dried at room temperature. The RNA was hybridized for 3 h at 47° C. in 30% formamide, 0.5 M NaCl, 0.4% SDS, 2 mM EDTA, 50 mM PIPES (pH 7.5). Hybridization was stopped by dilution with 10 vol 0.1 M NaCl and the filters were washed several times in 15 ml 0.3 M NaCl, 0.1% SDS, 2 mM EDTA, 10 mM Tris-HCl (pH 7.5) by shaking at 45° C. and several times in the same solution without SDS at 4° C. Elution of the hybridized RNA-DNA was effected in 30 μl 5 mM potassium chloride at 100° C. for 1 min.

4. Results Of The RNA Selection Hybridization Assay

Sixteen groups of about 46 clones were screened (Groups A-P). In six of the groups, Fraction 1B contained the only IFN-β mRNA activity, in eight of the groups no IFN-β mRNA was detected and in two groups (Groups C and O) IFN-β mRNA was observed in Fraction 4B. The group C and O assays are reported in the following format:

logarithm of IFN-β units (calibrated against reference standard 69/19), detected in the assay of Fraction 1B (non-hybridized) and in the assay of Fraction 4B (hybridized). The limit of detection was 0.1.

| Group | Fraction 1B | Fraction 4B |
|---|---|---|
| C | 1.0 | 0 |
| | 0.5 | 0.5 |
| | 0 | 0.2 |
| 0 | 0 | 0 |
| | 0.2 | 0.5 |

Group 0was subdivided into 6 subgroups (Subgroups $0_1$ to $0_6$; four of eight clones and two of seven clones) and hybridized and assayed as before, except that a 400 ml culture per clone was used. The subgroups gave the following results, presented in the same format as above. Hybridization was carried out on DMB-cellulose powder except as otherwise indicated.

| Subgroup | Fraction 1B | Fraction 4B |
|---|---|---|
| $0_1$ | 0 | 1.2 |
| | 0 | 1.5 |
| | 0 | 0.5 |
| | 0 | 0.5 |
| | 0.2 | 0.5 |
| | 0 | 1.2* |
| $0_2$ | 0.7 | 0 |
| $0_3$ | 0.7 | 0 |
| | 0.5 | 0 |
| $0_4$ | 0 | 0 |
| $0_5$ | 0.5 | 0 |
| $0_6$ | 0 | 0 |

*DBM cellulose paper method.

Subgroup $0_1$ was subdivided into its individual clones (designated clones $0_{1/1}$-$0_{1/8}$) and hybridized and assayed as before, except that a 700 ml culture per clone was used. The hybridization was again carried out on DBM-cellulose powder except as otherwise indicated

| Clone | Fraction 1B | Fraction 4B |
|---|---|---|
| $0_{1/1}$ | 0.2 | 0 |
| | 0.7 | 0 |
| | 0.7 | 0* |
| | 1.0 | 0** |
| $0_{1/2}$ | 1.2 | 0 |
| | 0.2 | 0* |
| | 0.7 | 0** |
| $0_{1/3}$ | 1.2 | 0 |
| | 1.0 | 0.2* |
| | 1.2 | 1.0(?)* |
| | 1.2 | 0** |
| $0_{1/4}$ | 1.2 | 0 |
| | 1.2 | 0 |
| | 1.0 | 0* |
| | 1.2 | 0** |
| $0_{1/5}$ | 0.7 | 0 |
| | 0.7 | ≦0.2* |
| | 1.0 | 0 |
| $0_{1/6}$ | 0.7 | 0 |
| | 1.0 | ≦0.2* |
| | 0.5 | 0** |
| $0_{1/7}$ | 0.5 | 0 |
| | 1.2 | 0* |
| | <0.2 | 0.5** |
| $0_{1/8}$ | 0 | 1.7* |
| | <0.2 | 1.2* |
| | 0 | 0.7** |
| | 0 | 1.0** |

*DBM cellulose paper method.
**Nitrocellulose sheets.

Therefore, clone 01/8 contains a recombinant DNA molecule capable of hybridizing IFN-β mRNA from total RNA containing IFN-β mRNA.

Non-specific RNA-DNA binding is highly unlikely, because a comparison of Fractions 1A and 4A revealed substantially no non-specific binding of STNV DNA in these same experiments. E.g., as monitored by translation in a rabbit reticulocyte lysate in the presence of $^{35}$S-methionine, followed by gel electrophoresis, as described above. Clone 01/8 was designated *E. coli* HB101(G-pBR322(Pst)/HFIF1 ("G-HB101-pHFIF1"), its recombinant DNA molecule G-pBR322(Pst)HFIF1 ("pHFIF1") and its hybrid insert "pHFIF1 fragment". This nomenclature indicates that the clone and recombinant DNA molecule originated in Gent ("G") and comprises plasmid pBR322 containing, at the PstI site HuIFN-β cDNA ("HFIF"), the particular molecule being the first located ("1").

IDENTIFICATION OF CLONES CONTAINING RECOMBINANT DNA-MOLECULES CROSS-HYBRIDIZING TO pHFIF1 pHFIF1, isolated above, was used to screen the library of clones, prepared previously, for bacterial clones containing recombinant DNA molecules having related hybrid DNA inserts, by colony hybridization (M. Grunstein and D. S. Hogness, "A Method For The Isolation Of Cloned DNA's That Contain A Specific Gene", *Proc. Natl. Acad. Sci. USA*, 72, pp. 3961-3965 (1975)). This method allows rapid identification of related clones by hybridization of a radioactive probe made from pHFIF1 to the DNA of lysed bacterial colonies fixed in nitrocellulose filters.

The library of clones stored in microtiter plates, as described above, was replicated on similar size nitrocellulose sheets (0.45 μm pore diameter, Schleicher and Schuel or Millipore), which had been previously boiled to remove detergent, and the sheets placed on LB-agar plates, containing tetracycline (10 μg/ml). Bacterial colonies were grown overnight at 37° C. Lysis and fixation of the bacteria on the nitrocellulose sheets took place by washing consecutively in 0.5 N NaOH (twice for 7 min), 1 M Tris-HCl (pH 7.5) (7 min), 0.5 M Tris-HCl (pH 7.5) and 1.5 M NaCl (7 min), 2× SSC (0.15 M NaCl, 0.015 M sodium citrate (pH 7.2) (7 min)). After thorough rinsing with ethanol and air drying, the sheets were baked at 80° C. for 2 h in vacuo and stored at room temperature.

A Hinf I restriction fragment specific for the pHFIF1 fragment (infra) served as the probe for colony hybridization, described infra. This fragment (~170 base pairs) was purified by electrophoresis of the Hinf digestion products of pHFIF1 in a 6% polyacrylamide gel. After staining the DNA bands with ethidiumbromide, the specific fragment was eluted, reelectrophoresed and $^{32}$P-labelled by "nick translation" (P. W. J. Rigby et al., "Labeling Deoxyribonucleic Acid To High Specific Activity In Vitro By Nick Translation With DNA Polymerase I", *J. Mol. Biol.*, 113, pp. 237-251 (1977)) by incubation in 50 μl 50 mM Tris-HCl (pH 7.4), 10 mM MgCl$_2$, 20 mM β-mercaptoethanol, containing 2.5 μl each of dCTP, dTTP and dGTP at 400 μM, 100 pmoles α-ATP (Amersham, 2000 Ci/mmole) and 2.5 units of DNA-polymerase I (Boehringer) at 14° C. for 45 min. The unreacted deoxynucleoside triphosphates were removed by gel filtration over Sephadex G-50 in TE buffer. The highly $^{32}$P-labelled DNA was precipitated with 0.1 vol of 2 M sodium acetate (pH 5.1) and 2.5 vol of ethanol at 20° C.

Hybridization of the above probe to the filter impregnated DNA was carried out essentially as described by D. Hanaban and M. Meselson (personal communication): The filters, prepared above, were preincubated for 2 h at 68° C. in 0.1% Ficoll, 0.1% polyvinylpyrrolidone, 0.1% bovine serum albumin, 0.15 M NaCl, 0.03 M Tris-HCl (pH 8), 1 mM EDTA, and rinsed with 0.02% Ficoll, 0.02% polyvinylpyrrolidone, 0.02% bovine serum albumin, 0.75 M NaCl, 0.15 M Tris-HCl (pH 8), 5 mM EDTA and 0.5% SDS. The hybridization proceeded overnight at 68° C. in a solution identical to the rinsing solution above using the $^{32}$P-labelled probe which had been denatured at 100° C. for 5 min prior to use. The hybridized filters were washed twice with 0.3 M NaCl, 0.06 M Tris-HCl (pH 8), 2 mM EDTA for 2 h at 68° C. before air drying and autoradiography.

About 1350 clones, originating from the 800-900 DNA size class, were screened. Thirteen colonies, including pHFIF1, gave a positive result. These clones were designated G-HB101-pHFIF1 to 13 and their recombinant DNA molecules pHFIF1 to 13. One of the clones, pHFIF2, was hybridized with poly(A) mRNA containing IFN-β mRNA and assayed using DBM-cellulose paper (supra). Because the total IFN-RNA activity was detected in the hybridized fraction and the unhybridized RNA did not contain any detectable activity, it is clear that clones identified by colony hybridization to a part of the pHFIF1 fragment also hybridized to IFN-β mRNA.

It is, of course, evident that this method of clone screening using the HuIFN-β DNA insert of pHFIF1 or another DNA insert of a clone identified using the DNA insert of pHFIF1, as described above, may be employed equally well on other clones containing DNA sequences arising from recombinant DNA technology, synthesis, natural sources or a combination thereof or clones containing DNA sequences related to any of the above DNA sequences by mutation, including single or multiple, base substitutions, insertions, inversions, or deletions. Therefore, such DNA sequences and their identification also fall within this invention. It is also to be understood that DNA sequences, which are not screened by the above DNA sequences, yet which as a result of their arrangement of nucleotides code for those polypeptides coded for by the above DNA sequences also fall within this invention.

CHARACTERIZATION OF THE IFN-β-RELATED RECOMBINANT PLASMIDS

The thirteen clones (pHFIF1-13) which were detected by colony hybridization were further characterized. A physical map of the inserts of these clones was contructed and the orientation of the inserts in the various clones was determined.

The physical maps of the plasmids were constructed by digestion with various restriction enzymes (New England Biolabs) in 10 mM Tris-HCl (pH 7.6), 7 mM MgCl$_2$ and 7 mM β-mercaptoethanol at 37° C. by well-known procedures. The products of digestion were electrophoresed in 2.2% agarose or 6% polyacrylamide gels in 40 mM Tris-HOAc (pH 7.8), 20 mM EDTA. They were analyzed after visualization by staining with ethidiumbromide and compared with the detailed physical map of pBR322 (J. G. Sutcliffe, supra). Restriction maps of the different plasmids were contructed on the basis of these digestion patterns. These were refined by sequencing the DNA inserts in various of the plasmids, substantially by the procedure of A. M. Maxam and W. Gilbert, "A New Method For Sequencing DNA", *Proc. Natl. Acad. Sci. USA*, 74, pp. 560-564 (1977).

Plasmid DNA was prepared from various of the pHFIF1-13 in accordance with this invention by the method of Kahn et al. (supra), employed previously herein to isolate the DNA from the sets of clones for screening. The isolated form I DNA was purified by neutral sucrose-gradient centrifugation as before and restricted by various restriction enzymes, essentially as recommended by the supplier (New England Biolabs).

Restricted DNA was dephosphorylated for 30 min at 65° C. in the presence of 4 units bacterial alkaline phosphatase and 0.1% SDS. Following two phenol extractions and ethanol precipitation, the DNA was 5'-terminally labelled with γ-$^{32}$P-ATP (~3000 Ci/mmole) and polynucleotide kinase (P-L Biochemicals, Inc.).

Figure 7:
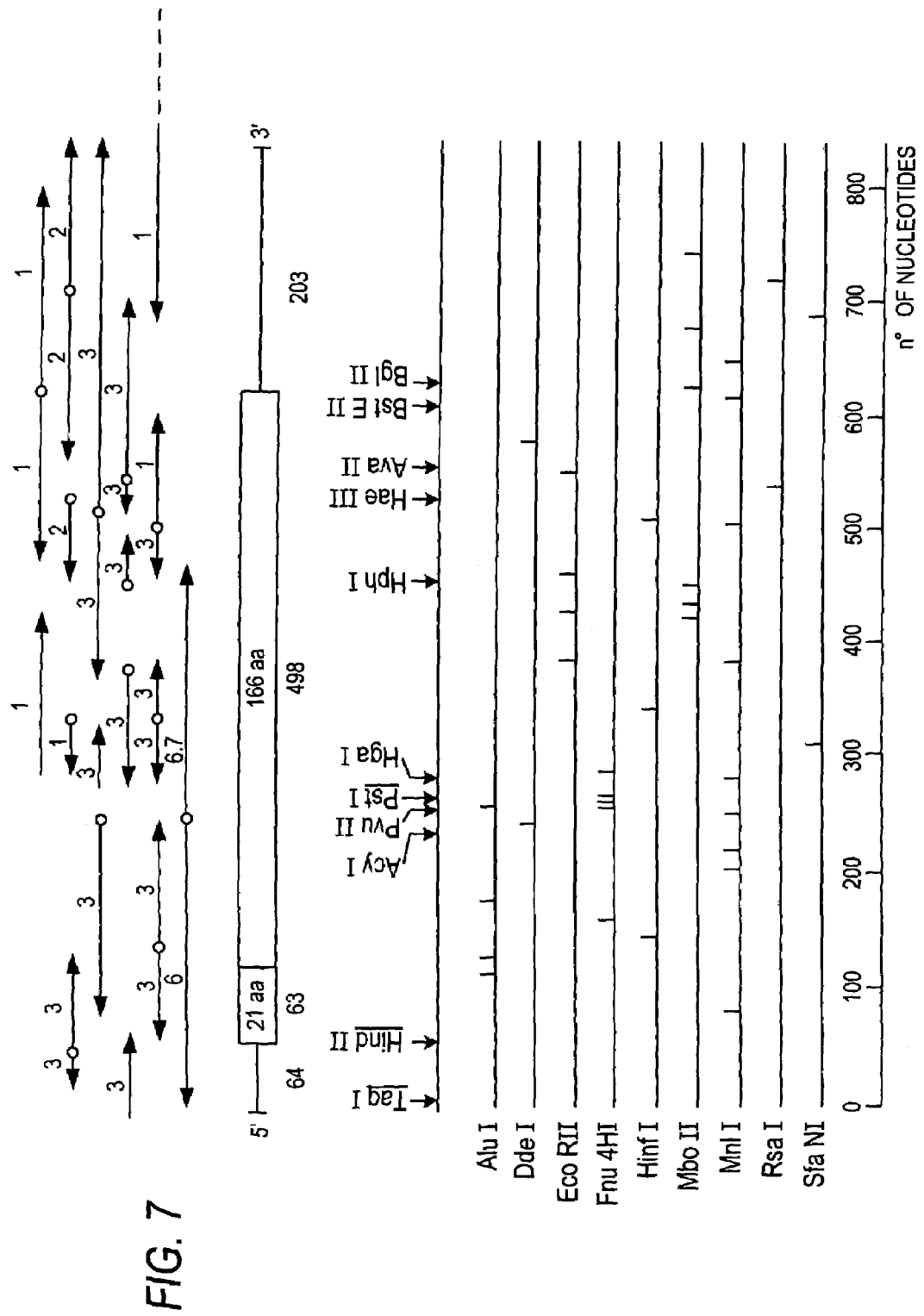
FIG. 7 displays a restriction map of the HuIFN-β gene of this invention and the sequencing strategy used in sequencing pHFIF3, pHFIF6, and pHFIF7.

For sequencing, labelled fragments were handled in two ways. Some were purified on a polyacrylamide gel prior to cleavage with a second restriction enzyme. Others were immediately cleaved with a second restriction enzyme. In both cases the desired fragments were separated on a polyacrylamide gel in Tris-borate-EDTA buffer. FIG. 7 displays the various restriction fragments (the circles indicating the label and the arrow the direction of sequencing) and the sequencing strategy employed using pHFIF1, pHFIF3, pHFIF6 and pHFIF7.

The fragments were degraded according to the method of A. M. Maxam and W. Gilbert (supra). The products were fractionated on polyacrylamide gels of various concentrations and lengths in 50 mM Tris-borate, 1 mM EDTA (pH 8.3) at 900 V to 2000 V.

Figure 5:
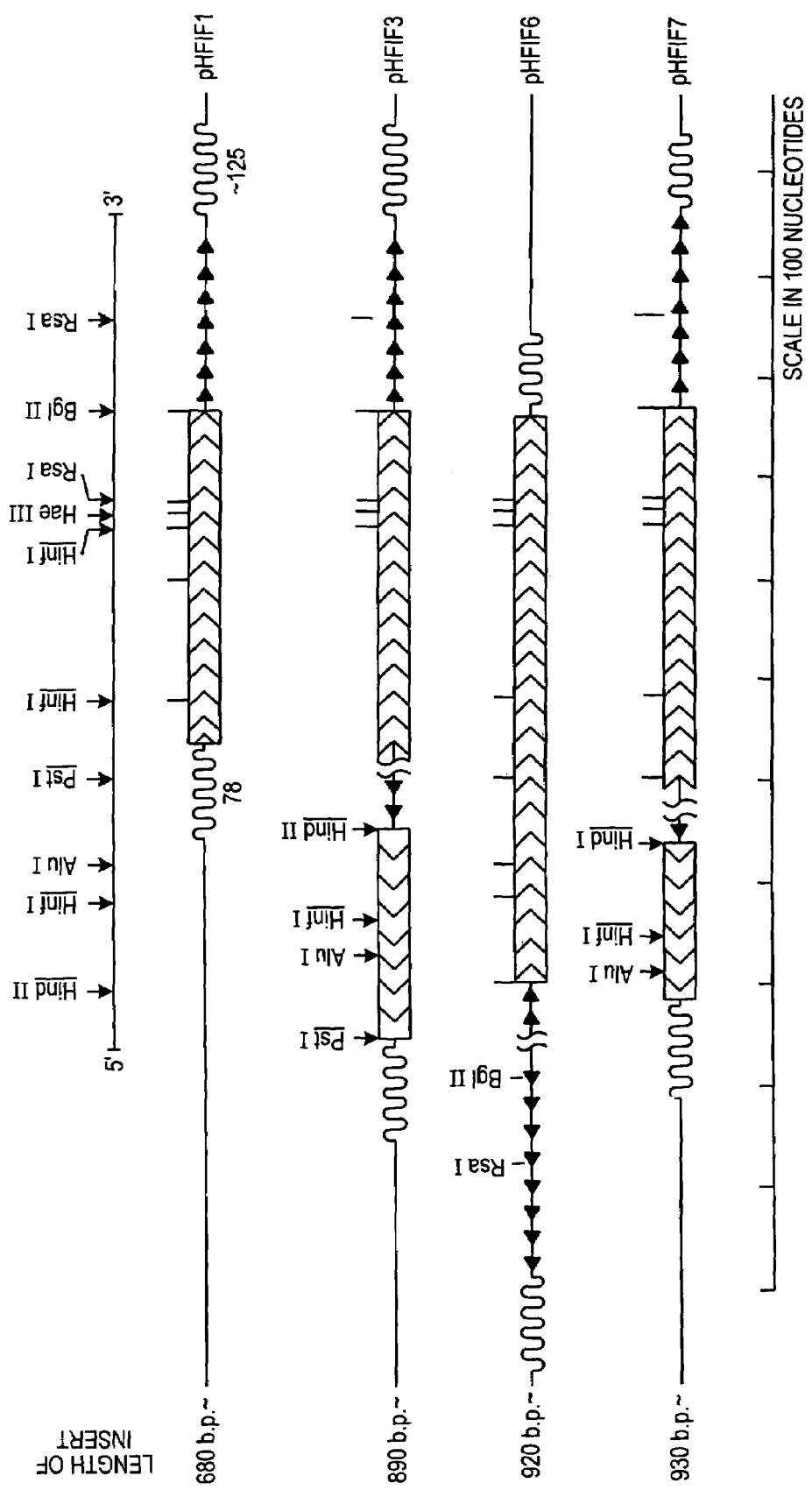
FIG. 5 displays the orientation and restriction maps of several plasmids in accordance with this invention.

Each stretch of cDNA insert was sequenced from both strands and each restriction site which served as labelled terminus was sequenced using a fragment spanning it. The composite nucleotide sequence thus obtained for the coding strand of IFN-β DNA or gene and its corresponding amino acid sequence is depicted in FIG. 4. Because none of plasmids pHFIF1-13 contained the complete gene for HuIFN-β, FIG. 4 results from a combination of the data from at least two such plasmids. In this regard, FIG. 5 displays the relationship of inserts pHFIF1, pHFIF3, pHFIF6 and pHFIF7, the solid arrows or chevrons indicating the orientation of the various parts of the inserts.

Referring now to FIG. 4, the heteropolymeric part of the insert is flanked on one end by a segment rich in T's and by a string of A's (probably reflecting the polyA terminus of the mRNA). For reference the insert is numbered from first nucleotide of the composite insert to a nucleotide well into the untranslated section of the insert. An ATG initiation triplet at position 65-67 and a TGA termination triplet at position 626-628 define a reading frame uninterrupted by nonsense codons. Any other translatable sequence, i.e., in different reading frames, flanked by an ATG or a GTG and a termination signal is too short to code for a polypeptide of the expected size of IFN-β. Therefore, the region between nucleotides 65 and 625 most likely includes the nucleotide sequence for the composite DNA sequence that codes for IFN-β in accordance with this invention.

This sequence does not exclude the possibility that modifications to the gene such as mutations, including single or multiple, base substitutions, deletions, insertions, or inversions may not have already occurred in the gene or may not be employed subsequently to modify its properties or the properties of the polypeptides translated therefrom. Nor does it exclude any polymorphism which may result in physiologically similar but structurally slightly different genes or polypeptides than that reported in FIG. 4 (supra, p. 3). For example, another clone identified in accordance with this invention has a "T" instead of a "C" at nucleotide 90 of the nucleotide sequence coding for IFN-β. This change in the third nucleotide of the codon does not change the amino acid coded therefrom. The amino acid sequence coded for by the DNA sequence of FIG. 4 is identical to the amino acid sequence reported by Taniguichi et al., *Gene*, 10, pp. 11-15 (1980).

It should of course be understood that cloned cDNA from polyA RNA by the usual procedures (A. Efstratiadis et al, supra) may lack 5'-terminal nucleotides and may even contain artifactual sequences (R. I. Richards et al., "Molecular Cloning And Sequence Analysis Of Adult Chicken β-Globin cDNA", *Nucleic Acids Research*, 7, pp. 1137-46 (1979)). Therefore, it is not certain that the ATG located at nucleotides 65-67 is in fact the first ATG of authentic IFN-β coding sequence. However, for the purposes of the following description, it is assumed that the ATG at nucleotides 65-67 is the first ATG of authentic IFN-β mRNA.

By comparing the polypeptide coded by this region of the insert with that sequence of 13 amino-terminal amino acids of authentic human fibroblast interferon—MetSerTyrAsn-LeuLeuGlyPheLeuGlnArgSerSer—determined by Knight et al. (supra), it appears that the chosen reading frame is correct and that nucleotides 65-127 may code for a signal peptide which precedes the nucleotide sequence coding for the "mature" polypeptide.

In addition, in eukaryotic mRNAs the first AUG triplet from the 5' terminus is usually the initiation site for protein synthesis (M. Kozak, "How Do Eukaryotic Ribosomes Select Initiation Regions In Messenger RNA?", *Cell*, 15, pp. 1109-25 (1978)). Here, the codon in the composite fragment corresponding to the first amino acid of fibroblast interferon is 22 codons from the first ATG. This again suggests that the DNA sequence coding for fibroblast interferon may be preceded by a sequence determining a signal polypeptide of 21 amino acids. The presumptive signal sequence contains a series of hydrophobic amino acids. Such accumulation of hydrophobic residues is, of course, characteristic of signal sequences (c.f., B. D. Davis and P. C. Tai, "The Mechanism Of Protein Secretion Across Membranes", *Nature*, 283, pp. 433-38 (1980)).

The nucleotide sequence apparently corresponding to "mature" HuIFN-β comprises 498 nudleotides, which code for 166 amino acids. Assuming that there is no carboxyterminal processing, the molecular weight of the interferon polypeptide is 20085. The base composition of the coding sequence is 45% G+C. The codon usage within the interferon coding sequences is in reasonable agreement with that complied for mammalian mRNAs in general (R. Grantham et al., "Coding Catalog Usage And The Genome Hypothesis", *Nucleic Acids Research*, 8, pp. 49-62 (1980)). Any deviations observed may be ascribed to the small numbers involved.

The structure of the polypeptide depicted in FIG. 4 for the composite fragment, of course, does not take into account any modifications to the polypeptide caused by its interaction with in vivo enzymes, e.g., glycosylation. Therefore, it must be understood that the amino acid sequence depicted in FIG. 4 may not be identical with HuIFN-β produced in vivo.

The comparison of the first 13 amino acids of authentic fibroblast interferon (Knight et al., supra) and the sequence deduced from the composite gene of FIG. 4 shows no differences. The amino acid compositions determined directly for authentic fibroblast interferon on the one hand and that deduced from the sequence of the composite gene of this invention on the other also show substantial similarities. FIG. 6 displays a comparison of these compositions.

Figure 8:
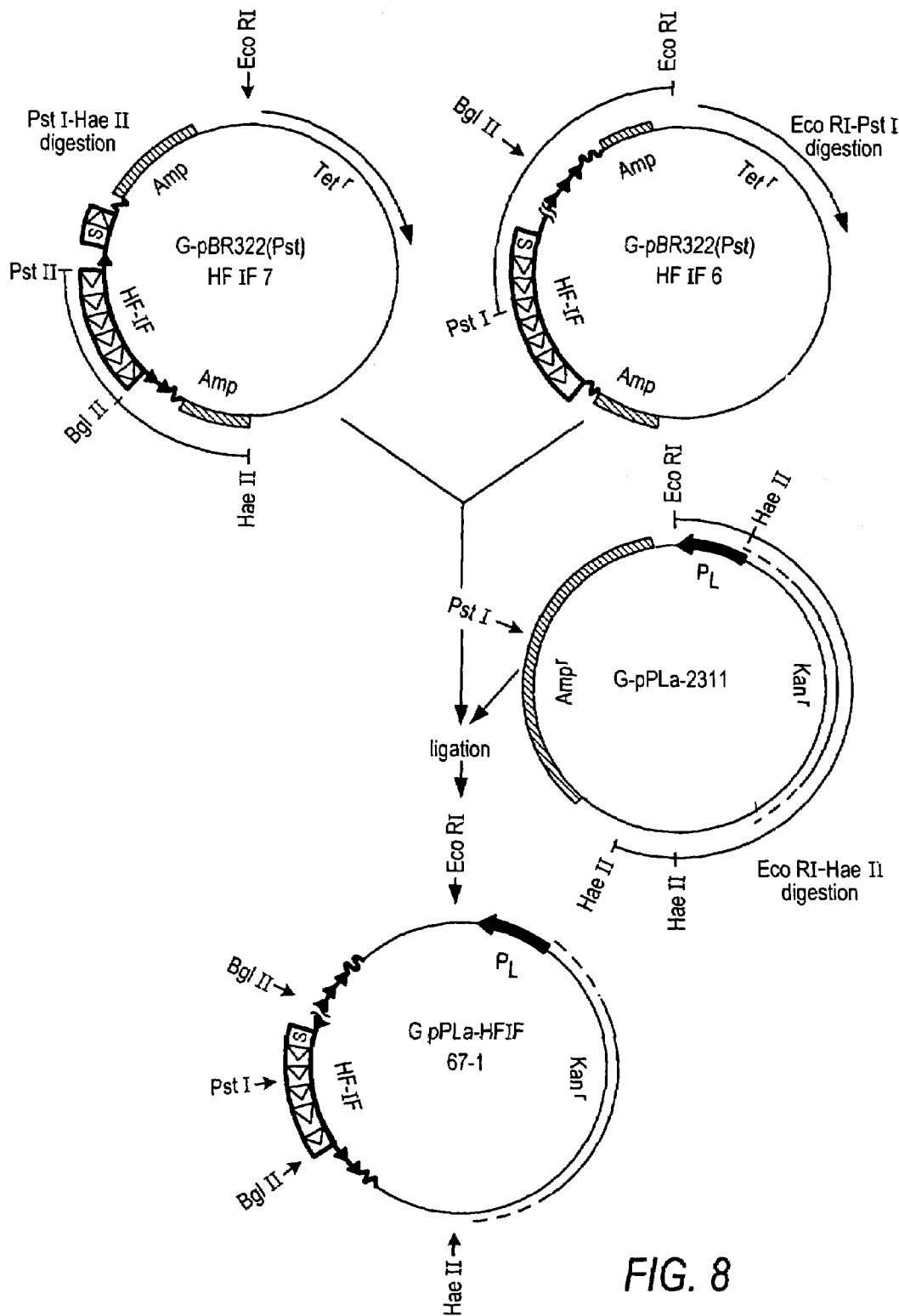
FIG. 8 is a schematic outline of the construction of recombinant DNA molecule pPLa-HFIF-67-1 of this invention.

Although none of the recombinant DNA molecules initially prepared in accordance with this invention contain the complete DNA sequence for fibroblast interferon, they do provide a useful probe to screen collections of DNA sequences for those sequences which are related to HuIFN-β. Furthermore, a combination of portions of the inserts of these recombinant DNA molecules to afford the complete IFN-β coding sequence is, as is demonstrated below, within the skill of the art. For example, by reference to FIG. 5 and FIG. 8 it can readily be seen that the PstI-BglII fragment of pHFIF6 may be joined with the PstI-HaeII fragment of pHFIF7 or the EcoRI-PstI fragment of pHFIF6 may be joined with the PstI-HaeII fragment of pHFIF7 or the BglII-PstI fragment of pHFIF6 may be joined with the PstI-BglII fragment of clone 7 to form a composite HuIFN-β coding sequence. The joining of these fragments may, of course, be done before or after insertion of the cloned fragment into a desired plasmid.

PREPARATION OF PLASMIDS CONTAINING THE COMPLETE DNA SEQUENCE CODING FOR HuIFN-β FOR THE PURPOSE OF EXPRESSING POLYPEPTIDES DISPLAYING HuIFN-β ACTIVITY

Bacteriophage λ contains two strong promoters, $P_L$ and $P_R$, whose activity is under the control of a repressor protein, the product of the phage gene cI. In the presence of repressor, transcription from these promoters is fully repressed. Removal of repressor turns on strong transcription from $P_L$ and $P_R$ (for review, see H. Szybalski and W. Szybalski "A Comprehensive Molecular Map Of Bacteriophage λ", *Gene*, 7, 217-270 (1979)).

Derivatives of the multicopy plasmid pBR322 (F. Bolivar et al. "Construction And Characterization Of New Cloning Vehicles. II. A Multiple Cloning System", *Gene*, 2, 95-113 (1977)) were constructed to incorporate the $P_L$ promoter. These plasmids are described in Great Britain patent application 80.28983, filed Sep. 8, 1980 and incorporated herein by reference.

A. Structure Of Plasmids Containing The $P_L$ Promoter Plasmid pPLa2311

Plasmid pPLa2311 (shown in FIG. 8) consists of three HaeII fragments. The largest fragment, about 1940 base pairs, contains the $P_L O_L$ region from bacteriophage λ and the β-lactamase gene region from pBR322 (J. Sutcliffe, "Complete Nucleotide Sequence Of The *Escherichia coli* Plasmid pBR322", *Cold Spring Harbor Symposium*, 49, 77-90, (1978)). Adjacent to this fragment is a 370-base pair HaeII fragment derived from plasmid Col $E_1$. The origin of replication spans the junction between these two fragments (A. Oka et al. "Nucleotide Sequence Of Small $ColE_1$ Derivatives. Structure Of The Regions Essential For Autonomous Replication And Colicin $E_1$ Immunity", *Mol. Gen. Genet.*, 172, 151-159 (1979)). The third HaeII fragment, about 1600 base pairs in length, codes for resistance to kanamycin. This fragment was originally derived from plasmid $pCR_1$ (C. Covey et al. "A Method For The Detection Of Restriction Sites In Bacterial Plasmid DNA", *Mol. Gen. Genet.*, 145, 155-158 (1976)). The direction of transcription from the $P_L$ promoter runs in the same sense as the β-lactamase gene. Plasmid pPLa2311 confers resistance to 100 µg/ml carbenicillin and 50 µg/ml kanamycin.

Plasmid G-pPLa8

Plasmid G-pPLa8 (shown in FIG. 9) was derived from pPLa2311 by converting the PstI site in the β-lactamase gene to a BamHI site. This was accomplished by $S_1$ nuclease treatment of PstI-opened pPLa2311 followed by blunt-end ligation to a BamHI linker fragment (obtained from Collaborative Research Inc., Waltham, Mass.) and recircularization of the molecule after BamHI cleavage. Plasmid pPLa8 no longer specifies for resistance to carbenicillin, but it still confers resistance to kanamycin.

Plasmid G-pPLc24

Figure 10:
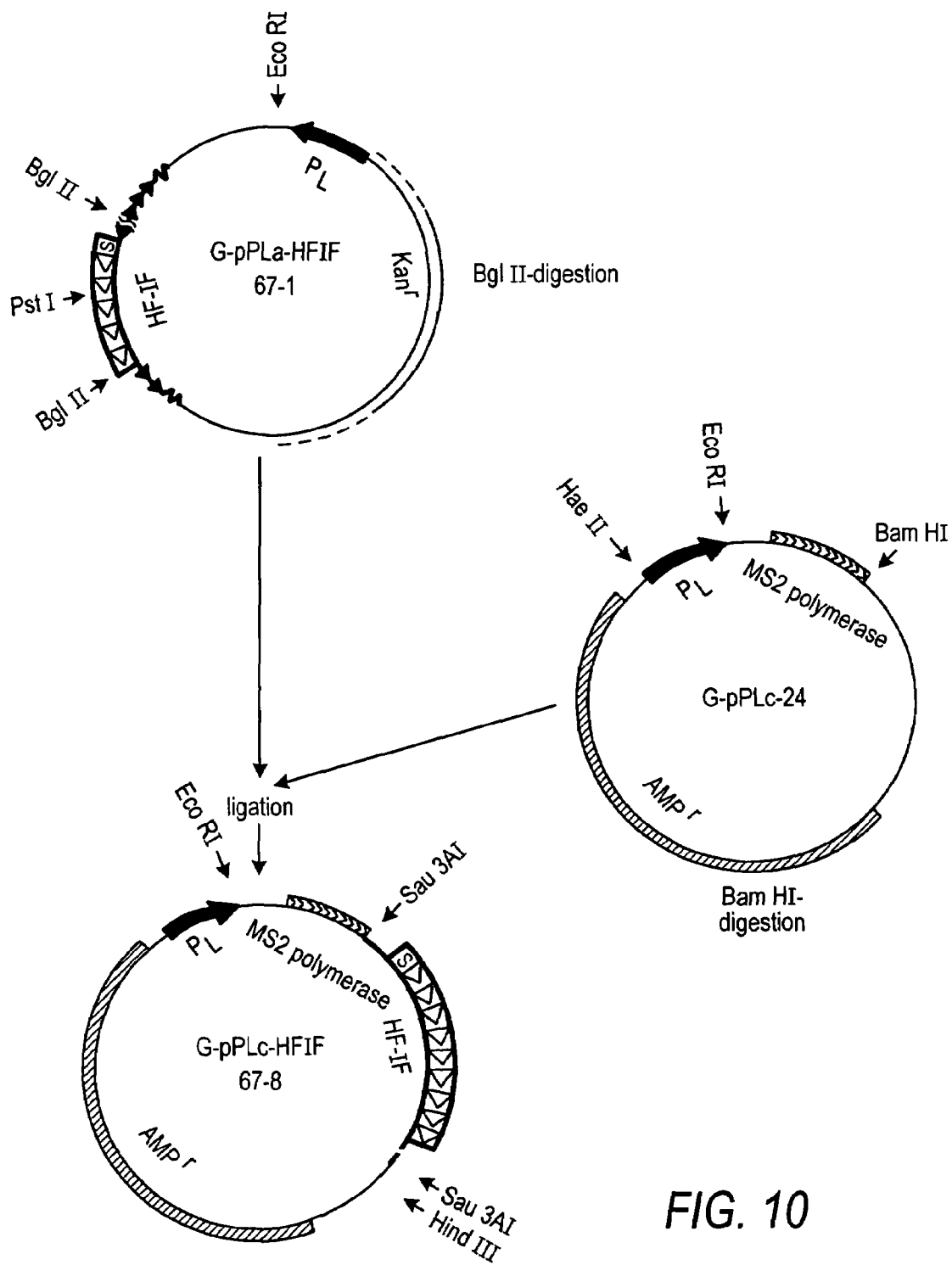
FIG. 10 is a schematic outline of the construction of recombinant DNA molecule pPLc-HFIF-67-8 of this invention.

Plasmid G-pPLc24 (shown in FIG. 10) contains the β-lactamase gene and the origin of replication from pBR322. A 290 base pair HaeII-EcoRI fragment contains the $P_L O_L$ region from bacteriophage λ. The direction of transcription from the $P_L$ promoter is towards the EcoRI site. A 431 base pair EcoRI-BamHI fragment codes for the ribosome binding site and the first 98 amino acid residues of the bacteriophage MS2 replicase gene, obtained from plasmid pMS2-7 (R. Devos et al. "Construction And Characterization Of A Plasmid Containing A Nearly Fullsize DNA Copy Of Bacteriophage MS2 RNA", *J. Mol. Biol.*, 128, 595-619 (1979)). Translation of the MS2 replicase protein fragment runs colinear with the transcription from the $P_L$ promoter.

B. Temperature-dependent Switch-On Of $P_L$ Promoter Activity

Transcription from the $P_L$ promoter—present on plasmids pPLa2311, pPLa8 and pPLc24—is repressed by maintaining the plasmids in an *E. coli* strain that synthesizes the repressor protein. Due to its autoregulating mode of synthesis (M. Ptashne et al. "Autoregulation And Function Of A Repressor In Bacteriophage λ", *Science*, 194, 156-161 (1976)), one copy of the cI gene on the chromosome of a lysogenic strain is able to repress fully the $P_L$ promoter present on a multicopy plasmid.

The strains employed in this invention were *E. coli* K12ΔHI (K12 M72 $lac_{am}$ ΔtrpEA2 $Sm^R$ (λcI857 $N_{am}7$ $N_{am}5$ ₃ΔHI bio); U. Bernard et al. "Construction Of Plasmid Cloning Vehicles That Promote Gene Expression From The Bacteriophage λ $P_L$ Promoter", *Gene*, 5, 59-76 (1979)) and *E. coli* M5219 (K12 M72 $lac_{am}trp_{am}Sm^R$ (λcI857 ΔHI bio252); H. Greer, "The kil Gene Of Bacteriophage λ", *Virology*, 66, 589-604 (1975)). Both strains harbor a defective, non-excisable λ prophage carrying a mutant cI gene. The mutant gene codes for a temperature-sensitive repressor, thus allowing turn on of transcription from the $P_L$ promoter by shifting the temperature—at 28° C. the repressor is active and represses transcription from the $P_L$ promoter but at 42° C. the repressor is inactivated and transcription from the $P_L$ promoter is switched on.

The ΔHI deletion of the prophage removes part of the cro gene and all other genes further to the right of cro (M. Castellazzi et al. "Isolation And Characterization Of Deletions In Bacteriophage λ Residing As Prophage I *E. coli* K12", *Mol. Gen. Genet.*, 117, 211-218 (1972)). The deletion of the cro gene is advantageous because accumulation of the cro protein is known to repress transcription from the $P_L$ promoter (A. Johnson et al. "Mechanism Of Action Of The cro Protein Of Bacteriophage λ", *Proc. Natl. Acad. Sci. U.S.A.*, 75, 1783-1787 (1978)). Strain M5219 in addition contains the bio252 deletion which removes all genes to the left cIII, including kil.

Upon temperature induction strain M5219 expresses a functional N-gene product. Strain K12ΔHI on the other hand has two amber mutations in N rendering it functionally N-negative. The product of the N gene is known to act as an anti-terminator in bacteriophage λ (J. W. Roberts, "Transcription Termination And Late Control In Phage λ", *Proc. Natl. Acad. Sci. U.S.A.*, 72, 3300-3304 (1975)). The anti-termination effect was equally observed with terminator sequences not naturally present on phage λ DNA (e.g., the natural stop at the end of the trp operon), provided the RNA transcript starts at the $P_L$ promoter. Furthermore, polarity effects, introduced by the presence of a nonsense codon in the $P_L$ transcript, were relieved under the action of the N-gene protein (for review see N. Franklin and C. Yanofsky, "The N Protein Of λ: Evidence bearing On Transcription Termination, Polarity And The Alteration Of *E. coli* RNA Polymerase" in *RNA Polymerase* (Cold Spring Harbor Laboratory, 1976) pp. 693-706).

Therefore, having the aforementioned plasmids in a thermo-inducible bacterial cI background allows experimental switching on or off of the activity of $P_L$ promoter. And, the choice of K12ΔHI or M5219 allows transcription to proceed either in the absence or presence of the N-gene product. The latter could be advantageous, as described above, in instances where DNA regions are to be transcribed that contain transcription terminator-like sequences or slow-down sequences for the RNA polymerase.

C. Construction Of Clones Which Have A DNA Sequence Coding For HuIFN-β Inserted Into A Plasmid Containing The $P_L$ Promoter In the following description, isolation of plasmid DNA, restriction analysis of DNA and ligation of DNA fragments were performed as described above for the cloning of double-stranded DNA. The transformation step was also as described above except that, when strains K12ΔHI or M5219 were used as the host, heat shock was done at 34° C. for 5 min and the transformed cells were incubated at 28° C.

1. Construction Of Plasmid G-pPLa-HFIF-67-1

The rationale for this construction was the observation that combination of appropriate restriction fragments from clones G-pBR322(Pst)/HFIF6 and G-pBR322(Pst)/HFIF7 allows the reconstruction of a complete, continuous coding sequence of IFN-β. The flow of the derived fragments through the several construction steps is shown schematically in FIG. 8. Plasmid G-pBR322(Pst)/HFIF6 was cleaved with EcoRI and PstI and ligated to plasmid G-pBR322(Pst)/HFIF7 which had been cleaved with PstI and PvuI. Following ligation the mixture was digested with EcoRI and HaeII. A 4-fold molar excess of this mixture was then ligated to plasmid G-pPLa2311 which had been digested with HaeII and EcoRI. Transformants were obtained in strain C600$r_K m_K^+$(λ) (which was used because of its relatively high transformation capability and because it contains a wild-type cI gene) by selection for kanamycin resistance. Of 15 transformants screened, two had lost resistance to carbenicillin. Restriction analysis of the DNA isolated from the plasmids of these transformants revealed that one had the desired structure of G-pPLa-HFIF-67-1 depicted in FIG. 8. This plasmid contained a unique EcoRI site and a unique PstI site. Combined EcoRI-PstI digestion produced two fragments—the smaller of which comigrated with a fragment obtained after EcoRI-PstI cleavage of G-pBR322(Pst)/HFIF6. BglII digestion cleaved out a small fragment of about 650 base pairs. The size of the latter fragment is consistent with the expected size after joining the proximal BglII-PstI fragment of clone G-pBR322(Pst)/HFIF6 to the distal PstI-BglII part of G-pBR322(Pst)/HFIF7. HincII digestion produced three fragments as expected from the presence of the HincII sites in the $P_L$ region, the amino-terminal part of the β-lactamase gene and the untranslated 5' end of the DNA sequence of HuIFN-β. This plasmid was designated G-pPLa-HFIF-67-1.

Based on the aforementioned characterization by restriction enzyme analysis, plasmid G-pPLa-HFIF-67-1 should contain the complete coding sequence of for HuIFN-β. The direction of desired transcription runs colinearly with that from the $P_L$ promoter. In between the $P_L$ and the HiIFN-β coding sequence gene the plasmid still retains the poly(A·T) tail and an inverted 3' end fragment as in G-pBR322(Pst)/HFIF6.

2. Construction Of Plasmid G-pPLa-HFIF-67-12

Figure 9:
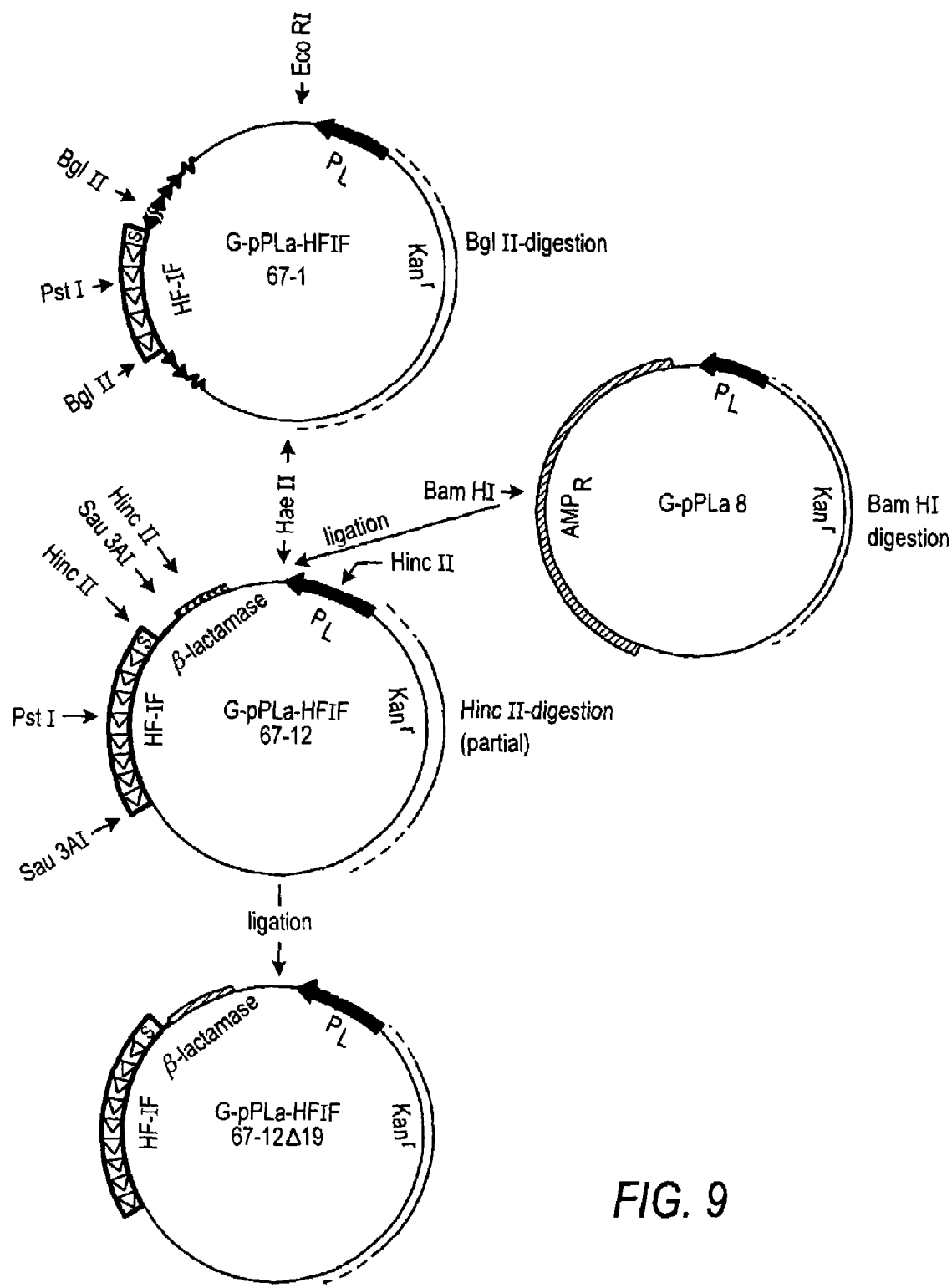
FIG. 9 is a schematic outline of the construction of recombinant DNA molecule pPLa-HFIF-67-12 and pPLa-HFIF-67-12Δ19 of this invention.

The next step in the constructions was aimed at removing from G-pPLa-HFIF-67-1 the poly(A·T) tail and part of the inverted 3' end fragment (see FIG. 9). G-pPLa-HFIF-67-1 DNA was cleaved with BglII and HpaII. Since the HuIFN-β coding sequence contains no HpaII site this treatment results in the BglII fragment containing the entire coding sequence for IFN-β and at the same time inactivates the remaining part of the vector. The resultant BglII fragment was ligated to plasmid G-pPLa8 which had been digested with BamHI. The enzymes BglII and BamHI make identical staggered ends such that BglII ends can be ligated to an opened BamHI site and vice versa. Such a reconstructed site is no longer a substrate for BglII or BamHI but is recognized by the enzyme Sau3AI (MboI) (V. Pirotta, "Two Restriction Endonucleases From *Bacillus globigii*", *Nucleic Acids Res.*, 3, 1747-1760 (1976)). Following ligation the mixture was again cleaved with BamHI to eliminate those G-pPLa8 molecules that had simply recircularized. Transformants were again obtained in C600$r_K m_K^+$(λ) selecting for kanamycin resistance.

Figure 11:
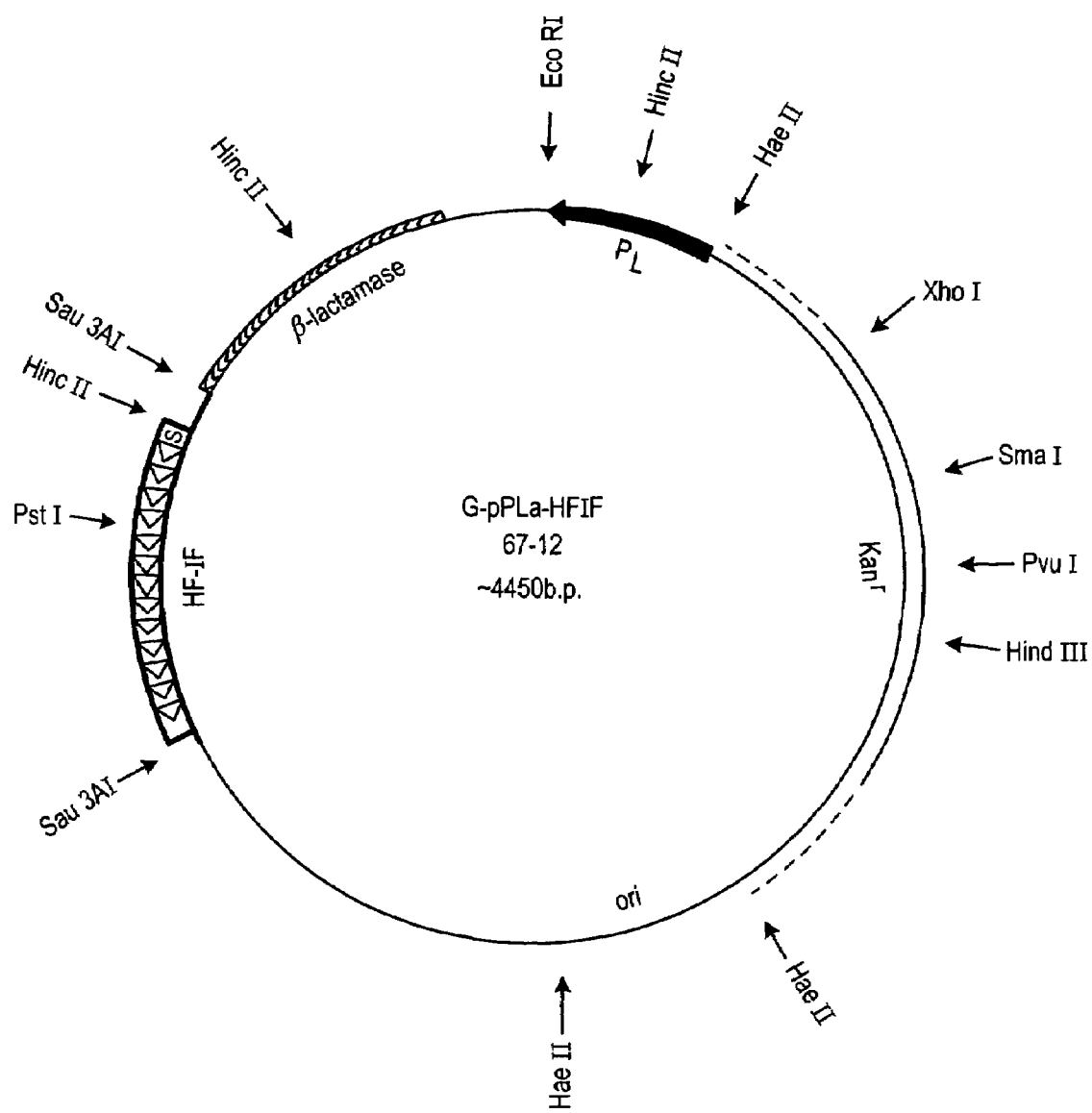
FIG. 11 is a schematic outline of the orientation and partial restriction map of pPLa-HFIF-67-12 of this invention.

The transformants were screened by size determination of uncleaved DNA on agarose gel, as described above, for characterization of the IFN-β-related recombinant plasmids. Clones which proved slightly larger than the G-pPLa8 parent were further subjected to restriction analysis with either PstI or HincII. One clone was found which contained a single PstI site and three HincII sites. One fragment of this clone comigrated with a HincII fragment from pPLa8 derived from the $P_L$ to the β-lactamase region. Another small fragment of the clone measured about 400 base pairs—consistent with insertion of the BglII fragment into G-pPLa8 in the sense orientation with respect to the $P_L$ promoter. This plasmid was designated G-pPLa-HFIF-67-12. The steps used in the construction of this plasmid are shown schematically in FIG. 9. A more detailed map of this plasmid is shown in FIG. 11. The size of the plasmid (~4450 base pairs) was estimated by the size of its constituent fragments, which in turn had been estimated by their relative mobility upon electrophoresis in agarose gels.

*E. coli* K12ΔHI and M5219 were then transformed with the characterized plasmid G-pPLa-HFIF-67-12.

Inspection of the determined nucleotide sequence around the BglII/BamHI junction in G-pPLa-HFIF-67-12 revealed an interesting feature. The polypeptide initiated at the AUG of the β-lactamase coding sequence of that plasmid terminates at a double amber codon located within the untranslated 5'-end of the HuIFN-β coding sequence. These termination codons are located 23 nucleotides before the initiating AUG of the HuIFN-β signal peptide, i.e.:

```
                 Junction
         181*    BamHI/BglII
         CCC. CGG.AUC.UUC.AGU.UUC.GGA.GGC.AAC.CUU.UCG.AAG.CCU.
         Pro- Arg-Ile-Phe-Ser-Phe-Gly-Gly-Asn-Leu-Ser-Lys-Pro- UUG.CUC.UGG.CAC.AAC.AGG.UAG.UAG GCGACACUGUUCGUGUUGUCAAC
         Leu-Leu-Trp-His-Asn-Arg am  am AUG-(HuIFN-β signal peptide coding sequence)-AUG-(mature
         HuIFN-β coding sequence)
```

The boxed figure refers to the number of the amino acid residue in the β-lactamase protein of pBR322 (J. Sutcliffe, supra). The asterisk (*) indicates that the CCU codon present at this position on pBR322 was changed to CCC as a consequence of the conversion of the PstI site in pPLa2311 to a BamHI site in pPLa8 (see above).

Therefore, this construction opens the possibility of reinitiation at the AUG of the HuIFN-β signal peptide and and therefore the possible expression of IFN-β fused to its signal peptide, but not fused to a part of β-lactamase. Such internal reinitiation following premature termination has been observed in the repressor gene of the *E. coli* lactose operon (T. Platt et al. "Translational Restarts: AUG Reinitiation Of A lac Repressor Fragment", *Proc. Natl. Acad. Sci. U.S.A.*, 69, 897-901 (1972)). This construction might enable the excretion of mature IFN-β by correct bacterially recognition of the HuIFN-β signal sequence.

3. Construction Of Plasmid G-pPLa-HFIF-67-12Δ19

Figure 12:
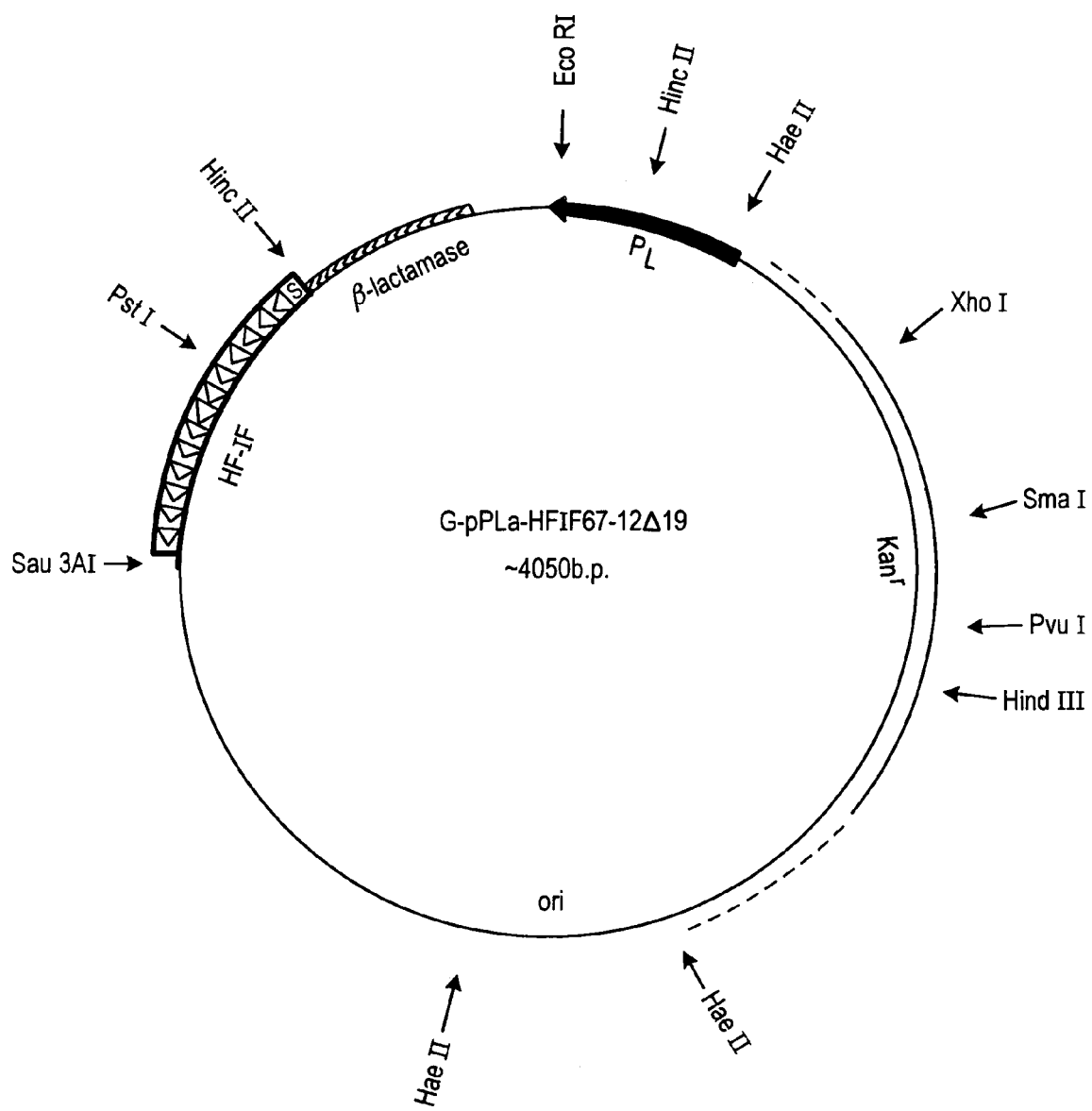
FIG. 12 is a schematic outline of the orientation and partial restriction map of pPLa-HFIF-67-12Δ19 of this invention.

From the known sequence of pBR322 and the HuIFN-β coding sequence it can be deduced that deletion from G-pPLa-HFIF-67-12 of the small HincII fragment (from within β-lactamase up to 3 nucleotides in front of the HuIFN-β signal peptide initiating AUG) results in a continuous translational reading frame starting at the AUG of β-lactamase and terminating after the HuIFN-β coding sequence. This construction is therefore predicted to code for a polypeptide consisting of 82 amino acid residues from the β-lactamase coding sequence, one amino acid coded at the fused HincII site, the HuIFN-β signal peptide and mature HUIFN-β, i.e.:

enzyme. Such molecules possess two XorII sites and under conditions used for ligation, two fragments are highly unlikely to be rejoined. Transformants were obtained in $C600r_K^- m_K^+(\lambda)$, selecting for kanamycin, and screened by restriction analysis for the presence of a single PvuI site. Further analysis of the clones was performed using HincII digestion. One clone missing the smallest HincII fragment, but otherwise identical to G-pPLa-HFIF-67-12 was designated G-pPLa-HFIF-67-12Δ19. The steps used in the construction of this plasmid are shown schematically in FIG. 9. A more detailed map of this plasmid is shown in FIG. 12. The size of the plasmid (~4050 base pairs) was estimated by totaling the size of its constituent fragments, which in turn have been estimated by their relative mobility upon electrophoresis in agarose gels. *E. coli* K12ΔHI and M5219 were then transformed with the characterized plasmid G-pPLa-HFIF-67-12Δ19.

4. Construction Of Plasmid G-pPLc-HFIF-67-8

Plasmid G-pPLc24 offers another possibility for insertion of HuIFN-β sequences in such a way that another fusion polypeptide can potentially be synthesized. Insertion of the BglII fragment from G-pPLa-HFIF-67-1 in the BamHI site of G-pPLc24 results in a continuous reading frame coding for 98

```
 82
|GUU|.AAC.AUG-(HuIFN-β signal peptide coding sequence)-AUG-
|Val|-Asn-Met (mature HuIFN-β coding sequence)
```

The boxed figure refers to the number of the amino acid residue in the β-lactamase protein of pBR322 (J. Sutcliffe, supra). Therefore, this construction may afford the expression of a fused polypeptide consisting of a portion of β-lactamase fused through one amino acid to the HuIFN-β signal peptide which itself is fused to mature HuIFN-β. Such fusion protein may be excreted from the cell.

amino acid residues from the MS2 replicase gene (W. Fiers et al. "Complete Nucleotide Sequence Of Bacteriophage MS2 RNA: Primary And Secondary Structure Of The Replicase Gene", *Nature*, 260, 500-507 (1976)), 27 amino acids coded by sequences between the BglII site and the initiating AUG of the signal sequence of HuIFN-β, followed by the HuIFN-β signal peptide and mature HuIFN-β, i.e.:

```
 98
|UGG|.GAU.CUU.CAG.UUU.CGG.AGG.CAA.CCU.UUC.GAA.GCC.UUU.GCU.
|Trp|-Asp-Leu-Gln-Phe-Arg-Arg-Gln-Pro-Phe-Glu-Ala-Phe-Ala-

CUG.GCA.CAA.CAG.GUA.GUA.GGC.GAC.ACU.GUU.CGU.GUU.GUC.AAC.
Leu-Ala-Gln-Gln-Val-Val-Gly-Asp-Thr-Val-Arg-Val-Val-Asn-

AUG-(HuIFN-β signal peptide coding sequence)-AUG-(mature
Met

HuIFN-β coding sequence)
```

G-pPLa-HFIF-67-12 was partially digested with HincII. Following ligation at a DNA concentration of about 0.01 μg/ml, the DNA was cleaved with XorII, an isoschizomer of PvuI producing 3' protruding ends (R. Wang et al., *Biochim. Biophys. Acta*, in press), and religated at low DNA concentration. Parent G-pPLa-HFIF-67-12 contains two XorII sites: one site inactivates the kanamycin gene and the other one is located in the HincII fragment to be deleted from the plasmid. The purpose of the XorII digestion-religation step is to eliminate parent DNA molecules not cleaved by the HincII The boxed figure refers to the number of the amino acid residue in the MS2 replicase gene protein (R. Devos et al., supra; W. Fiers et al., supra). Therefore, this construction may afford the expression of a fused polypeptide consisting of a portion of MS2 replicase, fused through 27 amino acids to the HuIFN-β signal peptide which itself is fused to mature HuIFN-β.

Figure 13:
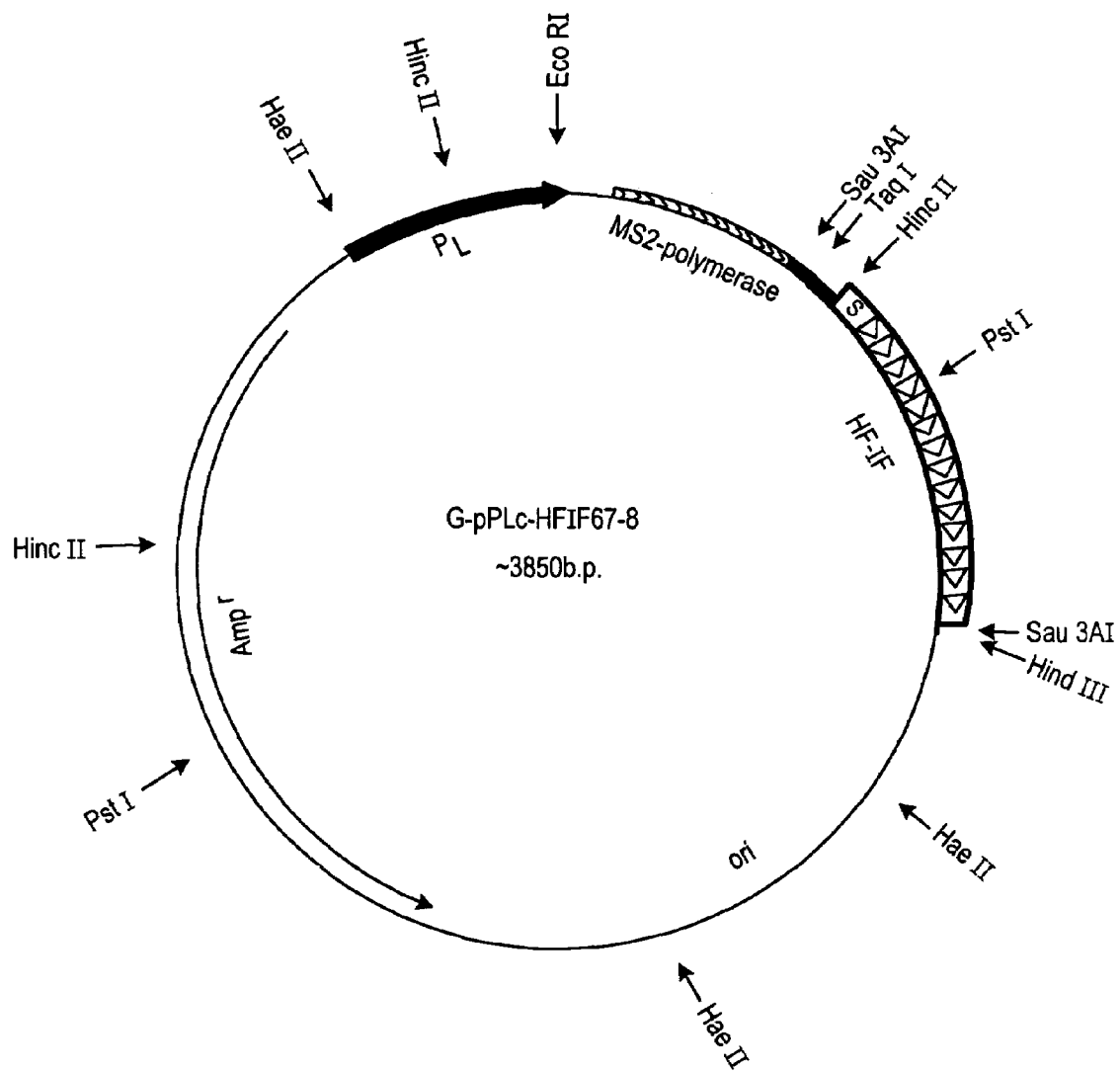
FIG. 13 is a schematic outline of the orientation and partial restriction map of pPLc-HFIF-67-8 of this invention.

G-pPLa-HFIF-67-1 DNA was digested with BglII and ligated with BamHI-cleaved pPLc24 DNA. The ligation mixture was recut with BamHI to eliminate parental pPLc24 molecules and transformed into $C600r_K^- m_K^+(\lambda)$ selecting for resistance to carbenicillin. Transformants were analyzed by restriction with HincII. From the known positions of restriction sites on pPLc24 one can predict that insertion of the BglII-IFN-β fragment in the sense orientation with respect to $P_L$ should produce an extra HincII fragment of about 650 base pairs. A representative clone exhibiting this configuration was designated pPLc-HFIF-67-8. The steps used in the construction of this plasmid are shown schematically in FIG. 10. A more detailed map of this plasmid is shown in FIG. 13. The size of the plasmid (~3850 base pairs) was estimated by totaling the size of its constituent fragments, which in turn had been estimated by their relative mobility upon electrophoresis in agarose gels. *E. coli* K12ΔHI and M5219 were transformed with the characterized plasmid G-pPLc-HFIF-67-8.

5. Construction Of Plasmid G-pPla-HFIF-67-12Δ279T

Plasmid pKT279 (a gift of K. Talmadge; pKT279 is a derivative of pBR322 having a portion of the gene for β-lactamase deleted and having a PstI site constructed at amino acid2 of β-lactamase) was digested with PstI and the 3' terminal extension removed and the fragment blunt-ended by treatment with *E. coli* DNA polymerase I (Klenow-fragment) in the presence of deoxy-nucleoside-tri phosphates. The PstI linearized and 3' blunt-ended DNA fragment of pKT279 was then digested with EcoRI to produce a fragment that inter alia codes for the signal sequence of β-lactamase and the first 4 amino acids of the mature protein.

This small fragment was then used to replace the HpaI-EcoRI fragment of pPLa-HFIF-67-12Δ19 (the HpaI site resulting as a consequence of the above-described deletion from G-pPLa-HFIF-67-12) by ligation of the HpaI-EcoRI restricted pPLa-HFIF-67-12Δ19 with that fragment in the presence of T4 DNA ligase.

The predicted sequence at the PstI (blunt-ended)-HpaI junction is:

(β-lactamase signal peptide coding sequence)-CAC.CGC.AAC.
                                              His-Arg-Asn- AUG-(HuIFN-β signal peptide coding sequence)-AUG-(mature HuIFN-
β coding sequence) Met Consequently, the construction results in IFN-β preceded by two signal sequences in tandem—a bacterial signal sequence (β-lactamase) and the IFN-β signal sequence—connected by several amino acids. Therefore, this construction may afford the expression of mature HuIFN-β fused to two signal peptides or if the tandem combination of a bacterial signal sequence and HuIFN-β's signal sequence is recognized by the bacteria and correctly cleaved, the construction may afford the expression of mature HuIFN-β and its excretion from the cell.

*E. coli* M5219 was transformed with pPLa-HFIF-67-12Δ279T.

6. Construction Of Plasmid G-pPLa-HFIF-67-12Δ218M1

Plasmid pKT218 (a gift of K. Talmadge; pKT218 is a derivative of pBR322 having a portion of the gene for β-lactamase and its signal sequence deleted and having a PstI site constructed at amino acid 4 of the signal sequence of β-lactamase) was digested with EcoRI and AluI to produce a fragment coding inter alia for the initial part of the β-lactamase signal peptide. This fragment was ligated in the presence of T4 DNA ligase with a fragment prepared from pPLa-HFIF-67-12Δ19 by AluI digestion in the presence of actinomycin D (0.05 mM) (to restrict the plasmid at the AluI site in the IFN-β signal peptide) and restriction with EcoRI.

The resulting plasmid, designated pPLa-HFIF-67-12Δ218M1, contained the initial part of the gene coding for the β-lactamase signal peptide, a part of the gene coding the HuIFN-β signal peptide and the gene coding for mature HuIFN-β. The predicted sequence of the pertinent region of the plasmid is:

```
 4
|CAA|.GCU.CUU.UCC.AUG-(mature HuIFN-β coding sequence)
|Gln|-Ala-Leu-Ser-Met-
```

The boxed figure refers to the number of the amino acid residue in the β-lactamase signal peptide of pKT218. Therefore, this construction may permit the expression of mature HuIFN-β fused to portion of a bacterial signal sequence and a portion of its own signal sequence. Again, if the bacterial host recognizes and correctly cleaves hybrid signal sequence, mature HuIFN-β could be expressed from this plasmid and excreted from the cell.

*E. coli* M5219 was transformed with pPLa-HFIF-67-12Δ218M1.

7. Construction Of Plasmid G-pPLa-HFIF-67-12ΔM1

Plasmid pPLa-HFIF-67-12Δ19 was linearized as before with AluI in the presence of actinomycin D (0.05 mM) to generate a cut at the AluI site in the signal peptide of HuIFN-β. After digestion with HpaI, the DNA was recircularized in the presence of T4 DNA ligase. The resulting plasmid, designated pPLa-HFIF-67-12ΔM1, had only a small part of the IFN-β signal sequence preceding the DNA sequence coding for mature IFN-β.

The predicted sequence of the junction is:

```
 82
|GUU|.CUC.UUU.CCA.UGA.
|Val|-Leu-Phe-Pro-STOP
              |A UG-(mature HuIFN-β coding sequence)|
```

The vertical boxed figure refers to the number of the amino acid residue in β-lactamase. The horizontal boxed figure refers to the sequence in a second reading frame. Therefore, the translation of the β-lactamase coding sequence and the remaining portion of the coding sequence for the signal peptide of IFN-β is arrested at the UGA-stop codon. However, the start-codon (AUG) for mature IFN-β is present at the same place, although in a different reading frame. Therefore, reinitiation of translation may take place at that point to produce mature HuIFN-β.

*E. coli* M5219 was transformed with pPLa-HFIF-67-12ΔM1.

8. Construction Of Plasmid G-pPLa-HFIF-67-12Δ19 BX-2

Plasmid pPLa-HFIF-67-12Δ19 was linearized with HpaI and treated with exonuclease BAL 31 to remove base pairs sequentially from the end of the linearized DNA fragment (H. Gray et al., "Extracellular Nucleases Of Pseudomonas Bal 31" I. Characterization Of Single Strand-Specific Deoxyribendonuclease", *Nucleic Acids Res.*, 2, pp. 1459-92 (1975)). By varying the time and condition of the exonuclease treatment a series of DNA fragments having various numbers of nucleotides from the coding sequence for the signal peptide of HuIFN-β, if any, preceding the AUG start codon of mature HuIFN-β are constructed. These fragments may then be manipulated to construct ribosomal binding sites at varying distances from that start codon and to afford the desired secondary structure near that codon to enhance expression of mature HuIFN-β.

The exonuclease-treated fragments were blunt ended with *E. coli* DNA polymerase I (Klenow fragment) in the presence of dATP and dGTP to fill in any 5' protruding ends. Subsequently, a double-stranded XhoI linker, having the sequence 5'-CCTCGAGG-3' (Collaborative Research), was ligated onto the blunted-ended DNA fragments. These fragments were then extended with a double-stranded EcoRI linker, having the sequence 5'-CCGAATTCGG-3' (Collaborative Research). After EcoRI digestion, the fragments having "sticky" EcoRI ends were recircularized with *E. coli* DNA ligase. The use of this ligase, instead of T4 DNA ligase, avoids the recircularization of blunt-ended fragments.

One plasmid was selected and designated pPLa-HFIF-67-12Δ19 BX-2. It has an XhoI site about 25 base pairs in front of the AUG start codon of mature HuIFN-β. The XhoI site is also preceded by a EcoRI site generated by the ligation of the EcoRI linker of the HpaI fragment to the EcoRI site just preceding the $P_L$ promoter in pPLa-HFIF-67-12Δ19. Therefore, the β-lactamase coding sequence has been deleted. Furthermore, because at least part of the HuIFN-β signal sequence has been removed, only expression of mature HuIFN-β is possible.

*E. coli* K12ΔHI was transformed with pPLa-HFIF-67-12Δ19 BX-2.

ISOLATION AND CHARACTERIZATION OF HuIFN-β MADE BY BACTERIA

A. Preparation Of Bacterial Extracts

1. Induction Procedure

An aliquot from stock cultures (frozen at −80° C. in 50% glycerol-50% LB medium), including stock cultures of strains K12ΔHI and M5219 transformed with the plasmids containing the IFN-β fragments, described above, was inoculated into fresh LB medium with the desired antibiotic and grown to saturation at 28° C. Two 500 ml batches of LB medium without antibiotic were inoculated with 1 ml each of saturated cells and grown with vigorous shaking to 28° C. to a cell density of $2\times10^8$/ml. One batch was shifted to 42° C. and continued to be shaken. Depending on the plasmid used, the culture was harvested at various times after the shift to 42° C. The control culture remaining at 28° C. was harvested at the same time as the 42° C. culture. Cells were collected by centrifugation in the GSA rotor (Sorvall) at 8000 rpm for 10 minutes. The pellets were washed in 20 ml of 50 MM Tris HCl (pH 7.4), 30 mM NaCl and repelleted in the SS34 rotor (Sorvall) for 10 minutes at 10,000 rpm. The pellet was quickly frozen in dry ice-methanol and stored at −80° C. When it was desired to shock osmotically the harvested cells the freezing step was omitted.

Two different procedures for lysis and extraction of the bacteria have been used.

2. Extraction Procedures

Lysis A

Cells were resuspended in a final volume of 4 ml of the above described buffer and lysozyme (Sigma) was added to 1 mg/ml. The incubation was for 30 min at 0° C. The suspension underwent two freeze-thaw cycles by sequential dipping in an ethanol-$CO_2$ mixture (−80° C.) and a 37° C. water bath. The S-100 fraction was prepared by ultracentrifugation of the lysed bacteria (4 ml) in a Beckman SW60 Ti rotor for 1 hr at 60,000 rpm and 4° C., after which the supernatant was further used.

Lysis B

Lysis B was performed, as described above (lysis A), except that the solution of 50 mM Tris-HCl (pH 8.0)-30 mM NaCl was replaced by 50 mM HEPES (Sigma)-NaOH (pH 7.0), 30 mM NaCl, 3 mM β-mercaptoethanol and 3% newborn calf serum (Gibco).

Osmotic Shock

Immediately after harvesting and washing, the cell-pellet was resuspended in 20% sucrose, 100 mM EDTA, 100 mM Tris HCl (pH 7.4) at a maximal cell density of $1\times10^{10}$/ml. The suspension was kept on ice for 10 minutes and then centrifuged for 10 minutes at 10,000 rpm in the Sorvall SS34 rotor. The sucrose solution was carefully drained from the tube and the pellet was resuspended in an equal volume of water (cell density of $1\times10^{10}$/ml). The resuspended cells remained on ice for 10 min and were then again subjected to a centrifugation at 10,000 rpm for 10 minutes in the SS34 rotor (Sorvall). The supernatant was made 3% in fetal calf serum, 50 mM in HEPES buffer (pH 7), 30 mM in NaCl and 3 mM in β-mercaptoethanol. This supernatant is referred to as "osmotic shock supernatant". It was stored at 0° C.

3. Ammonium Sulfate Precipitation 1 ml of an $(NH_4)_2SO_4$ solution, saturated at room temperature, was added to 0.5 ml of control solution or an S-100 extract. This mixture was kept on ice for at least 30 min, after which the precipitate was pelleted in an Eppendorf centrifuge for 10 min at room temperature. The pellet was redissolved in PBS (phosphate buffered saline).

B. Interferon Titrations

1. Direct Anti-viral assay

HuIFN-β was assayed in microtiter trays (Sterilin) by a CPE (cytophatic effect)-inhibition technique in human fibroblasts trisomic for chromosome 21. The cells were seeded one day before use, incubated with serial dilutions ($\log_{10}=0.5$) of the sample for 24 h and challenged with vesicular stomatitis virus (Indiana strain) $10^{-3}$ dilutions of a stock containing $10^{6.9}$ mouse C-929 plaque forming units/ml. The CPE was recorded at 24 h after VSV challenge and the interferon endpoint was defined as the sample dilution causing 50% reduction of viral CPE. All assays included an internal standard of HuIFN-β which was itself calibrated against the NIH human fibroblast reference G023-902-527.

The cell line trisomic for chromosome 21 (henceforth referred to as $T_{21}$) was derived from a skin biopsy of a female patient with Down's syndrome. Its karyotype has been established and showed diploidy for all chromosomes except for chromosome 21 (trisomic). The sensitivity of this cell line to interferon appears to be comparable to the sensitivity of cell lines trisomic for chromosome 21 described by E. De Clercq et al., "Non-antiviral Activities Of Interferon Are Not Controlled By Chormosome 21", Nature, 256, pp. 132-134 (1975) and E. De Clercq et al., "Chromosome 21 Does Not Code For An Interferon Receptor", Nature, 264, 249-251 (1976).

In other assays the cell line $E_1SM$ (A. Billiau et al., "Human Fibroblast Interferon For Clinical Trials: Production, Partial Purification And Characterization", Anti-microbial Agents And Chemotherapy, 16, 49-55 (1979)) has been used. This cell line is a diploid fibroblast disomic for chromosome 21 and derived from a two-month-old human fetus. Compared to the $T_{21}$ cell line, $E_1SM$ is less sensitive to HuIFN-β by a factor of 10.

2. 2,5-A Synthetase Assay

Another method for detecting the presence of interferon is by the use of a 2,5-A synthetase assay. It has been shown that interferon induces this enzyme, which converts ATP into trimers (and to a lesser extent dimers, tetramers and multimers) of 2,5-A (A. Kimchi et al., "Kinetics Of The Induction Of Three Translation-Regulatory Enzymes By Interferon", Proc. Natl. Acad. Sci. U.S.A., 76, 3208-3212 (1979).

Confluent 25 cm² flasks containing cultures of $E_1SM$ cells (A. Billiau et al., supra) were treated for 20 h with a 1:6 dilution of bacterial extracts or control interferon in MEM-10% fetal calf serum. The cultures were detached with trypsin (0.25%), EDTA (0.17%) and extensively washed with 140 mM NaCl in 35 mM Tris buffer (pH 7.5). All subsequent operations were carried out at 4° C. Cells were homogenized in 1.5-2.0 vol of 20 mM HEPES buffer (pH 7.4) containing 10 mM KCl, 1.5 mM magnesium acetate and 0.5 mM dithiothreitol ("lysis buffer I") in a Dounce glass homogenizer. The homogenate was centrifuged for 20 min at 10,000×g and the supernatant (S10) stored in liquid nitrogen when not used immediately.

Confluent 96-well microtiter plates ($10^5$ cells in 0.2 ml per 0.28 cm² well) were treated with interferon or the respective bacterial extracts as above. After 20 h treatment, plates were cooled on ice and washed three times with 140 mM NaCl in 35 mM Tris buffer (pH 7.5). The cultures were then lysed by adding to each well 5 µl of a solution containing 0.5% Nonidet P40 and 1 mM phenylmethane sulfonyl fluoride (PMSF) in lysis buffer I. After shaking vigorously for 20 min on ice, the cell lysates were collected and centrifuged for 20 min at 10,000×g as above.

3.5 µl of lysate, prepared as indicated above, (lysis A or lysis B) were incubated for 2 h at 31° C. in 6 µl of an incubation mixture containing 100 mM potassium acetate, 25 mM magnesium acetate, 10 mM HEPES/KOH (pH 7.4), 5 mM ATP, 4 mM fructose 1,6 bis-phosphate, 1 mM dithiothreitol and 20 µg/ml poly(I)-poly(C) and 2 µCi of lyophilized ($\alpha$-$^{32}$P)-ATP (400 Ci/mmol, from the Radiochemical Centre, Amersham, U.K.). After stopping the reaction by heating for 3 min at 95° C. and clarification for 2 min at 9,000×g, the samples were treated with 150 U/ml of alkaline phosphatase from calf intestine (Boehringer, Mannheim, cat. nr. 405612) for 1 h at 37° C., clarified again and spotted (1 µl per sample) on thin-layer plates of polyethyleneimine-cellulose (Polygram, cel 300 PEI 20×20 cm from Macherey-Nagel Co., Duren Germany). The plates were washed two times in 2 l of distilled water and dried under vacuum before chromatography in 1 M acetic acid for 2-3 h. After drying they were submitted to autoradiography for 1-24 h.

C. Detection Of HuIFN-β Activity In Bacterial Extracts

1. Control Experiments

Two main problems were encountered in the performance of the above-described assays. Both are important in the interpretation of the assay data. Bacterial extracts (including control extracts) resulting from lysis by the above described procedures seemed to include a non-interferon related factor which displayed anti-viral activity in the assay. It is unclear whether the factor itself was an anti-viral agent, or whether the factor induced an anti-viral substance, e.g., interferon, under the conditions of the assay. The presence of the factor was detected repeatedly in S100 extracts. The activity of the factor was, perhaps because of cell density, often higher in control extracts from E. coli HB101 than in similar control extracts of the K12ΔHI or M5219 host bacteria, where the activity of the factor was always less than about 0.7 $\log_{10}$/ml. For some reason, the anti-viral activity of the factor was reduced or sometimes even eliminated totally by precipitation with $(NH_4)_2SO_4$ under conditions which also precipitated interferon in control experiments.

Due to the anti-viral activity attributable to this contaminating factor, it is difficult to draw conclusions about the presence of trace amounts of interferon in bacterial extracts. However, it was possible to discriminate between the anti-viral activity of the factor and the activity of authentic interferon by the use of the diploid fibroblasts $E_1SM$. These cells are less sensitive to HuIFN-β than the usual cells trisomic for chromosome 21. But, the cells are much more sensitive to the factor, than they are to bona fide interferon. For example, using pMS2-7 (R. Devos et al. "Construction And Characterization Of A Plasmid Containing A Nearly Full-size DNA Copy Of Bacteriophage MS2 RNA", J. Mol. Biol., 128, 595-619 (1979)) in E. coli HB101 (H. Boyer and D. Rouland-Dussoix, "A Complementation Analysis Of Restriction And Modification Of DNA In Escherichia coli", J. Mol. Biol., 41, 459-472 (1969)) or K12ΔHI-G-pPLa2311 as control lysates, data demonstrating this relative effect are shown in the following table, with anti-viral activity measured as $\log_{10}$ units/ml.

|  | $T_{21}$ | $E_1SM$ |
|---|---|---|
| HB101-pMS2-7 (lysis A) | 0.7 | |
| HB101-pMS2-7 (lysis B, but no β-mercaptoethanol and no calf serum) | <0.2 | 1.2 |
| HB101-pMS2-7 (lysis B) | not done | 0.7 |
| HB101-pMS2-7 (lysis B) | 0.2 | 1.0 |
| HB101-pMS2-7 (lysis B) | 0.7 | 2.5 |
| K12ΔHI-G-pPLa2311 (lysis B) | 0.2 | 4.0 |
| K12ΔHI-G-pPLa2311 (42° C.; osmotic shockate) | 0.5 | >1.7 |

Furthermore, the presence of authentic HuIFN-β is reflected by a different ratio of values on $T_{21}$:$E_1SM$ and a high value on $T_{21}$ as compared to that caused by the presence of the factor. This is shown in the following data:

|  |  |  | $T_{21}$ | $E_1SM$ |
|---|---|---|---|---|
| osmotic shock supernatant | K12ΔHI-G-pPLa2311 | (42° C.) | 0.5 | 2.5 |
| | K12ΔHI-G-pPLa2311 + HuIFN-β (authentic) | (42° C.) | 1.5 | 2.5 |
| lysis B after $(NH_4)_2SO_4$ precipitation | HB101-pMS2-7 | | 0.2 | 2.5 |
| | HB101-pMS2-7 + HuIFN-β (authentic) (added before lysis) | | 2.7 | 2.5 |

Therefore, a comparison of the activities $T_{21}$:$E_1SM$ and a measurement of the absolute activity on $T_{21}$ cells permits the use of the anti-viral assays, described above, to detect unambiguously the presence of HuIFN-β in a bacterial extract. Furthermore, it should be noted that for extracts of cultures of *E. coli* (either K12ΔHI or M5219) transformed with some plasmids of this invention, e.g., G-pPLa-HFIF-67-12, G-pPLa-HFIF-67-12Δ19, G-pPLc-HFIF-67-8, G-pPLa-HFIF-67-12Δ279T, G-pPLa-HFIF-67-12Δ218MI, G-pPLa-HFIF-67-12ΔMI or G-pPLa-HFIF-67-12Δ19 BX-2, such interference by the unknown factor in the anti-viral assays was less severe. In these assays, the non-highly concentrated extracts (for example, cells from 150-ml cultures at $6 \times 10^8$ cells/ml were lysed and extracted in 4 ml) displayed a low or undetectable level of anti-viral activity attributable to the unknown factor.

The presence of this contaminating factor has also been shown to be detectable in the 2,5-A synthetase activity assay. Here, however, the factor can be eliminated completely by precipitation with $(NH_4)_2SO_4$. Therefore, the actual presence of HuIFN-β in a bacterial extract, as distinguished from the presence of the contaminating factor, can also be detected unambiguously in this assay.

However, extracts from *E. coli* HB101/G-pBR322 (Pst)/HFIF6, which has an incomplete colinear coding sequence (only the last few base pairs are missing) and is thus unable to express a mature polypeptide, has repeatedly yielded a positive 2,5-A synthetase activity, but so far no discernable anti-viral activity. This demonstrates that the 2,5-A assay cannot be regarded as the only criterion for the presence of a complete bacteria-made interferon. It also demonstrates that less than the complete mature interferon may have useful activity.

2,5-A synthetase activity is measured by $^{32}P$ incorporation into the 2,5-A trimer as shown by autoradiography. Results (repeated 3 times) are shown in the following table, with increasing positive values reflecting increased incorporation of $^{32}P$.

extract a/pHFIF6→+++; after $(NH_4)_2SO_4$ precipitation→++ extract b/pMS2-7→+++; after $(NH_4)_2SO_4$ precipitation→− extract b/pMS2-7→+++; after $(NH_4)_2SO_4$ precipitation→++plus HuIFN-β

A second important problem in these assays is the low recovery of HuIFN-β secreted by human fibroblasts during and after different experimental steps. A comparison of the recoveries of leukocyte interferon and fibroblast interferon added to an S-100 extract demonstrates that HuIFN-β is recovered with only 10% efficiency, in contrast to HuIFN-α's 100% recovery (anti-viral values are given as $\log_{10}$ units/ml; assayed on $T_{21}$ cells).

IFN-α diluted in S-100-extract of HB101-pMS2-7 (lysis A) 2.5

IFN-α diulted in E-MEM plus 3% calf serum 2.7

IFN-β diluted in S-100-extract of HB101-pMS2-7 (lysis A) 0.7

IFN-β diluted in E-MEM-plus 3% calf serum 1.7

Other experiments where IFN-β was added to the cell pellet before lysis and extraction (even with calf serum added to 3% as a stabilizer) showed that only 10-30% IFN-β was recovered.

|  |  |  | $\log_{10}$ units/ml | |
|---|---|---|---|---|
|  |  | HEPES | $T_{21}$ | $E_1SM$ |
| HB101-pMS2-7 plus IFN-β | (lysis B, but no β-mercaptoethanol or calf serum) | pH 8 | 0.7(10%) | 1.7 |
| | | pH 7 | 1.0(20%) | 1.7 |
| | | pH 6 | 0.7(10%) | 1.7 |
| IFN-β (no bacteria) | (same treatment as in lysis B) | pH 6 | 1.7(50%) | 1.5 |

Further experiments were carried out to test the stability and recovery of IFN-β activity. Precipitation with $(NH_4)_2SO_4$, as described above, either in the presence or absence of bacterial extracts, often caused a reduction of the titer in the anti-viral assay:

|  | $\log_{10}$ units/ml | |
|---|---|---|
| Precipitation with $(NH_4)_2SO_4$ | before | after |
| IFN-β | 1.0 | 0.5 |
| IFN-β | 2.7 | 2.5 |
| HB101-pMS2-7 + IFN-β (lysis B) | 1.5 | 1.2 |
| K12ΔHI-G-pPLa2311 (28° C.) + IFN-β (lysis B) | 1.7 | 1.5 |
| K12ΔHI-G-pPLa2311 (28° C.) + IFN-β (lysis B) | 2.2 | 3.0 |

Dialysis of IFN-β (overnight at 4° C. against PBS) either in the presence or in the absence of bacterial extracts, also usually resulted in a decreased recovery of IFN-β activity:

|  | $\log_{10}$ units/ml | |
|---|---|---|
| Dialysis | before | after |
| IFN-β in PBS | 1.0 | 0.5 |
| IFN-β in PBS | 2.7 | 2.5 |
| K12ΔHI-G-pPLa8 (28° C.) + IFN-β (lysis B) | 1.2 | <0.2 |
| K12ΔHI-G-pPLa8 + IFN-β (lysis B) | 3.0 | 1.7 |
| K12ΔHI-G-pPLa8 + IFN-β (lysis B) | 2.5 | 1.0 |
| K12ΔHI-G-pPLa8 + IFN-β (lysis B) | 1.5 | 0.5 |

Since IFN-β is a Type I interferon its activity should be acid-stable. This was tested by dialyzing IFN-β samples in the presence or absence of bacterial extracts, overnight in 5 mM glycine-HCl (pH 2.2) at 4° C. This treatment caused the formation of a precipitate, which was pelleted in an Eppendorf centrifuge at 12,000×g for 2 min. The supernatant was then tested for anti-viral activity. Although some of the anti-viral activity remained following this treatment, there was a substantial loss in the amount of interferon recovered.

|  | $\log_{10}$ units/ml | |
| --- | --- | --- |
| Dialysis | before | after |
| HB101-p-MS2-7 (lysis A) + IFN-β | 0.7 | 0.5 |
| K12ΔHI-G-pPLa2311 (28° C.) osmotic shockate + IFN-β | 1.2 | 1.2 |
| M5219-G-pPLa8 (42° C.) (lysis B) + IFN-β | 1.2 | 0.7 |
| M5219-G-pPLa8 (28° C.) (lysis B) + IFN-β | 3.0 | 2.0 |

The reductions in HuIFN-β activity observed with these different treatments to the above described control extracts must be interpreted cautiously. The lower anti-viral titers do not necessarily mean that interferon is being degraded. The lower titers may be due to non-specific sticking of the HuIFN-β to dialysis membranes or to components in the bacterial extracts, e.g. membrane components. For example, it is well established that IFN-β is a hydrophobic protein (its hydrophobicity is also substantiated by its amino acid sequence) which can adhere non-specifically to tube walls or other surfaces. Furthermore, bacterial IFN-β, lacking glycosylation, may be even more hydrophobic. Therefore, conclusions on the recovery of the glycosylated IFN-β secreted by human cells may not necessarily be extrapolated to IFN-β of bacterial origin.

2. Demonstration of IFN-β Activity a. Anti-viral Activity

Bacterial extracts of *E. coli* M5219 or K12ΔHI, containing the plasmids G-pPLa-HFIF-67-12, G-pPLa-HFIF-67-12Δ19, G-pPLc-HFIF-67-8, G-pPLa-HFIF-67-12Δ279T, G-pPLa-HFIF-67-12Δ218MI, G-pPLa-HFIF-67-12ΔMI, or G-pPLa-HFIF-67-l2Δ19 BX-2 were analyzed for IFN-β antiviral activity. The procedures for induction and preparation of the S-100 extracts and the osmotic shock supernatants were substantially as described above. 150 ml of bacterial culture ($3\text{-}6 \times 10^8$ cells/ml) were used per experiment. All biological titers are given in $\log_{10}$ units/ml.

G-pPLa-HFIF-67-12

G-pPLa-HFIF-67-12 was employed to transform *E. coli* M5219 and *E. coli* K12ΔHI and S-100 extracts were prepared by lysis B. All samples were precipitated with $(NH_4)_2SO_4$ before testing for antiviral activity.

|  | $T_{21}$ | $E_1SM$ |
| --- | --- | --- |
| K12ΔHI-G-pPLa-HFIF-67-12 (28° C.) | <0.2 | <1.0 |
| K12ΔHI-G-pPLa-HFIF-67-12 (42° C., 90 min) | 0.2/0.5 | <1.0/<1.0 |
| M5219-G-pPLa-HFIF-67-12 (28° C.) | <0.2 | <1.0 |
| M5219-G-pPLa-HFIF-67-12 (42° C., 90 min) | 0.7/0.7 | <1.0/<1.2 |

The second figure in the above table is the titer determined on reassay of the same sample. A control experiment where authentic IFN-β was added to *E. coli* HB101-pMS2-7 before lysis of the cells indicated an IFN-β recovery of 30% in the assay. Therefore, it is plain that upon induction IFN-β anti-viral activity is detected in the bacterial lysate. The titers, while below the detection level of $E_1SM$ cells, show clearly that the IFN-β activity is not due to a contaminating bacterial activity. Such a contaminating bacterial activity would give values of at least 2.0 on $E_1SM$ to correspond to the values of 0.5 or 0.7 on $T_{21}$ cells (see control experiments above).

G-pPLa-HFIF-67-12Δ19

Plasmid G-pPLa-HFIF-67-12Δ19 was used to transform *E. coli* M5219 and S-100 extracts were prepared by lysis B. All samples were precipitated with $(NH_4)_2SO_4$, as described above, and assayed for anti-viral activity. Again, the presence of HuIFN-β anti-viral activity in the extracts is plain. The value between brackets indicates the detection level, due to some toxicity of the particular samples for the human cells in tissue culture.

i) M5219-G-pPLa-HFIF-67-12Δ19 (28° C.)

ii) M5219-G-pPLa-HFIF-67-12Δ19 (42° C., 90 min, final cell density=$3 \times 10^8$/ml)

|  | on $T_{21}$ | on $E_1SM$ |
| --- | --- | --- |
| i) | <0.5 | 2.2 (<2.0) |
| ii) | 2.2 (<0.5) | 2.2 (<2.0) |

A control experiment where authentic IFN-β was added to HB101-pMS2-7 before lysis of the cells displayed a 30% recovery. Here, the high values on $T_{21}$ cells and the ratio of activity on $T_{21}$ over that on $E_1SM$ indicate that there was no significant contaminating bacterial activity (as discussed above) in the temperature induced samples.

G-pPLc-HFIF-67-8

Plasmid G-pPLc-HFIF-67-8 was used to transform *E. coli* M5219 and S-100 extracts were prepared by lysis B. All samples were precipitated with $(NH_4)_2SO_4$ and assayed for anti-viral activity.

i) M5219-G-pPLc-HFIF-67-8 (28° C.)

ii) M5219-G-pPLc-HFIF-67-8 (42° C., 180 min, final cell density=$6 \times 10^8$/ml)

|  | on $T_{21}$ | on $E_1SM$ |
| --- | --- | --- |
| i) | <0.5 | 2.2 (<2.0) |
| ii) | 2.2 (<0.5) | 2.2 (<2.0) |

The value in the brackets indicates the detection level, due to toxicity. A control experiment where authentic IFN-β was added to HB101-pMS2-7 before lysis of the cells displayed a 30% recovery. Again, it is plain that the bacterial extract displayed HuIFN-β anti-viral activity.

In another experiment the osmotic shock supernatant of these cells was assayed for IFN-β antiviral activity:

i) control: M5219-G-pPLa-HFIF-67-12Δ19 (28° C.)

ii) M5219-G-pPLc-HFIF-67-8 (28° C.)

iii) M5219-G-pPLc-HFIF-67-8 (42° C., 180 min, cell density=$6 \times 10^8$/ml).

The assays were performed on $T_{21}$ cells, both before and after $(NH_4)_2SO_4$ precipitation. The value between brackets indicates the limit of detection.

|  | before precipitation | after precipitation |
| --- | --- | --- |
| i) | <0.2 | <0.2 |
| ii) | <0.2 | <0.2 |
| iii) | 1.5 (<0.2) | 0.7 (<0.2) |

The recovery of IFN-β was about 10% in control experiments. The control lysates did not show detectable activity on $E_1SM$. The values obtained with the osmotic shock supernatants make plain that the temperature-induced M5219-G-pPLc-HFIF-67-8 extract has an anti-viral activity not present in the non-induced samples. Sample (iii) after precipitation with $(NH_4)_2SO_4$, having a titer of 0.7 $log_{10}$ units per ml, was dialysed to pH 2.2, as described above, and showed no substantial decrease of activity. This acid-stability is a particular property of type I interferons, e.g. IFN-β.

G-pPLa-HFIF-67-12Δ279T

Plasmid G-pPLa-HFIF-67-12ΔA279T was used to transform E. coli M5219 and S-100 extracts were prepared by lysis B. Samples were precipitated with $(NH_4)_2SO_4$ before assay by CPE on $T_{21}$ cells. The extracts of cells induced at 42° C. displayed an anti-viral titer of 1.5-1.7 $log_{10}$ u/ml of extract.

G-pPLa-HFIF-67-12Δ218MI

Plasmid G-pPLa-HFIF-67-12Δ218MI was used to transform E. coli M5219 and S-100 extracts were prepared by lysis B. Samples were precipitated with $(NH_4)_2SO_4$ before assay by CPE on $T_{21}$ cells. The extracts of cells induced at 42° C. displayed an anti-viral titer of 1.5 $log_{10}$ u/ml of extract.

G-pPLa-HFIF-67-12ΔMI

Plasmid G-pPLa-HFIF-67-12ΔMI was used to transform E. coli M5219 and S-100 extracts were prepared by lysis B. Samples were precipitated with $(NH_4)_2SO_4$ before assay by CPE on $T_{21}$ cells. The extracts of cells induced at 42° C. displayed an anti-viral titer of 2.0 $log_{10}$ u/ml of extract.

G-pPLa-HFIF-67-12Δ19 BX-2

Plasmid G-pPLa-HFIF-67-12Δ19 BX-2 was used to transform E. coli K12ΔHI and S-100 extracts were prepared by lysis B. Samples were precipitated with $(NH_4)_2SO_4$ before assay by CPE on $T_{21}$ and FS-4 cells. The extracts of cells induced at 42° C. displayed an anti-viral titer of 1.7-2.0 $log_{10}$ u/ml of extract.

b. Antibody Neutralization of HuIFN-β Anti-Viral Activity

Further evidence substantiating bacterial expression of IFN-β is given by antibody neutralization experiments. The anti-interferon antiserum was produced in goats, immunized with 107 units of authentic IFN-β (secreted by human fibroblast cells), and purified on controlled pore glass beads (A Billiau et al., supra). After bacterial extracts were assayed as above for antiviral activity, serial dilutions of the antiserum were added to similar samples, the mixtures incubated for 1 h at 37° C., applied to human diploid fibroblasts $T_{21}$ and assayed for anti-viral activity as described before. The degree of neutralization by IFN-β antiserum ranges from +++ (complete neutralization to-(no neutralization). The value between brackets indicates the approximate antiserum dilution for 50% neutralization.

1) M5219-G-pPLc-HFIF-67-8 (42° C., 180 min; which gave 2.2 $log_{10}$ antiviral units/ml on $T_{21}$ cells).
2) M5219-G-pPLa-8 (42° C., 180 min) to which IFN-β (from human fibroblasts) was added before lysis (which gave 1.7 $log_{10}$ antiviral units on $T_{21}$ cells).

| dilution of antiserum | (1) | (2) |
|---|---|---|
| $10^{-3}$ | +++ | +++ |
| $10^{-4}$ | + | +++ |
| $10^{-5}$ | ± ($10^{-4.5}$) | +++ |
| $10^{-6}$ | − | ± ($10^{-6}$) |
| $10^{-7}$ | − | − |

Similar results were obtained with extracts from M5219-pPLa-HFIF-67-12Δ19 (42° C.). The differences in neutralization titer between the bacterial IFN-β of this invention and authentic IFN-β may be due to differences in antigenicity or in the specific IFN activity of these bacterial proteins relative to authentic IFN-β caused by lack of glycosylation in the bacterial proteins.

c. Stability Of HuIFN-β Anti-Viral Activity (1) Heat Treatment

IFN-β has, in contrast to IFN-α, the very unusual property that its anti-viral activity is recovered after boiling in 1% SDS, 1% β-mercaptoethanol, 5 M urea (Stewart, W. E. II et al., Distinct Molecular Species of Human Interferon, Requirements For Stabilization And Reactivation Of Human Leucocyte And Fibroblast Interferon, J. Gen. Virol., 26, 327-331, (1975)), although a 100% recovery usually is not obtained. For this assay the bacterial cells of a 150 ml culture were resuspended in the buffer for lysis B and an equal volume of 2% SDS, 2% β-mercaptoethanol and 10 M urea added, the mixture boiled for 2 min, and S-100 fractions prepared.

i) control: M5219-G-pPLa-HFIF-67-12Δ19 (28° C.)

ii) control: 3 $log_{10}$ units of HuIFN-β diluted in lysis B buffer iii) M5219-G-pPLc-HFIF-67-8 (42° C., 180 min, cell density=$6×10^8$/ml).

The assays were performed on $T_{21}$-cells. The value in the brackets indicates the limit of detection, due to intrinsic toxicity.

|  | Before boiling | After boiling |
|---|---|---|
| i) | <1.5 | <1.5 |
| ii) | 2.2 (<1.5) | 2.0 (<0.5) |
| iii) | 3.0 (<2.0) | 2.2 (<1.5) |

The control experiment showed a recovery of about 10% of the IFN-β activity. There was no detectable value in $E_1SM$ in parallel control lysates. These data make plain that although only about 10% of added IFN-β is recovered in the control experiment, that IFN-β anti-viral activity was present in the extract from the temperature induced M5219-G-pPL-c-HFIF-67-8 culture even after this severe treatment. In fact, a higher antiviral activity was found after this treatment as compared to the lysis B procedure, indicating possible adherence of IFN-β to cell components in the latter procedure.

(2) Dialysis

The HuIFN-β anti-viral activity is also non-dialysable. For example, after dialysis against PBS for 16 h at neutral pH and 4° C. the anti-viral activity ($log_{10}$ u/ml) of the bacterial extracts was maintained, albeit at a reduced titer:

i) M5219-pPLc-HFIF-67-8 (42° C.)

ii) M5219-pPLa-HFIF-67-12Δ19 (42° C.)

iii) IFN-β in M5219-pPLa-8 (42° C.)

|  | Before dialysis | After dialysis |
|---|---|---|
| i) | 2.3 | 2.3 |
| i) | 3 | 2.3 |
| i) | 1.5 | 1.3 |
| ii) | 2.3 | 1.3 |
| ii) | 2.3 | 2 |
| ii) | 2.3 | 1 |

The observed decrease in activity after dialysis may be due to non-specific sticking of IFN-β to dialysis membranes, etc.

(3) Precipitation with $(NH_4)_2SO_4$

The anti-viral activity ($\log_{10}$ u/ml) of the bacterial extracts of this invention was maintained after precipitation with 67% saturated ammonium sulphate (2 vol $(NH_4)_2SO_4$ solution to 1 vol extract), a concentration known to precipitate HuIFN-β. After 30 min on ice, the pallet was centrifuged at 12000×g for 10 min and redissolved in PBS for assay:

i) M5219-pPLc-HFIF-67-8 (42° C.)

ii) M5219-pPLa-HFIF-67-12Δ19 (42° C.)

iii) IFN-β in M5219-pPLa-8 (42° C.)

|  | before precipitation | after precipitation |
|---|---|---|
| i) | 2 | 2 |
| i) | 2 | 2.3 |
| ii) | 2 | 2 |
| iii) | 1.3 | 1.3 |
| iii) | 1.5 | 1.3 |

(4) pH 2 Treatment

The anti-viral activity ($\log_{10}$ u/ml) of the bacterial extracts of this invention were also stable to acid. The extracts were either dialyzed for 15 h against 50 ml glycine-HCl (pH 2.2), followed by dialysis against PBS for 3 h or acidified with HCl, followed by neutralization with NaOH. After removal of the precipitate the assay was conducted:

i) M5219-pPLc-HFIF-67-8 (42° C.)

ii) M5219-pPLa-HFIF-67-12Δ19 (42° C.)

iii) IFN-β in M5219-pPLa-8 (42° C.)

|  | before acid | after acid |
|---|---|---|
| i) | 2 | 1.3 |
| i) | 0.7 | 0.7 |
| ii) | 2 | 1 |
| iii) | 3 | 2 | d. 2,5-A Synthetase Activity

The osmotic shockates of M5219-G-pPLc-HFIF-67-8 (described above) were assayed for the presence of 2,5-A synthetase, as described above, with microtiter plates, except that Hela cells were used instead of $E_1$SM cells. The following results were obtained:

i) M5219-G-pPLc-HFIF-67-8 (28° C.) (see above)

ii) M5219-G-pPLc-HFIF-67-8 (42° C.) (see above)

The values, reflecting the 2,5-A synthetase activity, indicate the $^{32}$P-radioactivity incorporated in the trimer form of 2,5-A.

|  | (measured counts) | (after substraction of endogenous background) |
|---|---|---|
| 1) non treated cells | 3342 cpm | 0 cpm |
| 2) bacterial extract (i): dilution 1/6 | 1972 cpm | −1370 cpm |
| 3) bacterial extract (ii): dilution 1/6 | 6960 cpm | 3618 cpm |
| 4) bacterial extract (i) + IFN-β to 1.5 $\log_{10}$ units/ml | 7037 cpm | 3695 cpm |
| 5) see 3 but incubated with anti-IFN-β antiserum | 3950 cpm | 608 cpm |
| 6) see 4 but incubated with anti-IFN-β antiserum | 2960 cpm | −382 cpm |
| 7) control IFN-β 0.5 $\log_{10}$ units/ml | 4463 cpm | 1120 cpm |
| 8) control IFN-β 1 $\log_{10}$ units/ml | 7680 cpm | 4338 cpm |
| 9) control IFN-β 1.5 $\log_{10}$ units/ml | 13615 cpm | 10273 cpm |
| 10) control IFN-β 2 $\log_{10}$ units/ml | 25040 cpm | 21698 cpm |

The results of the 2,5-A synthetase activity assay demonstrate that the osmotic shockate supernatant of the temperature induced M5219-G-pPLc-HFIF-67-8, which has anti-viral activity (see above), is also inducing 2,5-A synthetase activity while the non-induced bacterial strain is not. This parallels the results of the anti-viral activity assay.

The degree of stimulation of 2,5-A synthetase is equal to the activity of IFN-β added to the control lysate (compare samples (3) and (4)). Use of a concentration curve developed from samples (7) to (10)) shows that, taking into account the dilution, an activity of $\log_{10}$ 1.7 units/ml can be estimated in both samples (3) and (4), which is compatible with the values in the direct antiviral assay, i.e. 1.5 $\log_{10}$ units for both samples. This series of experiments also demonstrates that the induction of 2,5-A synthetase can be neutralized by anti-IFN-β antiserum, as is the case in the antiviral assay.

e. Anti-viral Activity On Other Cell Lines

The extracts (i) and (ii) (M5219-G-pPLc-HFIF-67-8, above) were also tested for antiviral activity on different cell lines of feline, mouse, monkey or rabbit origin. They did not show any detectable antiviral activity on these cells; neither did authentic IFN-β, made by human cells. Also no activity was found on a feline lung cell line which was sensitive to human leucocyte interferon. These results provide further substantiation that the IFN-β produced by the bacteria exhibits properties essentially identical to those of IFN-β secreted by induced human fibroblast cells.

f. Sensitivity To Protease

The sensitivity of IFN-β from the bacterial hosts of this invention was tested by treatment of diluted bacterial extracts with increasing amount of trypsin for 1 h at 37° C. The anti-viral activity of the IFN-β was abolished by the trypsin at a similar concentration to that which abolished the activity of authentic IFN-β added to an inactive control lysate.

|  | | | Trypsin Endpoint (ms/ml) |
|---|---|---|---|
| M5219-pPLa-HFIF-67-12Δ19 | (42° C.) | (1000 u/ml) | 0.03 |
| M5219-pPLc-HFIF-67-8 | (42° C.) | (1000 u/ml) | 0.03 |
| IFN-β in M5219-pPLa-8 | (42° C.) | (1000 u/ml) | 0.03 |
| M5219-pPLc-HFIF-67-8 | (42° C.) | (30 u/ml) | 0.03 |
| IFN-β in M5219-pPLa-8 | (42° C.) | (30 u/ml) | 0.03 |

3. Identification of the Active IFN-β Product

Various experiments have demonstrated that pre-HuIFN-β is not active and is not processed by bacterial cells or under assay conditions to an active product. Therefore, the IFN-β activity detected in the various bacterial extracts, described above, is probably due to processing of the expected fused proteins (e.g., HuIFN-β fused to β-lactamase, MS2 or bacterial signal sequences) by the bacteria or under the conditions of the assay to an active product.

It is not certain that the active product in such extracts is mature HuIFN-β (mature HuIFN-β is, of course, the product of G-pPLa-HFIF-67-12ΔM1 and G-pPLa-HFIF-67-12Δ19 BX-2). However, fractionation of the bacterial extracts obtained, for example, from induced M5219-pPLa-HFIF-67-12Δ19 or from induced by polyacrylamide gel electrophoresis under denaturing conditions revealed the presence of two active products. The first of those products had an approximate size of 15000-18000 daltons and could correspond to mature IFN-β. The second product, which had a higher molecular weight, may be a fusion product or an incompletely processed product which has IFN-β activity or may be a product that is processed to mature IFN-β under the conditions of the assay. Amino acid sequencing of the various expression products, using well known techniques, will enable a determination of what protein products, if any, in addition to mature HuIFN-β, display the activity of HuIFN-β.

IMPROVING THE YIELD AND ACTIVITY OF POLYPEPTIDES DISPLAYING HuIFN-β ACTIVITY PRODUCED IN ACCORDANCE WITH THIS INVENTION

The level of production of a protein is governed by three major factors: the number of copies of its gene within the cell, the efficiency with which those gene copies are transcribed and the efficiency with which they are translated. Efficiency of transcription and translation (which together comprise expression) is in turn dependent upon nucleotide sequences, normally situated ahead of the desired coding sequence. These nucleotide sequences or expression control sequences define, inter alia, the location at which RNA polymerase interacts to initiate transcription (the promoter sequence) and at which ribosomes bind and interact with the mRNA (the product of transcription) to initiate translation. Not all such expression control sequences function with equal efficiency. It is thus of advantage to separate the specific coding sequences for the desired protein from their adjacent nucleotide sequences and to fuse them instead to other known expression control sequences so as to favor higher levels of expression. This having been achieved, the newly engineered DNA fragment may be inserted into a higher copy number plasmid or a bacteriophage derivative in order to increase the number of gene copies within the cell and thereby further improve the yield of expressed protein.

Several expression control sequences may be employed as described above. These include the operator, promoter and ribosome binding and interaction sequences (including sequences such as the Shine-Dalgarno sequences) of the lactose operon of E. coli ("the lac system"), the corresponding sequences of the tryptophan synthetase system of E. coli ("the trp system"), the major operator and promoter regions of phage λ ($O_L P_L$ as described above and $O_R P_R$), a control region of Filamentous single-stranded DNA phages, or other sequences which control the expression of genes of prokaryotic or eukaryotic cells and their viruses. Therefore, to improve the production of a particular polypeptide in an appropriate host, the gene coding for that polypeptide may be prepared as before and removed from a recombinant DNA molecule closer to its former expression control sequence or under the control of one of the above expression control sequences. Such methods are known in the art.

Other methods to improve the efficiency of translation involve insertion of chemically or enzymatically prepared oligonucleotides in front of the initiating codon. By this procedure a more optimal primary and secondary structure of the messenger RNA can be obtained. More specifically, the sequence can be so designed that the initiating AUG codon occurs in a readily accessible position (i.e., not masked by secondary structure) either at the top of a hairpin or in other single-stranded regions. Also the position and sequence of the aforementioned Shine-Dalgarno segment can likewise be optimized. The importance of the general structure (folding) of the messenger RNA has been documented (D. Iserentant and W. Fiers "Secondary Structure Of mRNA And Efficiency Of Translation Initiation", Gene, 9, 1-12 (1980).

Further increases in the cellular yield of the desired products depend upon an increase in the number of genes that can be utilized in the cell. This may be achieved by insertion of the HuIFN-β gene (with or without its transcription and translation control elements) in an even higher copy number plasmid or in a temperature-controlled copy number plasmid (i.e., a plasmid which carries a mutation such that the copy number of the plasmid increases after shifting up the temperature; B. Uhlin et al. "Plasmids With Temperature-dependent Copy Number For Amplification Of Cloned Genes And Their Products", Gene, 6, 91-106 (1979)). Alternatively, an increase in gene dosage can be achieved for example by insertion of recombinant DNA molecules engineered in the way described previously into the temperate bacteriophage λ, most simply by digestion of the plasmid with a restriction enzyme, to give a linear molecule which is then mixed with a restricted phage λ cloning vehicle (e.g., of the type described by N. E. Murray et al., "Lambdoid Phages That Simplify The Recovery Of In Vitro Recombinants", Mol. Gen. Genet., 150, 53-61 (1977) and N. E. Murray et al., "Molecular Cloning Of The DNA Ligase Gene From Bacteriophage T4", J. Mol. Biol., 132, 493-505 (1979) and the recombinant DNA molecule produced by incubation with DNA ligase. The desired recombinant phage is then selected as before and used to lysogenize a host strain of E. coli.

Particularly useful λ cloning vehicles contain a temperature-sensitive mutation in the repression gene cI and suppressible mutations in gene S, the product of which is necessary for lysis of the host cell, and gene E, the product which is the major capsid protein of the virus. With this system the lysogenic cells are grown at a relatively low temperature (e.g., 28°-32° C.) and then heated to a higher temperature (e.g., 40°-45° C.) to induce excision of the prophage. Prolonged growth at higher temperature leads to high levels of production of the protein, which is retained within the cells, since these are not lysed by phage gene products in the normal way, and since the phage gene insert is not encapsidated it remains available for further transcription. Artificial lysis of the cells then releases the desired product in high yield. As in this application we have also used the λ repressor system to control expression, it may be necessary to control the excision of the prophage and hence the gene copy number by a heteroimmune control region, e.g., derived from the lambdoid phage 21.

It should be understood that polypeptides displaying IFN-β activity (prepared in accordance with this invention) may be prepared in the form of a fused protein (e.g., linked to a prokaryotic N-terminal segment directing excretion), or in the form of prointerferon (e.g., starting with the interferon signal sequence which could be cleaved off upon excretion) or as mature interferon (the latter is feasible because mature fibroblast interferon starts with methionine, an amino acid used for initiation of translation). The yield of these different forms of polypeptide may be improved by any or a combination of the procedures discussed above. Also different codons for some or all of the codons used in the present DNA sequences could be substituted. These substituted codons may code for amino acids identical to those coded for by the codons replaced but result in higher yield of the polypeptide. Alternatively, the replacement of one or a combination of codons leading to amino acid replacement or to a longer or shorter HuIFN-β-related polypeptide may alter its properties in a useful way (e.g., increase the stability, increase the solubility, increase the antiviral activity, increase the 2,5-A synthetase activity or increase the host specificity range).

One example of such improvement was obtained by inserting a DNA fragment of this invention including the DNA sequence coding for pre-IFN-β into a cloning vehicle containing the late promoter and splicing sequences of SV40 under the control of that promoter. Such construction in monkey cells yielded about $10^4$ units/ml of processed IFN-β. Similar constructions in other cloning vectors and eukaryotic cells are also envisioned herein.

Finally, the activity of the polypeptides produced by the recombinant DNA molecules of this invention may be improved by fragmenting, modifying or derivatizing the DNA sequences or polypeptides of this invention by well-known means, without departing from the scope of this invention.

IDENTIFICATION OF A CHROMOSOMAL GENE CODING FOR HuIFN-β

A collection of hybrid phage derived from fragments of fetal human chromosomal DNA which had been generated by partial cleavage with HaeIII and AluI, and joined with EcoRI linkers to λ Charon 4A arms has been prepared by R. M. Lawn et al., Cell, 15, pp. 1157-74 (1978). This gene bank was screened by an "in situ" procedure (W. D. Benton and R. W. Davis, Science, 196, pp. 180-82 (1977); T. Maniatis et al., Cell, 15, pp. 687-701 (1978)); using as a probe the $^{32}$P-labelled IFN-β cDNA insert excised by TaqI-BglII restriction from pHFIF21.* One hybridization-positive phage clone was isolated from 600,000 plaques by repeated plaque purification (T. Maniatis et al., supra). This plaque was designated λCH4A-gHFIF1. Restriction analysis of this plaque demonstrated that it contains about 16.3 Kb of human DNA.

EcoRI digestion of λCH4A-gHFIF1 generated, in addition to the two Charon 4A phage arms, eight insert fragments— 4.6, 3.5, 2.4, 1.9, 1.3, 1.2, 0.8 and 0.6 Kb in length. After Southern blotting, only the 1.9 Kb fragment hybridized to the TaqI-BglII fragment of pHFIF21.

The 1.9 Kb fragment was recloned directly into the EcoRI site of pBR325 (a derivative of pBR322 which also carries a chloramphenicol resistance marker containing a single EcoRI site). After ligation of 0.6 μg EcoRI-digested λCH4A-gH-FIF1 DNA to 100 ng pBR325 and transformation into E.coli HB101, several clones were selected. Only those clones containing the 1.9 Kb fragment hybridized to the IFN-β cDNA probe. This clone was designated p[325]-gHFIF4.

Comparison of the restriction fragment derived from pHFIF21 and p[325]-gHFIF4 demonstrated that there are no intervening sequences in the chromosomal clone Plasmid pHFIF21 was identified by the screening processes of this invention. The TaqI-BglII fragment of that plasmid contains nearly the total 5'-untranslated region and the total coding region of IFN-β. and that the DNA information carried by that clone is identical to that of pHFIF21.

The identification and isolation of the chromosomal DNA coding for HuIFN-β enables the transformation of appropriate hosts with that DNA and the expression of HuIFN-β from it. Such expression is advantageous because the various signals associated with chromosomal DNA sequences will be present in such clones. These signals will then be available to trigger higher yields on expression and perhaps post-expression processing of the polypeptide coded for by the coding region of the chromosomal DNA.

Micro-organisms and recombinant DNA molecules prepared by the processes described herein are exemplified by cultures deposited in the culture collection Deutsche Sammlung von Mikroorganism in Gottingen, West Germany on Apr. 2, 1980, and identified as HFIF-A to C:

A: E. coli HB101 (G-pBR322(Pst)/HFIF3)
B: E. coli HB101 (G-pBR322(Pst)/HFIF6)
C: E. coli HB101 (G-pBR322(Pst)/HFIF7)

These cultures were assigned accession numbers DSM 1791-1793, respectively. They are also exemplified by cultures deposited in the culture collection Deutsche Sammlung von Mikroorganism in Gottingen, West Germany on Jun. 5, 1980, and identified as HFIF-D to G:

D: E. coli M5219 (G-pPLa-HFIF-67-12)
E: E. coli K12ΔHI (G-pPLa-HFIF-67-12)
F: E. coli M5219 (G-pPLa-HFIF-67-12Δ19)
G: E. coli M5219 (G-pPLc-HFIF-67-8)

These cultures were assigned accession numbers DSM 1851-1854, respectively. And, by cultures deposited in the America Type Culture Collection, Rockville, Md. on Feb. 26, 1981, and identified as HFIF H and I:

H: E. coli M5219 (pPLa-HFIF-67-12ΔMI)
I: E. coli HB101 (p[325]-gHFIF4)

These cultures were assigned accession numbers ATCC 31824 and 31825, respectively.

While we have herein before presented a number of embodiments of this invention, it is apparent that our basic construction can be altered to provide other embodiments which utilize the processes and compositions of this invention. Therefore, it will be appreciated that the scope of this invention is to be defined by the claims appended hereto rather than the specific embodiments which have been presented herein before by way of example.

I claim:

1. A method for treating human cancers or tumors comprising the step of administering to a patient in need of such treatment a therapeutically effective amount of a composition comprising:
   1) a recombinant polypeptide produced by a non-human host transformed by a recombinant DNA molecule comprising a DNA sequence selected from the group consisting of:

(a) DNA sequences which are capable of hybridizing to any of the DNA inserts of G-pBR322(Pst)/HFIF1, G-pBR322(Pst)/HFIF3 (DSM 1791), G-pBR322 (Pst)/HFIF6 (DSM 1792), and G-pBR322(Pst)/HFIF7 (DSM 1793) under hybridizing conditions of 0.75 M NaCl at 68° C. and washing conditions of 0.3 M NaCl at 68° C., and which code for a polypeptide displaying antiviral activity, and (b) DNA sequences which are degenerate as a result of the genetic code to the DNA sequences defined in (a); said DNA sequence being operatively linked to an expression control sequence in the recombinant DNA molecule; and 2) a pharmaceutically acceptable carrier.

2. The method according to claim 1, wherein said DNA sequence is selected from DNA sequences of the formulae:
ATGACCAACAAGTGTCTCCTCCAAAT-
TGCTCTCCTGTTGTGCTTCTCCACTACAGCT
CTTTCCATGAGCTACAACTTGCTTGGAT-
TCCTACCAAAGAAGCAGGAATTTTCAGTGT
CAGAAGCTCCTGTGGCAATTGAATGG-
GAGGCTTGAATACTGCCTCAAGGACAGGAT
GAACTTTGACATCCCTGAGGAGATTAAG-
CAGCTGCAGCAGTTCCAGAAGGAGGACG CCG-
CATTGACCATCTATGAGATGCTCCAGAA-
CATCTTTGCTATTTTCAGACAAGATT
CATCTAGCACTGGCTGGAATGAGACTAT-
TGTTGAGAACCTCCTGGCTAATGTCTATCATCA-
GATAAACCATCTGAAGACAGTCCTGGAA-
GAAAAACTGGAGAAAGAAGATTTC
ACCAGGGGAAAACTCATGAGCAGTCTG-
CACCTGAAAAGATATTATGGGAGGATTCT
GCATTACCTGAAGGCCAAGGAGTACAGT-
CACTGTGCCTGGACCATAGTCAGAGTGG
AAATCCTAAGGAACTTTTACTTCATTAA-
CAGACTTACAGGTTACCTCCGAAAC, and
ATGAGCTACAACTTGCTTGGATTCCTA-
CAAAGAAGCAGCAATTTTCAGTGTCAGAAG
CTCCTGTGGCAATTGAATGGGAGGCT-
TGAATACTGCCTCAAGGACAGGATGAACTTT
GACATCCCTGAGGAGATTAAGCAGCTG-
CAGCAGTTCCAGAAGGAGGACGCCCGCATT
GACCATCTATGAGATGCTCCAGAA-
CATCTTTGCTATTTTCAGACAAGATTCATCTAG CACTGGCTGGAATGAGACTATTGT-
TGAGAACCTCCTGGCTAATGTCTATCATCAGAT
AAACCATCTGAAGACAGTCCTGGAA-
GAAAAACTGGAGAAAGAAGATTTCACCAGGG
GAAAACTCATGAGCAGTCTGCACCT-
GAAAAGATATTATGGGAGGATTCTGCATTACC
TGAAGGCCAAGGAGTACAGTCACTGTGC-
CTGGACCATAGTCAGAGTGGAAATCCTA
AGGAACTTTTACTTCATTAACAGACTTA-
CAGGTTACCTCCGAAAC.

3. The method according to claim 1 wherein the polypeptide is selected from polypeptides of the formulae:
Met-Thr-Asn-Lys-Cys-Leu-Leu-Gln-Ile-Ala-Leu-Leu-
Leu-Cys-Phe-Ser-Thr-Thr-Ala-Leu-Ser-Met-Ser-Tyr-
Asn-Leu-Leu-Gly-Phe-Leu-Gln-Arg-Ser-Ser-Asn-
Phe-Gln-Cys-Gln-Lys-Leu-Leu-Trp-Gln-Leu-Asn-
Gly-Arg-Leu-Glu-Tyr-Cys-Leu-Lys-Asp-Arg-Met-
Asn-Phe-Asp-Ile-Pro-Glu-Glu-Ile-Lys-Gln-Leu-Gln-
Gln-Phe-Gln-Lys-Glu-Asp-Ala-Ala-Leu-Thr-Ile-Tyr-
Glu-Met-Leu-Gln-Asn-Ile-Phe-Ala-Ile-Phe-Arg-Gln-
Asp-Ser-Ser-Ser-Thr-Gly-Trp-Asn-Glu-Thr-Ile-Val-
Glu-Asn-Leu-Leu-Ala-Asn-Val-Tyr-His-Gln-Ile-Asn-
His-Leu-Lys-Thr-Val-Leu-Glu-Glu-Lys-Leu-Glu-Lys-
Glu-Asp-Phe-Thr-Arg-Gly-Lys-Leu-Met-Ser-Ser-Leu-
His-Leu-Lys-Arg-Tyr-Tyr-Gly-Arg-Ile-Leu-His-Tyr-
Leu-Lys-Ala-Lys-Glu-Tyr-Ser-His-Cys-Ala-Trp-Thr-
Ile-Val-Arg-Val-Glu-Ile-Leu-Arg-Asn-Phe-Tyr-Phe-
Ile-Asn-Arg-Leu-Thr-Gly-Tyr-Leu-Arg-Asn, and Met-
Ser-Tyr-Asn-Leu-Leu-Gly-Phe-Leu-Gln-Arg-Ser-Ser-
Asn-Phe-Gln-Cys-Gln-Lys-Leu-Leu-Trp-Gln-Leu-
Asn-Gly-Arg-Leu-Glu-Tyr--Cys-Leu-Lys-Asp-Arg-
Met-Asn-Phe-Asp-Ile-Pro-Glu-Glu-Ile-Lys-Gln-Leu-
Gln-Gln-Phe-Gln-Lys-Glu-Asp-Ala-Ala-Leu-Thr-Ile-
Tyr-Glu-Met-Leu-Gln-Asn-Ile-Phe-Ala-Ile-Phe-Arg-
Gln-Asp-Ser-Ser-Ser-Thr-Gly-Trp-Asn-Glu-Thr-Ile-
Val-Glu-Asn-Leu-Leu-Ala-Asn-Val-Tyr-His-Gln-Ile-
Asn-His-Leu-Lys-Thr-Val-Leu-Glu-Glu-Lys-Leu-Glu-
Lys-Glu-Asp-Phe-Thr-Arg-Gly-Lys-Leu-Met-Ser-Ser-
Leu-His-Leu-Lys-Arg-Tyr-Tyr-Gly-Arg-Ile-Leu-His-
Tyr-Leu-Lys-Ala-Lys-Glu-Tyr-Ser-His-Cys-Ala-Trp-
Thr-Ile-Val-Arg-Val-Glu-Ile-Leu-Arg-Asn-Phe-Tyr-
Phe-Ile-Asn-Arg-Leu-Thr-Gly-Tyr-Leu-Arg-Asn.

* * * * *